United States Patent
Graham et al.

(10) Patent No.: US 8,569,299 B2
(45) Date of Patent: Oct. 29, 2013

(54) PROLYLCARBOXYPEPTIDASE INHIBITORS

(75) Inventors: Thomas H. Graham, Scotch Plains, NJ (US); Wensheng Liu, Edison, NJ (US); Iyassu K. Sebhat, Jersey City, NJ (US); Dong-Ming Shen, Edison, NJ (US); Zhi-Cai Shi, Monmouth Junction, NJ (US)

(73) Assignee: Merck Sharp & Dohme Corp, Rahway, NJ (US)

( * ) Notice: Subject to any disclaimer, the term of this patent is extended or adjusted under 35 U.S.C. 154(b) by 0 days.

(21) Appl. No.: 13/702,622

(22) PCT Filed: Jun. 3, 2011

(86) PCT No.: PCT/US2011/039040
§ 371 (c)(1),
(2), (4) Date: Dec. 7, 2012

(87) PCT Pub. No.: WO2011/156220
PCT Pub. Date: Dec. 15, 2011

(65) Prior Publication Data
US 2013/0143859 A1    Jun. 6, 2013

Related U.S. Application Data

(60) Provisional application No. 61/352,593, filed on Jun. 8, 2010.

(51) Int. Cl.
- *A61K 31/5377* (2006.01)
- *A61K 31/454* (2006.01)
- *C07D 413/14* (2006.01)
- *C07D 401/02* (2006.01)
- *C07D 401/14* (2006.01)

(52) U.S. Cl.
USPC ........ 514/236.5; 514/326; 544/130; 546/210; 546/211

(58) Field of Classification Search
USPC ......... 514/236.5, 326; 544/130; 546/210, 211
See application file for complete search history.

(56) References Cited

U.S. PATENT DOCUMENTS

| | | |
|---|---|---|
| 2002/0094989 A1 | 7/2002 | Hale et al. |
| 2005/0070609 A1 | 3/2005 | Finke et al. |
| 2008/0108080 A1 | 5/2008 | Chissoe |

FOREIGN PATENT DOCUMENTS

| | | |
|---|---|---|
| EP | 1 498 424 A2 | 1/2005 |
| EP | 1 498 424 A3 | 5/2005 |
| WO | 02/067869 A2 | 9/2002 |
| WO | 02/067869 A3 | 9/2002 |
| WO | 2004/072265 A2 | 8/2004 |
| WO | 2004/072265 A3 | 8/2004 |
| WO | 2005/115446 A2 | 12/2005 |
| WO | 2005/115446 A3 | 12/2005 |
| WO | 2006/120478 A2 | 11/2006 |
| WO | 2006/120478 A3 | 11/2006 |
| WO | 2007/015162 A1 | 2/2007 |
| WO | 2007/041061 A2 | 4/2007 |
| WO | 2007/041061 A3 | 4/2007 |
| WO | 2007/047496 A2 | 4/2007 |
| WO | 2007/047496 A3 | 4/2007 |
| WO | 2007/140896 A1 | 12/2007 |
| WO | 2008/039418 A2 | 4/2008 |
| WO | 2008/039418 A3 | 4/2008 |
| WO | 2011/137012 A1 | 11/2011 |
| WO | 2011/137024 A1 | 11/2011 |
| WO | 2011/143057 A1 | 11/2011 |
| WO | 2011/146300 A1 | 11/2011 |
| WO | 2011/146354 A1 | 11/2011 |
| WO | 2011/156246 A1 | 12/2011 |

OTHER PUBLICATIONS

Bray, G. A. et al., "Sibutramine Produces Dose-Relate Weight Loss", Obesity Research, 1999, p. 189-198, vol. 7. No. 2.

Davidson, M. H. et al., "Weight Control and Risk Factor Reduction in Obese Subjects Treated for 2 Years With Orlistat", JAMA, 1999, p. 235-245, vol. 281, No. 3.

Douglas, A. et al., "Plasma Phentermine Levels, Weight Loss and Side-Effects", International Journal of Obesity, 1983, p. 591-595, vol. 7.

(Continued)

*Primary Examiner* — Samantha Shterengarts
(74) *Attorney, Agent, or Firm* — Baerbel R. Brown; Catherine D. Fitch

(57) ABSTRACT

Compounds of structural formulas I-1 and I-2 are inhibitors of prolylcarboxypeptidase (PrCP). The compounds of the present invention are useful for the prevention and treatment of conditions related to the enzymatic activity of PrCP such as abnormal metabolism, including obesity; diabetes; metabolic syndrome; obesity related disorders; and diabetes related disorders.

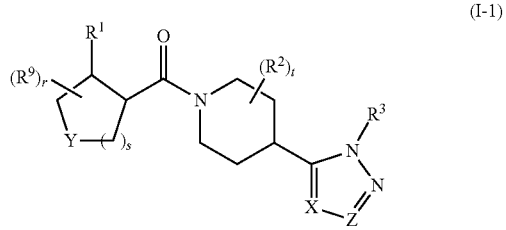

(I-1)

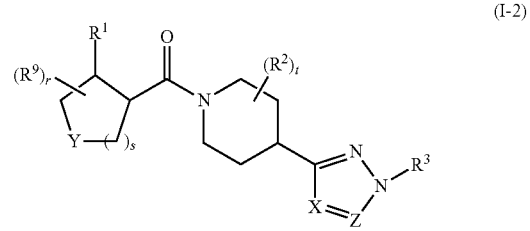

(I-2)

22 Claims, No Drawings

(56) References Cited

OTHER PUBLICATIONS

Duncia, J. V. et al., "Three Synthetic Routes to a Sterically Hindered Tetrazole. A New One-Step Mil Conversion of an Amide into a Tetrazole", J. Org. Chem, 1991, p. 2395-2400, vol. 56.

Encinosa, W. E. et al., "Recent Improvements in Bariatric Surgery Outcomes", Medical Care, 2009, p. 531-, vol. 47, No. 5.

Flum, D. R. et al., Early Mortality Among Medicare Beneficiaries Undergoing Bariatric Surgical Procedures, JAMA, 2005, p. 1903-, vol. 294, No. 15.

Giraudo, S. Q. et al., "Feeding effects of hypothalamic injection of melanocortin 4 receptor ligands", Brain Research, 1998, p. 302-306, vol. 809.

Guo, L. et al., "Synthesis and SAR of potent and orally bioavailable tert-butylpyrrolidine archetype derived melanocortin subtype-4 receptor modulators", Bioorganic & Medicinal Chemistry Letters, 2008, p. 3242-3247, vol. 18.

Guy-Grand, B. et al., "International Trial of Long-Term Dexfenfluramine in Obesity", The Lancet, 1989, p. 1142-1145.

Kask, A. et al., "Selective Antagonist for the Melanocortin 4 Receptor (HS014) Increases Food Intake in Free-Feeding Rats", Biochemical and Biophysical Research Communications, 1998, p. 90-93, vol. 245.

Kopelman, P. G., "Obesity as a medical problem", Nature, 2000, p. 635-643, vol. 404.

Lansdell, M. I. et al. "Discovery of a Selective Small-Molecule Melanocortin-4 Receptor Agonist with Efficacy in a Pilot Study of Sexual Dysfunction in Humans", J. Med. Chem, 2010, p. 3183-3197, vol. 53.

Lin Y. et al., "Synthesis of 1,2,4-Triazoles and 1.2.4-Oxadiazoles [1]", J. Heterocyclic Chem, 1983, p. 1693-1695, vol. 20.

Vaisse, C. et al., "Melanocortin-4 receptor mutations are a frequent and heterogeneous cause of morbid obesity", The Journal of Clinical Investigation, 2000, p. 253-262, vol. 106.

Wallingford, N. et al., "Prolylcarboxypeptidase regulates food intake by inactivating a-MSH in rodents", The Journal of Clinical Investigation, 2009, p. 2291-, vol. 119, No. 8.

Williams, D. L. et al., "The melanocortin system as a central integrator of direct and indirect controls of food intake", Am J Physiol Regul Integr Comp Physiol, 2005, p. R2-R3, vol. 289.

Young, J. R. et al., "Pyrrolidine-carboxamides and oxadiazoles as potent hNK1 antagonists", Bioorganic & Medicinal Chemistry Letters, 2007, p. 5310-5315, vol. 17.

PROLYLCARBOXYPEPTIDASE INHIBITORS

CROSS-REFERENCE TO RELATED APPLICATIONS

This application is a U.S. National Phase application under 35 U.S.C. §371 of PCT Application No. PCT/US2011/039040, filed 3 Jun. 2011, which claims priority from and the benefit of U.S. Provisional Application No. 61/352,593, filed Jun. 8, 2010.

FIELD OF THE INVENTION

The present invention relates to compounds which are inhibitors of the prolylcarboxy-peptidase (PrCP) enzyme and the use of such compounds to control, prevent and/or treat conditions or diseases mediated by prolylcarboxypeptidase activity. The compounds of the present invention are useful for the control, prevention and treatment of conditions and diseases related to abnormal metabolism, including obesity; diabetes; metabolic syndrome, obesity related disorders and diabetes related disorders.

BACKGROUND OF THE INVENTION

Obesity, which can be defined as a body weight more than 20% above the ideal body weight, is a major health concern in Western societies. It is estimated that about 97 million adults in the United States are overweight or obese. Obesity is the result of a positive energy balance, as a consequence of increased ratio of caloric intake to energy expenditure. Epidemiological studies have shown that increasing degrees of overweight and obesity are important predictors of decreased life expectancy. Obesity causes or exacerbates many health problems, both independently and in association with other diseases. The medical problems associated with obesity, which can be serious and life-threatening, include hypertension; type 2 diabetes mellitus; elevated plasma insulin concentrations; insulin resistance; dyslipidemias; hyperlipidemia; endometrial, breast, prostate and colon cancers; osteoarthritis; respiratory complications, such as obstructive sleep apnea; cholelithiasis; gallstones; arteriosclerosis; heart disease; abnormal heart rhythms; and heart arrythmias (Kopelman, P. G., Nature 404, 635-643 (2000)). Obesity is further associated with premature death and with a significant increase in mortality and morbidity from stroke, myocardial infarction, congestive heart failure, coronary heart disease, and sudden death.

Pro-opiomelanocortin (POMC) derived peptides are known to affect food intake. Several lines of evidence support the notion that the G-protein coupled receptors (GPCRs) of the melanocortin receptor (MC-R) family, several of which are expressed in the brain, are the targets of POMC derived peptides involved in the control of food intake and metabolism. A specific single MC-R that may be targeted for the control of obesity has not yet been identified, although evidence has been presented that MC-4R signalling is important in mediating feed behavior (S. Q. Giraudo et al., "Feeding effects of hypothalamic injection of melanocortin-4 receptor ligands," Brain Research, 80: 302-306 (1998)).

The prohormone pro-opiomelanocortin (POMC) plays a critical role in the regulations of energy metabolism, and is processed by proteases to produce several peptide hormones, including alpha-melanocyte-stimulating hormone (α-MSH or α-$MSH_{1-13}$). α-MSH is a major regulator of feeding and body weight homeostasis. Studies have shown that α-$MSH_{1-13}$ is a critical anorexigenic neuromodulator found in the hypothalamus, which inhibits food intake by binding target neurons expressing melanocortin receptors 3 and 4 (MC3R and MC4R) (see Vaisse et al., J. Clin. Invest., 106, 253-62 (2000); and Williams et al., Am. J. Physiol. Regul. Integr. Comp. Physiol., 289:R2-R3 (2005). MC-3R is expressed in the brain, gut, and placenta and may be involved in the control of food intake and thermogenesis. MC-4R is uniquely expressed in the brain, and its inactivation was shown to cause obesity (A. Kask, et al., "Selective antagonist for the melanocortin-4 receptor (HS014) increases food intake in free-feeding rats," Biochem. Biophys. Res. Commun., 245: 90-93 (1998)).

The enzyme prolylcarboxypeptidase (PRCP, Lysosomal Pro-X carboxypeptidase, angiotensinase C) is a serine protease that cleaves small, biologically active peptides at carboxyl termini linked to a penultimate proline group. α-MSH is a substrate of PRCP due to its C-terminal amino acid sequence, Pro-Val. Recent studies have shown that PRCP initiates the degradation of α-$MSH_{1-13}$ into inactive extracellular α-$MSH_{1-12}$, which is effective in reducing food intake and in regulating neuronal functions via melanocortin receptors. In overnight fasted animals, 2.5 ug of α-$MSH_{1-13}$ induced a 40% reduction in food intake relative to control animals, however, overnight fasted animals treated with 2.5 ug of α-$MSH_{1-12}$ did not significantly affect food intake compared to the controls. (Wallingford et al., J. Clinical Investigation, Vol. 119, No. 8, August 2009).

Further it has been shown that PRCP inhibition by small molecule protease inhibitors administered peripherally or centrally decreased food intake in wild type and genetically obese animals. Specifically, both the intracerebroventricular to rats and systemic administration to obese, leptin deficient mice of t-butyl carbamate-prolyl prolinal (BPP), which is an inhibitor of PRCP, resulted in a suppression of overnight food intake (Wallingford et al., J. Clinical Investigation, Vol. 119, No. 8, August 2009).

A recent study also showed that PrCP null mice had elevated hypothalamic levels of α-$MSH_{1-13}$ and were leaner compared with wild-type controls when fed regular chow, and were also resistant to high fat diet induced obesity. Specifically, on a high fat diet, PrCP gt/gt mice also showed a significant reduction in body weight and a reduction in food intake (Wallingford et al., J. Clinical Investigation, Vol. 119, No. 8, August 2009).

These studies suggest that PRCP inhibitors influence food intake and weight maintenance via melanocortin receptors and the control of active α-$MSH_{1-13}$ levels, and that targeting PRCP activity with central or peripheral administration of inhibitors can reduce food intake.

WO 2005/115446 discloses the role of prolylcarboxypeptidase inhibitors in weight control, control of body fat and food intake; and specific prolylcarboxypeptidase inhibitors, including t-butyl carbamate (BOC)-prolyl prolinal (BPP), N-benzyloxycarbonyl-prolyl-prolinal, diisopropyl fluorophosphates, PMSF, antipain, leupeptin, corn trypsin and mercuric chloride, useful to treat obesity and obesity related disorders. WO 2005/115446 also discloses the association of PRCP with hypertension, dyslipidemia, diabetes, stroke, gallbladder disease, cardiovascular disease, osteoarthritis, rheumatoid arthritis, hypercholesterolemia, angina, atherosclerosis, sleep apnea, respiratory problems, and cancer.

US 2008-0108080 discloses the utility of small molecule compounds with activity against the gene products encoded by PRCP for use in treating obesity.

WO 2007/140896 discloses the association of human PRCP with cardiovascular diseases, hematological diseases, neurological diseases and cancer based upon tissue distribution of PrCP.

The prolylcarboxypeptidase (PRCP) enzyme is disclosed in EP 1498424 and WO 2004/072265.

The present invention is concerned with novel spiroether compounds as inhibitors of prolylcarboxypeptidase which are useful in the treatment and/or prevention of various conditions and diseases mediated by prolylcarboxypeptidase activity including, but not limited to, abnormal metabolism, obesity, diabetes, metabolic syndrome, obesity and diabetes related disorders, such as hypertension, dyslipidemia, stroke, gallbladder disease, cardiovascular disease, osteoarthritis, rheumatoid arthritis, hypercholesterolemia, stable angina, unstable angina, artherosclerosis, sleep apnea, respiratory problems, cancer, stroke, hematological diseases and neurological diseases.

Weight loss drugs that are currently used to treat obesity have limited efficacy and significant side effects. Studies of the weight loss medications orlistat (Davidson, M. H. et al. (1999) JAMA 281:235-42), dexfenfluramine (Guy Grand, B. et al. (1989) Lancet 2:1142-5), sibutramine (Bray, G. A. et al. (1999) Obes. Res. &:189-98) and phentermine (Douglas, A. et al. (1983) Int. J. Obes. 7:591-5) have demonstrated a limited weight loss of about 5%-10% of body weight for drug compared to placebo. The side effects of these drugs and anti-obesity agents further limit their use. Dexfenfluramine was withdrawn from the market because of suspected heart valvulopathy; orlistal is limited by gastrointestinal side effects; the use of topiramate is limited by central nervous system effects; and the use of sibutramine is limited by its cardiovascular side effects which have led to reports of deaths and its withdrawal from the market in Italy. Obese patients generally respond well to surgical interventions that modify the gastrointestinal tract and limit food intake. However, one out of fifty bariatric surgery patients dies within the first 30 days post surgery, and 4.6% of bariatric surgery patients die within the first year (J. Amer. Med. Assoc., 2005, 294, 1903). Another study indicated that 33% of patients that undergo bariatric surgery have complications that require re-hospitalization within the first 6 months post operation (Medical Care, 2009, 47, 531).

There is a need for a weight loss treatment with enhanced efficacy, increased safety, and fewer undesirable side effects. The instant invention addresses this problem by providing prolylcarboxypeptidase inhibitors useful in the treatment and prevention of obesity, diabetes, and related disorders.

SUMMARY OF THE INVENTION

The present invention relates to compounds of structural formulas I-1 and 1-2:

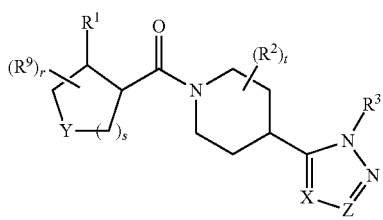
(I-1)

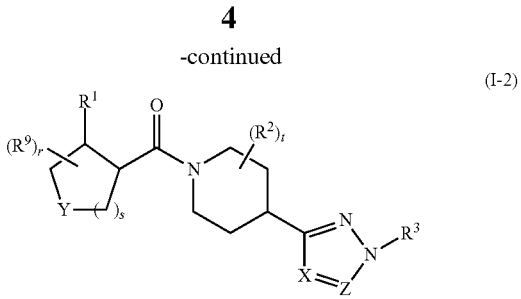
(I-2)

Compounds of formula I are inhibitors of prolylcarboxypeptidase (PrCP) and as such are useful in the treatment, control or prevention of diseases, disorders or conditions responsive to the modulation of the prolylcarboxypeptidase (PrCP) enzyme. In particular, the compounds of formula I act as inhibitors of the prolylcarboxypeptidase (PrCP) enzyme useful in the treatment, control or prevention of diseases, disorders or conditions responsive to the inhibition of prolylcarboxypeptidase (PrCP), such as eating disorders due to excessive food intake, and the resulting obesity and complications associated therewith, including diabetes, obesity related disorders and diabetes related disorders.

The present invention also relates to pharmaceutical compositions comprising the compounds of the present invention and a pharmaceutically acceptable carrier.

The present invention also relates to methods for the treatment, control, or prevention of disorders, diseases, or conditions responsive to inhibition of prolylcarboxypeptidase in a subject in need thereof by administering the compounds and pharmaceutical compositions of the present invention.

The present invention also relates to methods for the treatment, control, or prevention of obesity, Type 2 diabetes, metabolic syndrome, obesity related disorders and diabetes related disorders by administering the compounds and pharmaceutical compositions of the present invention.

DETAILED DESCRIPTION OF THE INVENTION

The present invention is concerned with compounds useful as inhibitors of prolylcarboxypeptidase. Compounds of the present invention are described by structural formulas I-1 and I-2:

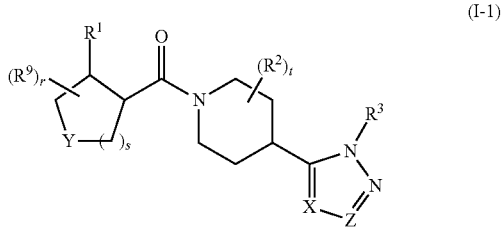
(I-1)

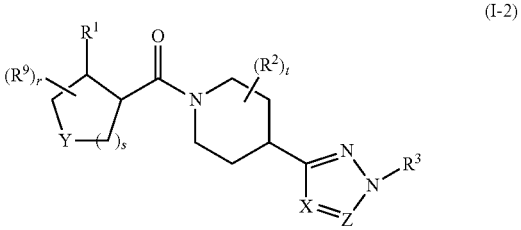
(I-2)

or a pharmaceutically acceptable salt thereof; wherein
X is independently selected from the group consisting of: N and $CR^8$;

Y is independently selected from the group consisting of: $NR^5$ or $CR^6R^7$;

Z is independently selected from the group consisting of: N and $CR^4$;

each $R^1$ is independently selected from the group consisting of:
 (1) —$(CH_2)_n$ $C_{3-7}$cycloalkyl,
 (2) —$(CH_2)_n$ $C_{2-6}$cycloheteroalkyl,
 (3) —$(CH_2)_n$ aryl, and
 (4) —$(CH_2)_n$ heteroaryl,
wherein each $CH_2$, cycloalkyl, cycloheteroalkyl, aryl, and heteroaryl is unsubstituted or substituted with one to three groups independently selected from $R^a$;

each $R^2$ is independently selected from the group consisting of:
 (1) hydrogen, and
 (2) —$C_{1-6}$ alkyl;

each $R^3$ is independently selected from the group consisting of:
 (1) —$C_{1-6}$ alkyl,
 (2) —$(CH_2)_m$ $C_{3-7}$cycloalkyl,
 (3) —$(CH_2)_m$ $C_{2-6}$cycloheteroalkyl,
 (4) —$(CH_2)_m$ aryl,
 (5) —$(CH_2)_m$ biphenyl, and
 (6) —$(CH_2)_m$ heteroaryl,
wherein each $CH_2$, alkyl, cycloalkyl, cycloheteroalkyl, aryl, biphenyl and heteroaryl is unsubstituted or substituted with one to four groups independently selected from Rb;

each $R^4$ is independently selected from the group consisting of:
 (1) hydrogen,
 (2) —$C_{1-6}$ alkyl,
 (3) —$(CH_2)_p CO_2H$,
 (4) —$(CH_2)_p CO_2 C_{1-6}$ alkyl,
 (5) —$(CH_2)_p COC_{1-6}$ alkyl,
 (6) —$(CH_2)_p$—$NR^h$—$C_{1-6}$ alkyl,
 (7) —$(CH_2)_p$—O—$C_{1-6}$ alkyl,
 (8) —$(CH_2)_p$—S—$C_{1-6}$ alkyl,
 (9) —$(CH_2)_p$ $C_{3-7}$cycloalkyl,
 (10) —$(CH_2)_p$ $C_{2-6}$cycloheteroalkyl,
 (11) —$(CH_2)_p$ aryl, and
 (12) —$(CH_2)_p$ heteroaryl,
wherein each $CH_2$, alkyl, cycloalkyl, cycloheteroalkyl, aryl and heteroaryl is unsubstituted or substituted with one to three groups independently selected from $R^c$;

each $R^5$ is independently selected from the group consisting of:
 (1) hydrogen,
 (2) —$C_{1-6}$ alkyl,
 (3) —$(CH_2)_q CO_2H$,
 (4) —$(CH_2)_q CO_2 C_{1-6}$ alkyl,
 (5) —$(CH_2)_q CO$—$C_{1-6}$ alkyl,
 (6) —$(CH_2)_q CO$—$C_{3-6}$ cycloalkyl,
 (7) —$(CH_2)_q CO$—$C_{2-6}$ cycloheteroalkyl,
 (8) —$(CH_2)_q CO$-aryl,
 (9) —$(CH_2)_q CO$-heteroaryl,
 (10) —$(CH_2)_u$—$NR^h$—$C_{1-6}$ alkyl,
 (11) —$(CH_2)_u$—O—$C_{1-6}$ alkyl,
 (12) —$(CH_2)_u$—S—$C_{1-6}$ alkyl,
 (13) —$(CH_2)_q C_{3-7}$cycloalkyl,
 (14) —$(CH_2)_q C_{2-6}$cycloheteroalkyl,
 (15) —$(CH_2)_q$aryl, and
 (16) —$(CH_2)_q$heteroaryl,
wherein each $CH_2$, alkyl, cycloalkyl, cycloheteroalkyl, aryl and heteroaryl is unsubstituted or substituted with one to three groups independently selected from $R^d$;

each $R^6$ is independently selected from the group consisting of:
 (1) hydrogen,
 (2) —$C_{1-6}$ alkyl,
 (3) —$(CH_2)_v CF_3$,
 (4) —$(CH_2)_v OCF_3$,
 (5) —$(CH_2)_v N(R^h)_2$,
 (6) —$(CH_2)_v CONH(C_{1-4}$ alkyl),
 (7) —$(CH_2)_v CON(C_{1-4}$ alkyl)$_2$,
 (8) —$(CH_2)_v$—$NR^h$—CO—$C_{1-4}$ alkyl,
 (9) —$(CH_2)_v$—$NR^h$—$CO_2$—$C_{1-4}$ alkyl,
 (10) —$(CH_2)_v$—$NR^h$—$(CH_2)_{0-2}$—$C_{3-6}$cycloalkyl,
 (11) —$(CH_2)_v$—$NR^h$—$(CH_2)_{0-2}$—$C_{2-6}$cycloheteroalkyl,
 (12) —$(CH_2)_v$—$NR^h$—$(CH_2)_{0-2}$-aryl,
 (13) —$(CH_2)_v$—$NR^h$—$(CH_2)_{0-2}$-heteroaryl,
 (14) —$(CH_2)_v$—$NR^h$—$(CH_2)_{1-2}$—O—$(CH_2)_{1-2}$—OH,
 (15) —$(CH_2)_v$—$NR^h$—$(CH_2)_{1-2}$—O—$(CH_2)_{1-2}$—$OC_{1-6}$ alkyl,
 (16) —$(CH_2)_v$—S—$C_{1-4}$ alkyl,
 (17) —$(CH_2)_v$—$SO_2 C_{1-4}$ alkyl,
 (18) —$(CH_2)_v$—$SO_2$-phenyl,
 (19) —$(CH_2)_v$—$NR^h$—$SO_2 C_{1-4}$ alkyl,
 (20) —$(CH_2)_v$—$NR^h$—$SO_2$-phenyl,
 (21) —$(CH_2)_v C_{3-7}$cycloalkyl,
 (22) —$(CH_2)_v C_{2-6}$cycloheteroalkyl,
 (23) —$(CH_2)_v$aryl, and
 (24) —$(CH_2)_v$heteroaryl,
wherein each $CH_2$, alkyl, cycloalkyl, cycloheteroalkyl, phenyl, aryl and heteroaryl is unsubstituted or substituted with one to three substituents selected from $R^e$;

each $R^7$ is independently selected from the group consisting of:
 (1) hydrogen, and
 (2) —$C_{1-6}$ alkyl,
wherein alkyl is unsubstituted or substituted with one to three substituents selected from $R^f$;

each $R^8$ is independently selected from the group consisting of
 (1) hydrogen, and
 (2) —$C_{1-6}$ alkyl;

each $R^9$ is independently selected from the group consisting of:
 (1) hydrogen, and
 (2) —$C_{1-6}$ alkyl;
wherein alkyl is unsubstituted or substituted with one to three substituents selected from $R^g$ each $R^a$ is independently selected from the group consisting of:
 (1) halogen,
 (2) —CN,
 (3) —OH,
 (4) —$C_{1-6}$alkyl,
 (5) —$OC_{1-6}$alkyl,
 (6) —$CF_3$, and
 (7) —$OCF_3$;

each $R^b$ is independently selected from the group consisting of:
 (1) halogen,
 (2) —CN,
 (3) —OH,
 (4) —$C_{1-6}$alkyl,
 (5) —$OC_{1-6}$alkyl,
 (6) —$CF_3$, and
 (7) —$OCF_3$;

each $R^c$ is independently selected from the group consisting of:
 (1) halogen, and
 (2) —$C_{1-6}$ alkyl;

each $R^d$ is independently selected from the group consisting of
- (1) halogen,
- (2) —CN,
- (3) —OH,
- (4) —$C_{1-6}$alkyl,
- (5) —$OC_{1-6}$alkyl,
- (6) —$CF_3$,
- (7) —$OCF_3$, and
- (8) —$C(O)C_{1-6}$alkyl;

each $R^e$ is independently selected from the group consisting of:
- (1) hydrogen,
- (2) halogen,
- (3) —CN,
- (4) —OH,
- (5) —$C_{1-6}$alkyl,
- (6) —$OC_{1-6}$alkyl,
- (7) —$CF_3$,
- (8) —$OCF_3$, and
- (9) —$C_{3-6}$ cycloalkyl;

each $R^f$ is independently selected from the group consisting of:
- (1) hydrogen,
- (2) halogen, and
- (3) $C_{1-6}$ alkyl;

each $R^g$ is independently selected from the group consisting of:
- (1) hydrogen,
- (2) halogen, and
- (3) $C_{1-6}$ alkyl;

each $R^h$ is independently selected from the group consisting of:
- (1) hydrogen, and
- (2) $C_{1-6}$ alkyl;

m is selected from 0, 1, 2, and 3;
n is selected from 0, 1, 2, and 3;
p is selected from 0, 1, 2, and 3;
q is selected from 0, 1, 2, and 3;
r is selected from 0, 1 and 2;
s is selected from 1 and 2;
t is selected from 0, 1, 2, and 3;
u is 1, 2, or 3; and
v is selected from 0, 1, 2, and 3.

In one embodiment of the present invention, X is independently selected from the group consisting of: N and $CR^8$. In a class of this embodiment, X is independently selected from the group consisting of N and CH. In another class of this embodiment, X is N. In another class of this embodiment, X is $CR^8$.

In another embodiment of the present invention, Y is independently selected from the group consisting of: $NR^5$ or $CR^6R^7$. In a class of this embodiment, Y is $NR^5$. In another class of this embodiment, Y is $CR^6R^7$.

In another embodiment of the present invention, Z is independently selected from the group consisting of: N and $CR^4$. In a class of this embodiment, Z is N. In another class of this embodiment, Z is $CR^4$.

In another embodiment of the present invention, each $R^1$ is independently selected from the group consisting of: —$(CH_2)_n$ $C_{3-7}$cycloalkyl, —$(CH_2)_n$ $C_{2-6}$cycloheteroalkyl, —$(CH_2)_n$ aryl, and —$(CH_2)_n$ heteroaryl, wherein each $CH_2$, cycloalkyl, cycloheteroalkyl, aryl, and heteroaryl is unsubstituted or substituted with one to three groups independently selected from $R^a$.

In a class of this embodiment, each $R^1$ is independently selected from the group consisting of: —$(CH_2)_n$ aryl, and —$(CH_2)_n$ heteroaryl, wherein each $CH_2$, aryl and heteroaryl is unsubstituted or substituted with one to three groups independently selected from $R^a$. In a subclass of this class, each $R^1$ is independently selected from the group consisting of —$(CH_2)_n$ phenyl, and —$(CH_2)_n$ pyridine, wherein each $CH_2$, phenyl and pyridine is unsubstituted or substituted with one to three groups independently selected from $R^a$. In another subclass of this class, each $R^1$ is independently selected from the group consisting of: -phenyl and -pyridine, wherein each phenyl and pyridine is unsubstituted or substituted with one to three groups independently selected from $R^a$.

In another class of this embodiment, each $R^1$ is independently selected from the group consisting of —$(CH_2)_n$ aryl, wherein each $CH_2$ and aryl is unsubstituted or substituted with one to three groups independently selected from $R^a$. In a subclass of this class, each $R^1$ is independently selected from the group consisting of: —$(CH_2)_n$ phenyl, wherein each $CH_2$ and phenyl is unsubstituted or substituted with one to three groups independently selected from $R^a$. In another subclass of this class, each $R^1$ is aryl, wherein aryl is unsubstituted or substituted with one to three groups independently selected from $R^a$. In another subclass of this class, each $R^1$ is phenyl, wherein phenyl is unsubstituted or substituted with one to three groups independently selected from $R^a$. In another class of this embodiment, $R^1$ is phenyl, wherein phenyl is unsubstituted or substituted with one to three groups independently selected from $R^a$.

In another embodiment of the present invention, each $R^2$ is independently selected from the group consisting of: hydrogen, and —$C_{1-6}$ alkyl. In a class of this embodiment, each $R^2$ is hydrogen. In another class of this embodiment, each $R^2$ is —$C_{1-6}$ alkyl.

In another embodiment of the present invention, each $R^3$ is independently selected from the group consisting of: —$C_{1-6}$ alkyl, —$(CH_2)_m$ $C_{3-7}$cycloalkyl, —$(CH_2)_m$ $C_{2-6}$cycloheteroalkyl, —$(CH_2)_m$ aryl, —$(CH_2)_m$ biphenyl, and —$(CH_2)_m$ heteroaryl, wherein each $CH_2$, alkyl, cycloalkyl, cycloheteroalkyl, aryl, biphenyl and heteroaryl is unsubstituted or substituted with one to four groups independently selected from $R^b$. In a class of this embodiment, each $R^3$ is independently selected from the group consisting of: —$C_{1-6}$ alkyl, —$(CH_2)_m$ $C_{3-7}$cycloalkyl, —$(CH_2)_m$ aryl, —$(CH_2)_m$ biphenyl, and —$(CH_2)_m$ heteroaryl, wherein each $CH_2$, cycloalkyl, cycloheteroalkyl, aryl, biphenyl and heteroaryl is unsubstituted or substituted with one to three groups independently selected from $R^b$. In a subclass of this class, each $R^3$ is independently selected from the group consisting of: —$C(CH_3)_3$, cyclohexyl, phenyl, —$CH_2$-phenyl, biphenyl, and pyridine, wherein each $CH_2$, alkyl, cyclohexyl, phenyl, biphenyl and pyridine is unsubstituted or substituted with one to three groups independently selected from $R^b$.

In another class of this embodiment, each $R^3$ is independently selected from the group consisting of: —$(CH_2)_m$ aryl, wherein each $CH_2$ and aryl is unsubstituted or substituted with one to three groups independently selected from $R^b$. In a subclass of this class, each $R^3$ is independently selected from the group consisting of: phenyl, and —$CH_2$-phenyl, wherein each $CH_2$ and phenyl is unsubstituted or substituted with one to three groups independently selected from $R^b$. In another subclass of this class, each $R^3$ is phenyl, wherein phenyl is unsubstituted or substituted with one to three groups independently selected from $R^b$.

In another embodiment of the present invention, each $R^4$ is independently selected from the group consisting of: hydrogen, —$C_{1-6}$ alkyl, —$(CH_2)_p CO_2H$, —$(CH_2)_p CO_2 C_{1-6}$ alkyl, —(CH$_2$)$_p$COC$_{1-6}$ alkyl, —(CH$_2$)$_p$—NR$^h$—C$_{1-6}$ alkyl, —(CH$_2$)$_p$—O—C$_{1-6}$ alkyl, —(CH$_2$)$_p$—S—C$_{1-6}$ alkyl, —(CH$_2$)$_p$ C$_{3-7}$cycloalkyl, —(CH$_2$)$_p$ C$_{2-6}$cycloheteroalkyl, —(CH$_2$)$_p$ aryl, and —(CH$_2$)$_p$ heteroaryl, wherein each CH$_2$, alkyl, cycloalkyl, cycloheteroalkyl, aryl and heteroaryl is unsubstituted or substituted with one to three groups independently selected from R$^c$. In a class of this embodiment, each R$^4$ is independently selected from the group consisting of: hydrogen, —C$_{1-6}$ alkyl, —(CH$_2$)$_p$ aryl, and —(CH$_2$)$_p$ heteroaryl, wherein each CH$_2$, alkyl, aryl and heteroaryl is unsubstituted or substituted with one to three groups independently selected from R$^c$. In a subclass of this class, each R$^4$ is independently selected from the group consisting of: hydrogen, —CH$_3$, —CF$_3$, phenyl, pyridine, and pyrazine, wherein each alkyl, phenyl and heteroaryl is unsubstituted or substituted with one to three groups independently selected from R$^c$. In another subclass of this class, each R$^4$ is independently selected from the group consisting of: hydrogen, —CH$_3$ and pyridine, wherein each alkyl and pyridine is unsubstituted or substituted with one to three groups independently selected from R$^c$. In another class of this embodiment, each R$^4$ is independently selected from the group consisting of: hydrogen, —C$_{1-6}$ alkyl, and —(CH$_2$)$_p$ heteroaryl, wherein each CH$_2$, alkyl and heteroaryl is unsubstituted or substituted with one to three groups independently selected from R$^c$. In a subclass of this class, each R$^4$ is independently selected from the group consisting of: hydrogen, —C$_{1-6}$ alkyl, and heteroaryl, wherein each CH$_2$, alkyl and heteroaryl is unsubstituted or substituted with one to three groups independently selected from R$^c$. In another subclass of this class, each R$^4$ is independently selected from the group consisting of: hydrogen, —CH$_3$, —CF$_3$, pyridine and pyrazine, wherein each alkyl and heteroaryl is unsubstituted or substituted with one to three groups independently selected from R$^c$. In another class of this embodiment, each R$^4$ is independently selected from the group consisting of: —C$_{1-6}$ alkyl, wherein each alkyl is unsubstituted or substituted with one to three groups independently selected from R$^c$. In a subclass of this class, each R$^4$ is independently selected from the group consisting of: —CH$_3$ and —CF$_3$. In another subclass of this class, each R$^4$ is —CH$_3$.

In another subclass of this class, each R$^4$ is independently selected from the group consisting of: hydrogen, and —C$_{1-6}$ alkyl, wherein alkyl is unsubstituted or substituted with one to three groups independently selected from R$^c$. In another subclass of this class, each R$^4$ is independently selected from the group consisting of: hydrogen, and —CH$_3$, wherein —CH$_3$ is unsubstituted or substituted with one to three groups independently selected from R$^c$.

In another embodiment of the present invention, each R$^5$ is independently selected from the group consisting of: hydrogen, —C$_{1-6}$ alkyl, —(CH$_2$)$_q$CO$_2$H, —(CH$_2$)$_q$CO$_2$C$_{1-6}$ alkyl, —(CH$_2$)$_q$CO—C$_{1-6}$ alkyl, —(CH$_2$)$_q$CO—C$_{3-6}$ cycloalkyl, —(CH$_2$)$_q$CO—C$_{2-6}$ cycloheteroalkyl, —(CH$_2$)$_q$CO-aryl, —(CH$_2$)$_q$CO-heteroaryl, —(CH$_2$)$_u$—NR$^h$—C$_{1-6}$ alkyl, —(CH$_2$)$_u$—O—C$_{1-6}$ alkyl, —(CH$_2$)$_u$—S—C$_{1-6}$ alkyl, —(CH$_2$)$_q$C$_{3-7}$cycloalkyl, —(CH$_2$)$_q$C$_{2-6}$cycloheteroalkyl, —(CH$_2$)$_q$aryl, and —(CH$_2$)$_q$heteroaryl, wherein each CH$_2$, alkyl, cycloalkyl, cycloheteroalkyl, aryl and heteroaryl is unsubstituted or substituted with one to three groups independently selected from R$^d$. In a class of this embodiment, each R$^5$ is independently selected from the group consisting of: hydrogen, —C$_{1-6}$ alkyl, —(CH$_2$)$_q$CO$_2$C$_{1-6}$ alkyl, —(CH$_2$)$_q$CO—C$_{1-6}$ alkyl, —(CH$_2$)$_q$CO—C$_{3-6}$ cycloalkyl, —(CH$_2$)$_q$CO—C$_{2-6}$ cycloheteroalkyl, —(CH$_2$)$_q$C$_{3-7}$cycloalkyl, —(CH$_2$)$_q$C$_{2-6}$cycloheteroalkyl, —(CH$_2$)$_q$aryl, and —(CH$_2$)$_q$heteroaryl, wherein each CH$_2$, alkyl, cycloalkyl, cycloheteroalkyl, aryl and heteroaryl is unsubstituted or substituted with one to three groups independently selected from R$^d$. In a subclass of this class, each R$^5$ is independently selected from the group consisting of: hydrogen, —C(CH$_3$)$_3$, —CH$_2$C(CH$_3$)$_3$, —(CH$_2$)$_2$CH$_3$, —(CH$_2$)$_2$CF$_3$, —CH$_2$CF$_3$, —CH(CH$_3$)CHF$_2$, —CH$_2$CH$_2$F, —CH(CH$_3$)$_2$, —CO$_2$C(CH$_3$)$_3$, —CO$_2$CH$_3$, —COCH$_3$, —CO-cyclohexyl, —CO-piperidine, cyclopentyl, cyclobutyl, tetrahydropyran, piperidine, —(CH$_2$)$_2$-phenyl, —CH$_2$-phenyl, —CH(CH$_3$)-phenyl, —CH$_2$-heteroaryl, heteroaryl, —CH$_2$-pyridine, pyridine, —CH$_2$-imidazole, pyrimidine, —CH$_2$-pyrazole, —CH$_2$-thiazole, —CH$_2$-pyrazine, —CH$_2$-pyridazine, and —CH$_2$-triazole, wherein each CH$_2$, alkyl, cycloalkyl, cycloheteroalkyl, aryl and heteroaryl is unsubstituted or substituted with one to three groups independently selected from R$^d$.

In another class of this embodiment, each R$^5$ is independently selected from the group consisting of: hydrogen, —C$_{1-6}$ alkyl, and —(CH$_2$)$_q$heteroaryl, wherein each CH$_2$, alkyl and heteroaryl is unsubstituted or substituted with one to three groups independently selected from R$^d$. In a subclass of this class, each R$^5$ is independently selected from the group consisting of: hydrogen, —C(CH$_3$)$_3$, —CH$_2$C(CH$_3$)$_3$, —(CH$_2$)$_2$CF$_3$, —(CH$_2$)$_2$CF$_3$, —CH$_2$CF$_3$, —CH(CH$_3$)CHF$_2$, —CH$_2$CH$_2$F, —CH(CH$_3$)$_2$, —CH$_2$-heteroaryl, heteroaryl, —CH$_2$-pyridine, pyridine, —CH$_2$-imidazole, pyrimidine, —CH$_2$-pyrazole, —CH$_2$-thiazole, —CH$_2$-pyrazine, —CH$_2$-pyridazine, and —CH$_2$-triazole, wherein each CH$_2$, alkyl and heteroaryl is unsubstituted or substituted with one to three groups independently selected from R$^d$.

In another class of this embodiment, each R$^5$ is independently selected from the group consisting of: —(CH$_2$)$_q$heteroaryl, wherein each CH$_2$ and heteroaryl is unsubstituted or substituted with one to three groups independently selected from R$^d$. In a subclass of this class, each R$^5$ is independently selected from the group consisting of: —CH$_2$-heteroaryl, and heteroaryl, wherein each CH$_2$ and heteroaryl is unsubstituted or substituted with one to three groups independently selected from R$^d$. In another subclass of this class, each R$^5$ is independently selected from the group consisting of: —CH$_2$-pyridine, pyridine, —CH$_2$-imidazole, pyrimidine, —CH$_2$-pyrazole, —CH$_2$-thiazole, —CH$_2$-pyrazine, —CH$_2$-pyridazine, —CH$_2$-triazole, wherein each CH$_2$ and heteroaryl is unsubstituted or substituted with one to three groups independently selected from R$^d$. In another subclass of this class, each R$^5$ is pyridine, wherein pyridine is unsubstituted or substituted with one to three groups independently selected from R$^d$. In another class of this embodiment, R$^5$ is independently selected from the group consisting of: hydrogen and —C$_{1-6}$ alkyl, wherein each alkyl is unsubstituted or substituted with one to three groups independently selected from R$^d$. In a subclass of this class, R$^5$ is independently selected from the group consisting of: hydrogen and —C(CH$_3$)$_3$, wherein each alkyl is unsubstituted or substituted with one to three groups independently selected from R$^d$.

In another embodiment of the present invention, each R$^6$ is independently selected from the group consisting of: hydrogen, —C$_{1-6}$ alkyl, —(CH$_2$)$_v$CF$_3$, —(CH$_2$)$_v$OCF$_3$, —(CH$_2$)$_v$N(R$^h$)$_2$, —(CH$_2$)$_v$CONH(C$_{1-4}$ alkyl), —(CH$_2$)$_v$CON(C$_{1-4}$ alkyl)$_2$, —(CH$_2$)$_v$—NR$^h$—CO—C$_{1-4}$ alkyl, —(CH$_2$)$_v$—NR$^h$—CO$_2$—C$_{1-4}$ alkyl, —(CH$_2$)$_v$—NR$^h$—(CH$_2$)$_{0-2}$—C$_{3-6}$ cycloalkyl, —(CH$_2$)$_v$—NR$^h$—(CH$_2$)$_{0-2}$—C2-6cycloheteroalkyl, —(CH$_2$)$_v$—NR$^h$—(CH$_2$)$_{0-2}$-aryl, —(CH$_2$)$_v$—NR$^h$—(CH$_2$)$_{0-2}$-heteroaryl, —(CH$_2$)$_v$—NR$^h$—(CH$_2$)$_{1-2}$—O—(CH$_2$)$_{1-2}$—OH, —(CH$_2$)$_v$—NR$^h$—(CH$_2$)$_{1-2}$—O—(CH$_2$)$_{1-2}$OC$_{1-6}$ alkyl, —(CH$_2$)$_v$—S—C$_{1-4}$ alkyl, —(CH$_2$)$_v$—SO$_2$C$_{1-4}$ alkyl, —(CH$_2$)$_v$—SO$_2$-phenyl, —(CH$_2$)$_v$—NR$^h$—SO$_2$C$_{1-4}$ alkyl, —(CH$_2$)$_v$—NR$^h$—SO$_2$phenyl, —(CH$_2$)$_v$-

$C_{3-7}$cycloalkyl, —(CH$_2$)$_v$C$_{2-6}$cycloheteroalkyl, —(CH$_2$)$_v$aryl, and —(CH$_2$)$_v$heteroaryl, wherein each CH$_2$, alkyl, cycloalkyl, cycloheteroalkyl, phenyl, aryl and heteroaryl is unsubstituted or substituted with one to three substituents selected from R$^e$.

In a class of this embodiment, each R$^6$ is independently selected from the group consisting of: —(CH$_2$)$_v$N(R$^h$)$_2$, —(CH$_2$)$_v$—NR$^h$—CO—C$_{1-4}$ alkyl, —(CH$_2$)$_v$—NR$^h$—CO$_2$—C$_{1-4}$ alkyl, —(CH$_2$)$_v$—NR$^h$—(CH$_2$)$_{0-2}$—C$_{3-6}$cycloalkyl, —(CH$_2$)$_v$—NR$^h$—(CH$_2$)$_{0-2}$-aryl, —(CH$_2$)$_v$—NR$^h$—(CH$_2$)$_{1-2}$—O—(CH$_2$)$_{1-2}$—OH, —(CH$_2$)$_v$—NR$^h$—(CH$_2$)$_{1-2}$—O—(CH$_2$)$_{1-2}$—OC$_{1-6}$ alkyl, —(CH$_2$)$_v$—NR$^h$—SO$_2$C$_{1-4}$ alkyl, and —(CH$_2$)$_v$C$_{2-6}$cycloheteroalkyl, wherein each CH$_2$, alkyl, cycloalkyl, cycloheteroalkyl, phenyl and aryl is unsubstituted or substituted with one to three substituents selected from R$^e$. In a subclass of this class, each R$^6$ is independently selected from the group consisting of: —NH$_2$, —NHC(CH$_3$)$_3$, —NHCH$_3$, —N(CH$_3$)$_2$, —N(CH$_3$)CH$_2$CF$_3$, —NH(CH$_2$)$_2$CF$_3$, —N(CH$_3$)(CH$_2$)$_2$CF$_3$, —NH(CH$_2$)$_2$F, —N(CH$_3$)—(CH$_2$)$_2$F, —N(CH$_3$)—CH$_2$CF$_2$, —N(CH$_3$)COCH$_3$, —N(CH$_3$)CO$_2$C(CH$_3$)$_3$, NHCO$_2$C(CH$_3$)$_3$, —NH-cyclobutyl, —NHCH(CH$_3$)-phenyl, —N(CH$_3$)—CH(CH$_3$)-phenyl, —NH—C(CH$_3$)$_2$-phenyl, —NH(CH$_2$)$_2$—O—(CH$_2$)$_2$—OH, —NH(CH$_2$)$_2$—O—CH$_3$, —N(CH$_3$)—(CH$_2$)$_2$—O—CH$_3$, —N(CH$_3$)—SO$_2$CH$_3$, morpholine, pyrrolidine, and 6-oxa-3-azabicyclo[2.2.1]heptane, wherein each CH$_2$, alkyl, cycloalkyl, cycloheteroalkyl, phenyl and aryl is unsubstituted or substituted with one to three substituents selected from R$^e$.

In another class of this embodiment, each R$^6$ is independently selected from the group consisting of: —(CH$_2$)$_v$N(R$^h$)$_2$, —(CH$_2$)$_v$—NR$^h$—(CH$_2$)$_{0-2}$—C3-6cycloalkyl, —(CH$_2$)$_v$—NR$^h$—(CH$_2$)$_{0-2}$-aryl, —(CH$_2$)$_v$—NR$^h$—(CH$_2$)$_{1-2}$—O—(CH$_2$)$_{1-2}$—OH, —(CH$_2$)$_v$—NR$^h$—(CH$_2$)$_{1-2}$—O—(CH$_2$)$_{1-2}$—OC$_{1-6}$ alkyl, and —(CH$_2$)$_v$C$_{2-6}$cycloheteroalkyl, wherein each CH$_2$, alkyl, cycloalkyl, cycloheteroalkyl and aryl is unsubstituted or substituted with one to three substituents selected from R$^e$. In a subclass of this class, each R$^6$ is independently selected from the group consisting of: —NH$_2$, —NHC(CH$_3$)$_3$, —NHCH$_3$, —N(CH$_3$)$_2$, —N(CH$_3$)CH$_2$CF$_3$, —NH(CH$_2$)$_2$CF$_3$, —N(CH$_3$)(CH$_2$)$_2$CF$_3$, —NH(CH$_2$)$_2$F, —N(CH$_3$)—(CH$_2$)$_2$F, —N(CH$_3$)—CH$_2$CF$_2$, —NH-cyclobutyl, —NHCH(CH$_3$)-phenyl, —N(CH$_3$)—CH(CH$_3$)-phenyl, —NH—C(CH$_3$)$_2$-phenyl, —NH(CH$_2$)$_2$—O—(CH$_2$)$_2$—OH, —NH(CH$_2$)$_2$—O—CH$_3$, —N(CH$_3$)—(CH$_2$)$_2$—O—CH$_3$, morpholine, pyrrolidine, and 6-oxa-3-azabicyclo[2.2.1]heptane, wherein each CH$_2$, alkyl, cycloalkyl, cycloheteroalkyl and phenyl is unsubstituted or substituted with one to three substituents selected from R$^e$.

In another class of this embodiment, each R$^6$ is independently selected from the group consisting of: —(CH$_2$)$_v$N(R$^h$)$_2$, —(CH$_2$)$_v$—NR$^h$—(CH$_2$)$_{0-2}$—C3-6cycloalkyl, —(CH$_2$)$_v$—NR$^h$—(CH$_2$)$_{0-2}$-aryl, —(CH$_2$)$_v$—NR$^h$—(CH$_2$)$_{1-2}$—O—(CH$_2$)$_{1-2}$—OC$_{1-6}$ alkyl, and —(CH$_2$)$_v$C$_{2-6}$cycloheteroalkyl, wherein each CH$_2$, alkyl, cycloalkyl, cycloheteroalkyl and aryl is unsubstituted or substituted with one to three substituents selected from R$^e$. In a subclass of this class, each R$^6$ is independently selected from the group consisting of: —NH$_2$, —NHC(CH$_3$)$_3$, —NHCH$_3$, —N(CH$_3$)$_2$, —N(CH$_3$)CH$_2$CF$_3$, —NH(CH$_2$)$_2$CF$_3$, —N(CH$_3$)(CH$_2$)$_2$CF$_3$, —NH(CH$_2$)$_2$F, —N(CH$_3$)—(CH$_2$)$_2$F, N(CH$_3$)—CH$_2$CF$_2$, —NH-cyclobutyl, —NHCH(CH$_3$)-phenyl, —N(CH$_3$)—CH(CH$_3$)-phenyl, —NH—C(CH$_3$)$_2$-phenyl, —NH(CH$_2$)$_2$—O—CH$_3$, —N(CH$_3$)—(CH$_2$)$_2$—O—CH$_3$, morpholine, and pyrrolidine, wherein each CH$_2$, alkyl, cycloalkyl, cycloheteroalkyl and phenyl is unsubstituted or substituted with one to three substituents selected from R$^e$.

In another class of this embodiment, each R$^6$ is independently selected from the group consisting of: —(CH$_2$)$_v$N(R$^h$)$_2$, —(CH$_2$)$_v$—NR$^h$—(CH$_2$)$_{1-2}$—O—(CH$_2$)$_{1-2}$—OH, and —(CH$_2$)$_v$C$_{2-6}$cycloheteroalkyl, wherein each CH$_2$, alkyl and cycloheteroalkyl is unsubstituted or substituted with one to three substituents selected from R$^e$. In a subclass of this class, each R$^6$ is independently selected from the group consisting of: —NH$_2$, —NHC(CH$_3$)$_3$, —NHCH$_3$, —N(CH$_3$)$_2$, —N(CH$_3$)CH$_2$CF$_3$, —NH(CH$_2$)$_2$CF$_3$, —N(CH$_3$)(CH$_2$)$_2$CF$_3$, —NH(CH$_2$)$_2$F, —N(CH$_3$)—(CH$_2$)$_2$F, N(CH$_3$)—CH$_2$CF$_2$, —NH(CH$_2$)$_2$—O—(CH$_2$)$_2$—OH, -morpholine, pyrrolidine, and 6-oxa-3-azabicyclo[2.2.1]heptane, wherein each CH$_2$, alkyl and cycloheteroalkyl is unsubstituted or substituted with one to three substituents selected from R$^e$. In another subclass of this class, each R$^6$ is independently selected from the group consisting of: —NH$_2$, —N(CH$_3$)$_2$, —NH(CH$_2$)$_2$CF$_3$, —NH(CH$_2$)$_2$—O—(CH$_2$)$_2$—OH, and -morpholine, wherein each CH$_2$, alkyl and cycloheteroalkyl is unsubstituted or substituted with one to three substituents selected from R$^e$.

In another class of this embodiment, R$^6$ is independently selected from the group consisting of: —(CH$_2$)$_v$N(R$^h$)$_2$, and —(CH$_2$)$_v$C$_{2-6}$cycloheteroalkyl, wherein each CH$_2$, alkyl and cycloheteroalkyl is unsubstituted or substituted with one to three substituents selected from R$^e$. In a subclass of this class, each R$^6$ is independently selected from the group consisting of: —NH$_2$, —NHC(CH$_3$)$_3$, —NHCH$_3$, —N(CH$_3$)$_2$, —N(CH$_3$)CH$_2$CF$_3$, —NH(CH$_2$)$_2$CF$_3$, —N(CH$_3$)(CH$_2$)$_2$CF$_3$, —NH(CH$_2$)$_2$F, —N(CH$_3$)—(CH$_2$)$_2$F, —N(CH$_3$)—CH$_2$CF$_2$, -morpholine, and pyrrolidine, wherein each CH$_2$, alkyl and cycloheteroalkyl is unsubstituted or substituted with one to three substituents selected from R$^e$. In a subclass of this class, each R$^6$ is independently selected from the group consisting of: —NH$_2$, —NHCH$_3$, —N(CH$_3$)$_2$, —N(CH$_3$)(CH$_2$)$_2$CF$_3$, -morpholine, and pyrrolidine, wherein each CH$_2$, alkyl and cycloheteroalkyl is unsubstituted or substituted with one to three substituents selected from R$^e$.

In another embodiment of the present invention, each R$^7$ is independently selected from the group consisting of: hydrogen, and —C$_{1-6}$ alkyl, wherein alkyl is unsubstituted or substituted with one to three substituents selected from R$^1$. In a class of this embodiment, each R$^7$ is hydrogen. In another class of this embodiment, each R$^7$ is —C$_{1-6}$ alkyl, wherein alkyl is unsubstituted or substituted with one to three substituents selected from R$^f$. In a subclass of this class, each R$^7$ is —CH$_3$.

In another embodiment of the present invention, each R$^8$ is independently selected from the group consisting of: hydrogen, and —C$_{1-6}$ alkyl. In a class of this embodiment, each R$^8$ is hydrogen. In another class of this embodiment, each R$^8$ is —C$_{1-6}$ alkyl.

In another embodiment of the present invention, each R$^9$ is independently selected from the group consisting of: hydrogen, and —C$_{1-6}$ alkyl; wherein alkyl is unsubstituted or substituted with one to three substituents selected from R$^g$ In a class of this embodiment, each R$^9$ is hydrogen. In another class of this embodiment, each R$^9$ is —C$_{1-6}$ alkyl, wherein alkyl is unsubstituted or substituted with one to three substituents selected from R$^g$.

In another embodiment of the present invention, each R$^a$ is independently selected from the group consisting of: halogen, —CN, —OH, —C$_{1-6}$alkyl, —OC$_{1-6}$alkyl, —CF$_3$, and —OCF$_3$. In a class of this embodiment, each R$^a$ is independently selected from the group consisting of: F, Cl, Br, —CN, —OH, —CH$_3$, —OCH$_3$, —CF$_3$, and —OCF$_3$. In another class of this embodiment, each R$^a$ is independently selected from the group consisting of: halogen, —C$_{1-6}$alkyl, —OC$_{1-6}$alkyl, —CF$_3$, and —OCF$_3$. In a subclass of this class, each R$^a$ is independently selected from the group consisting of: F, Cl, Br, —CH$_3$, —OCH$_3$, —CF$_3$, and —OCF$_3$. In another class of this embodiment, each R$^a$ is independently selected from the group consisting of: halogen, —C$_{1-6}$alkyl, and —OC$_{1-6}$alkyl. In another class of this embodiment, each R$^a$ is independently selected from the group consisting of: F, Cl, Br, —CH$_3$, and —OCH$_3$. In another class of this embodiment, each R$^a$ is independently selected from the group consisting of: halogen. In a subclass of this class, each R$^a$ is independently selected from the group consisting of: F, Cl, and Br. In another subclass of this class, each R$^a$ is independently selected from the group consisting of: F, and Cl. In another subclass of this class, each R$^a$ is F. In another subclass of this class, each R$^a$ is Cl.

In another embodiment of the present invention, each R$^b$ is independently selected from the group consisting of: halogen, —CN, —OH, —C$_{1-6}$alkyl, —OC$_{1-6}$alkyl, —CF$_3$, and —OCF$_3$. In a class of this embodiment, each R$^b$ is independently selected from the group consisting of: F, Cl, CN, —OH, —CH$_3$, —OCH$_3$, —CF$_3$, and —OCF$_3$. In another class of this embodiment, each R$^b$ is independently selected from the group consisting of: halogen, —CN, —C$_{1-6}$alkyl, —OC$_{1-6}$alkyl, CF$_3$, and —OCF$_3$. In a subclass of this class, each R$^b$ is independently selected from the group consisting of: F, Cl, —CN, —CH$_3$, —OCH$_3$, —CF$_3$, and —OCF$_3$. In another class of this embodiment, each R$^b$ is independently selected from the group consisting of: halogen. In a subclass of this class, each R$^b$ is independently selected from the group consisting of: F, and Cl. In another subclass of this class, R$^b$ is F. In another subclass of this class, R$^b$ is Cl.

In another embodiment of the present invention, each R$^c$ is independently selected from the group consisting of: halogen, and —C$_{1-6}$ alkyl. In a class of this embodiment, each R$^c$ is halogen. In a subclass of this class, R$^c$ is fluoro. In another class of this embodiment, each R$^c$ is —C$_{1-6}$ alkyl. In a subclass of this class, each R$^c$ is —CH$_3$.

In another embodiment of the present invention, each R$^d$ is independently selected from the group consisting of: halogen, —CN, —OH, —C$_{1-6}$alkyl, —OC$_{1-6}$alkyl, —CF$_3$, —OCF$_3$, and —C(O)C$_{1-6}$alkyl. In a class of this embodiment, each R$^d$ is independently selected from the group consisting of: F, Cl, —CN, —OH, —CH$_3$, —CH$_2$CH$_3$, —OCH$_2$CH$_3$, —CF$_3$, —OCF$_3$, and —C(O)CH$_3$. In another class of this embodiment, each R$^d$ is independently selected from the group consisting of halogen, —C$_{1-6}$alkyl, —OC$_{1-6}$alkyl, —CF$_3$, —OCF$_3$, and —C(O)C$_{1-6}$alkyl. In a subclass of this class, each R$^d$ is independently selected from the group consisting of F, Cl, —CH$_3$, —CH$_2$CH$_3$, OCH$_2$CH$_3$, —CF$_3$, —OCF$_3$, and —C(O)CH$_3$. In another class of this embodiment, each R$^d$ is independently selected from the group consisting of: halogen. In a subclass of this class, each R$^d$ is independently selected from the group consisting of: F and Cl. In another subclass of this class, each R$^d$ is F. In another subclass of this class, each R$^d$ is Cl.

In another embodiment of the present invention, each R$^e$ is independently selected from the group consisting of: hydrogen, halogen, —CN, —OH, —C$_{1-6}$alkyl, —OC$_{1-6}$alkyl, —CF$_3$, —OCF$_3$, and —C$_{3-6}$ cycloalkyl. In a class of this embodiment, each R$^e$ is independently selected from the group consisting of: hydrogen, F, Cl, —CN, —OH, —CH$_3$, —OCH$_3$, —CF$_3$, —OCF$_3$, and —C$_{3-6}$ cycloalkyl. In another class of this embodiment, each R$^e$ is independently selected from the group consisting of: hydrogen, halogen, —OH, —C$_{1-6}$alkyl, —OC$_{1-6}$alkyl, —OCF$_3$ and —CF$_3$. In a subclass of this class, each R$^e$ is independently selected from the group consisting of: hydrogen, F, Cl, —OH, —OCH$_3$, —OCF$_3$ and —CF$_3$. In another class of this embodiment, each R$^e$ is independently selected from the group consisting of: hydrogen, halogen, —OH, —C$_{1-6}$alkyl, —OC$_{1-6}$alkyl, and —CF$_3$. In a subclass of this class, each R$^e$ is independently selected from the group consisting of: hydrogen, F, Cl, —OH, —CH$_3$, —OCH$_3$, and —CF$_3$. In another class of this embodiment, each R$^e$ is independently selected from the group consisting of halogen. In a subclass of this class, each R$^e$ is independently selected from the group consisting of: F, and Cl. In another subclass of this class, each R$^e$ is F, and Cl. In another subclass of this class, each R$^e$ is Cl.

In another embodiment of the present invention, each R$^f$ is independently selected from the group consisting of: hydrogen, halogen, and —C$_{1-6}$ alkyl. In a class of this embodiment, each R$^f$ is selected from: hydrogen and —C$_{1-6}$ alkyl. In another class of this embodiment, each R$^f$ is hydrogen. In another class of this embodiment, each R$^f$ is halogen. In another class of this embodiment, each R$^f$ is —C$_{1-6}$ alkyl.

In another embodiment of the present invention, each R$^g$ is independently selected from the group consisting of: hydrogen, halogen, and —C$_{1-6}$ alkyl. In a class of this embodiment, each R$^g$ is selected from: hydrogen and —C$_{1-6}$ alkyl. In another class of this embodiment, each R$^g$ is hydrogen. In another class of this embodiment, each R$^g$ is halogen. In another class of this embodiment, each R$^g$ is —C$_{1-6}$ alkyl.

In another embodiment of the present invention, each R$^h$ is independently selected from the group consisting of: hydrogen, and —C$_{1-6}$ alkyl. In a class of this embodiment, each R$^h$ is hydrogen. In another class of this embodiment, each R$^h$ is —C$_{1-6}$ alkyl.

In another embodiment of the present invention, m is 0, 1, 2 or 3. In a class of this embodiment, m is 0, 1 or 2. In another class of this embodiment, m is 0 or 1. In another class of this embodiment, m is 1 or 2. In another class of this embodiment, m is 0 or 2. In another class of this embodiment, m is 0. In another class of this embodiment, m is 1. In another class of this embodiment, m is 2. In another class of this embodiment, m is 3.

In another embodiment of the present invention, n is 0, 1, 2 or 3. In a class of this embodiment, n is 0, 1 or 2. In another class of this embodiment, n is 0 or 1. In another class of this embodiment, n is 1 or 2. In another class of this embodiment, n is 0 or 2. In another class of this embodiment, n is 0. In another class of this embodiment, n is 1. In another class of this embodiment, n is 2. In another class of this embodiment, n is 3.

In another embodiment of the present invention, p is 0, 1, 2 or 3. In a class of this embodiment, p is 0, 1 or 2. In another class of this embodiment, p is 0 or 1. In another class of this embodiment, p is 1 or 2. In another class of this embodiment, p is 0 or 2. In another class of this embodiment, p is 0. In another class of this embodiment, p is 1. In another class of this embodiment, p is 2. In another class of this embodiment, p is 3.

In another embodiment of the present invention, q is 0, 1, 2 or 3. In a class of this embodiment, q is 0, 1 or 2. In another class of this embodiment, q is 0 or 1. In another class of this embodiment, q is 1 or 2. In another class of this embodiment, q is 0 or 2. In another class of this embodiment, q is 0. In another class of this embodiment, q is 1. In another class of this embodiment, q is 2. In another class of this embodiment, q is 3.

In another embodiment of the present invention, r is 0, 1, or 2. In a class of this embodiment, r is 1 or 2. In another class of this embodiment, r is 0 or 2. In another class of this embodiment, r is 0 or 1. In another class of this embodiment, r is 0. In another class of this embodiment, r is 1. In another class of this embodiment, r is 2.

In another embodiment of the present invention, s is 1 or 2. In a class of this embodiment, s is 1. In another class of this embodiment, s is 2.

In another embodiment of the present invention, t is 0, 1, 2 or 3. In a class of this embodiment, t is 0, 1 or 2. In another class of this embodiment, t is 0 or 1. In another class of this embodiment, t is 1 or 2. In another class of this embodiment, t is 0 or 2. In another class of this embodiment, t is 0. In another class of this embodiment, t is 1. In another class of this embodiment, t is 2. In another class of this embodiment, t is 3.

In another embodiment of the present invention, u is 1, 2, or 3. In a class of this embodiment, u is 1 or 2. In another class of this embodiment, u is 2 or 3. In another class of this embodiment, u is 1 or 3. In another class of this embodiment, u is 1. In another class of this embodiment, u is 2. In another class of this embodiment, u is 3.

In another embodiment of the present invention, v is 0, 1, 2 or 3. In a class of this embodiment, v is 0, 1 or 2. In another class of this embodiment, v is 0 or 1. In another class of this embodiment, v is 1 or 2. In another class of this embodiment, v is 0 or 2. In another class of this embodiment, v is 0. In another class of this embodiment, v is I. In another class of this embodiment, v is 2. In another class of this embodiment, v is 3.

In another embodiment of the present invention, the invention relates to compounds of structural formulas I-1 and I-2, wherein:

X is independently selected from the group consisting of: N and $CR^8$;

Y is independently selected from the group consisting of: $NR^5$ or $CR^6R^7$;

Z is independently selected from the group consisting of: N and $CR^4$;

$R^1$ is independently selected from the group consisting of
(1) —$(CH_2)_n$ aryl, and
(2) —$(CH_2)_n$ heteroaryl,
wherein each $CH_2$, aryl and heteroaryl is unsubstituted or substituted with one to three groups independently selected from $R^a$;

$R^2$ is hydrogen;

$R^3$ is independently selected from the group consisting of: —$(CH_2)_m$ aryl, wherein each $CH_2$ and aryl is unsubstituted or substituted with one to three groups independently selected from $R^b$;

$R^4$ is independently selected from the group consisting of:
(1) hydrogen,
(2) —$C_{1-6}$ alkyl, and
(3) —$(CH_2)_p$ heteroaryl,
wherein each $CH_2$, alkyl and heteroaryl is unsubstituted or substituted with one to three groups independently selected from $R^c$;

$R^5$ is independently selected from the group consisting of:
(1) hydrogen,
(2) —$C_{1-6}$ alkyl, and
(3) —$(CH_2)_q$ heteroaryl,
wherein each $CH_2$, alkyl and heteroaryl is unsubstituted or substituted with one to three groups independently selected from $R^d$;

$R^6$ is independently selected from the group consisting of:
(1) —$(CH_2)_v N(R^h)_2$,
(2) —$(CH_2)_v$—$NR^h$—$(CH_2)_{0-2}$—C3-6cycloalkyl,
(3) —$(CH_2)_v$—$NR^h$—$(CH_2)_{0-2}$-aryl,
(4) —$(CH_2)_v$—$NR^h$—$(CH_2)_{1-2}$—O—$(CH_2)_{1-2}$—OH,
(5) —$(CH_2)_v$—$NR^h$—$(CH_2)_{1-2}$—O—$(CH_2)_{1-2}$—$OC_{1-6}$ alkyl, and
(6) —$(CH_2)_v C_{2-6}$cycloheteroalkyl, wherein each $CH_2$, alkyl, cycloalkyl, cycloheteroalkyl and aryl is unsubstituted or substituted with one to three substituents selected from $R^e$;

or a pharmaceutically acceptable salt thereof.

In another embodiment of the present invention, the invention relates to compounds of structural formulas I-1 and 1-2, wherein:

X is independently selected from the group consisting of: N and CH;

Y is independently selected from the group consisting of: $NR^5$ or $CR^6R^7$;

Z is $CR^4$;

$R^1$ is phenyl, wherein phenyl is unsubstituted or substituted with one to three groups independently selected from $R^a$;

$R^2$ is hydrogen;

$R^3$ is phenyl, wherein phenyl is unsubstituted or substituted with one to three groups independently selected from $R^b$;

$R^4$ is independently selected from the group consisting of: hydrogen, and —$C_{1-6}$ alkyl, wherein each alkyl is unsubstituted or substituted with one to three groups independently selected from $R^c$;

$R^5$ is independently selected from the group consisting of: hydrogen and —$C_{1-6}$alkyl, wherein each alkyl is unsubstituted or substituted with one to three groups independently selected from $R^d$;

$R^6$ is independently selected from the group consisting of:
(1) —$(CH_2)_v N(R^h)_2$, and
(2) —$(CH_2)_v C_{2-6}$cycloheteroalkyl, wherein each $CH_2$, alkyl and cycloheteroalkyl is unsubstituted or substituted with one to three substituents selected from $R^e$;

or a pharmaceutically acceptable salt thereof.

In another embodiment of the present invention, the invention relates to compounds of structural formulas Ia-1 and Ia-2:

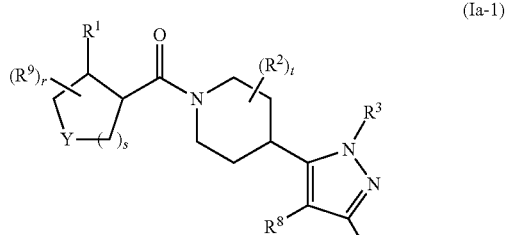

(Ia-1)

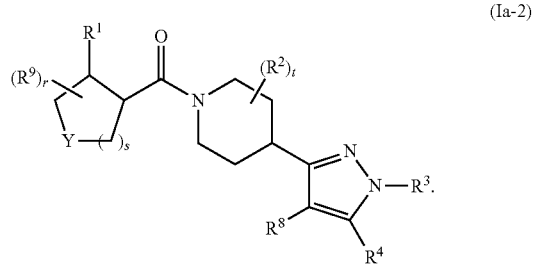

(Ia-2)

In another embodiment of the present invention, the invention relates to compounds of structural formulas Ib-1 and Ib-2:

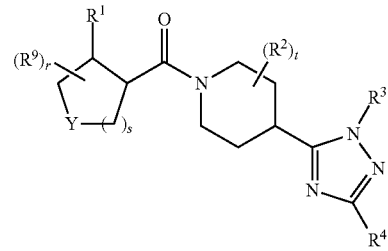
(Ib-1)

(Ib-2)
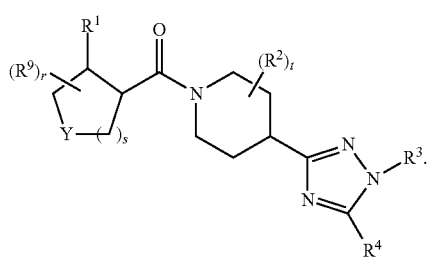

In another embodiment of the present invention, the invention relates to compounds of structural formulas Ic-1 and Ic-2:

(Ic-1)

(Ic-2)
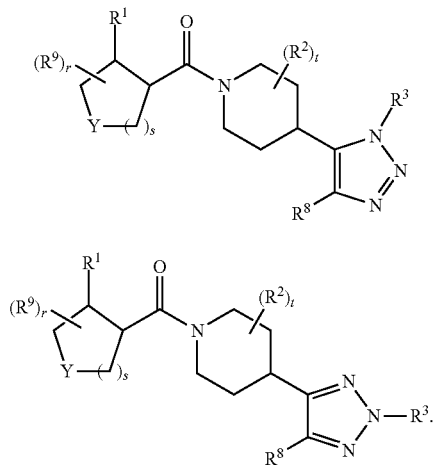

In another embodiment of the present invention, the invention relates to compounds of structural formula Id:

(Id-1)
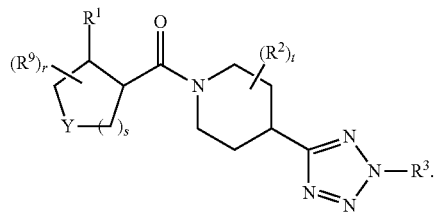

(Id-2)

Illustrative, but nonlimiting, examples of compounds of the present invention that are useful as inhibitors of PrCP are the following:

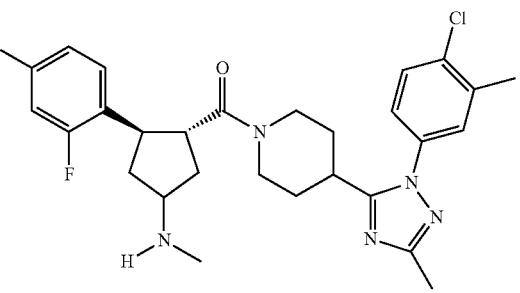

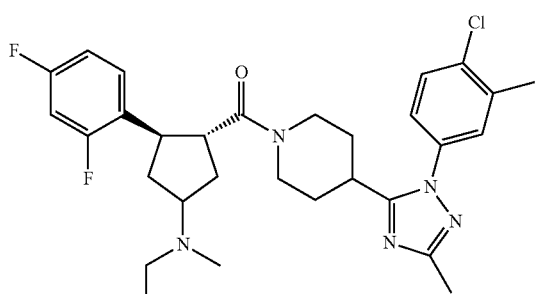

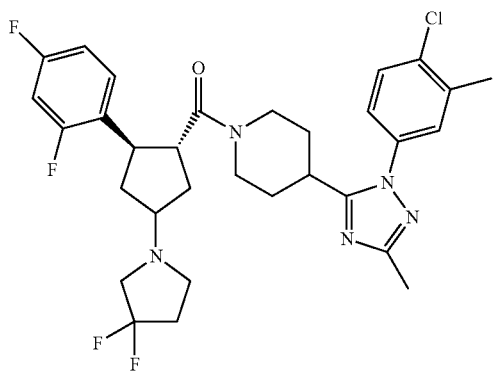

-continued
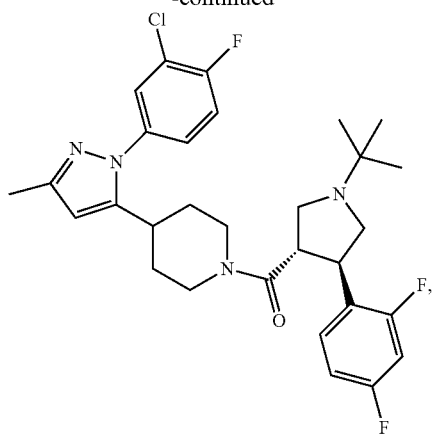
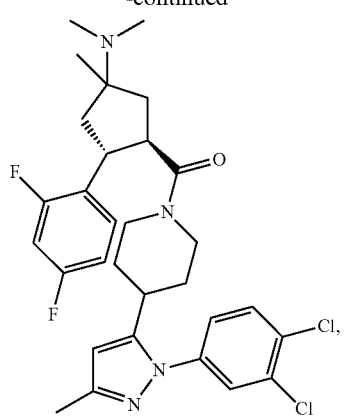
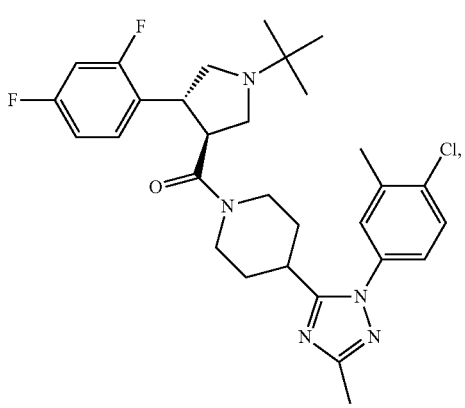
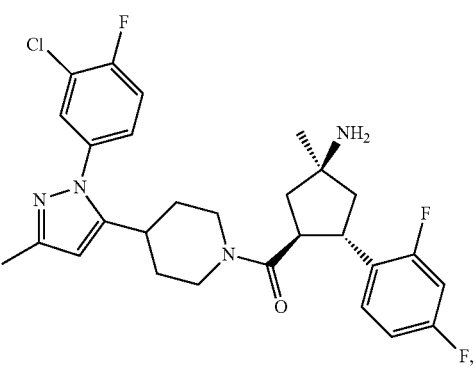
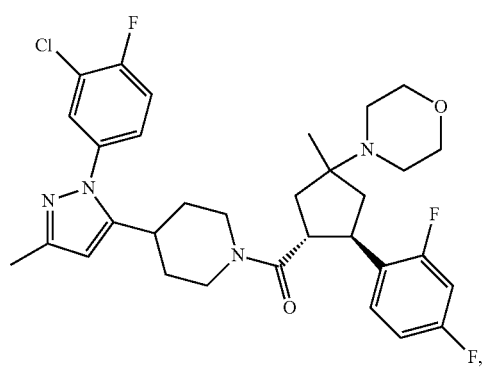

-continued

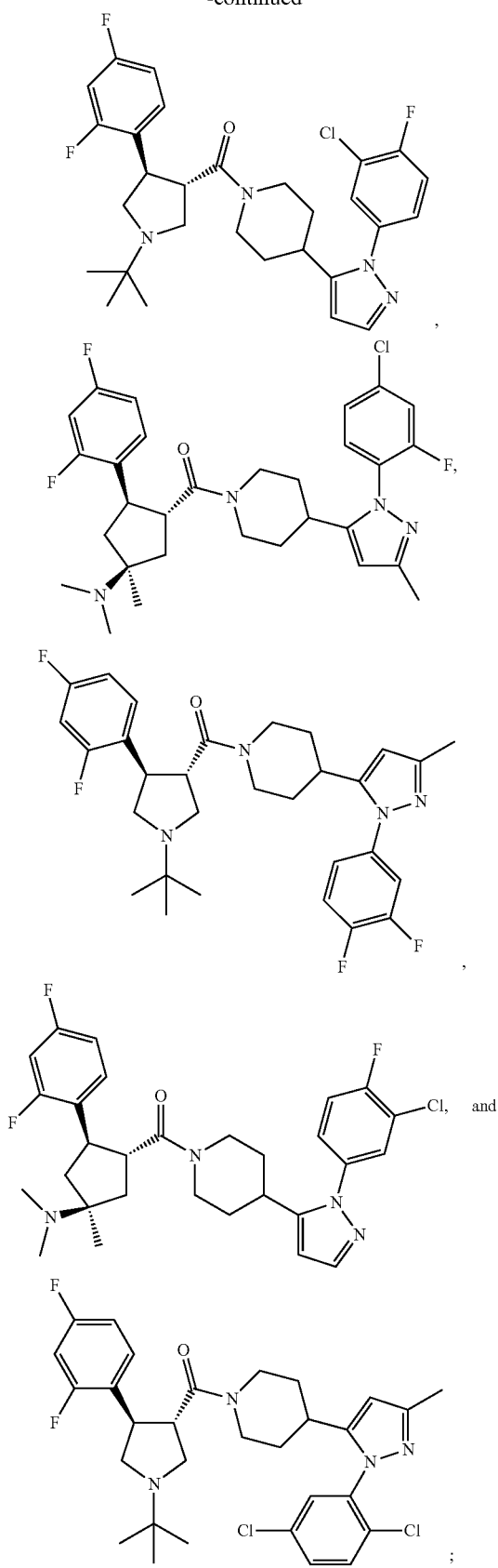

and pharmaceutically acceptable salts thereof.

As used herein the following definitions are applicable.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. When no number of carbon atoms is specified, $C_{1-6}$ is intended.

"Alkenyl" means carbon chains up to 10 carbons, unless otherwise specified, which contain at least one carbon-carbon double bond, and which may be linear or branched or combinations thereof. Examples of alkenyl include vinyl, allyl, isopropenyl, pentenyl, hexenyl, heptenyl, 1-propenyl, 1-butenyl, 2-butenyl, 2-methyl-2-butenyl, and the like.

"Alkynyl" means carbon chains up to 10 carbons, if not otherwise specified, which contain at least one carbon-carbon triple bond, and which may be linear or branched or combinations thereof. Examples of alkynyl include ethynyl, propynyl, butynyl, pentynyl, 3-methyl-1-pentynyl, 2-heptynyl and the like.

The term "alkoxy" refers to straight or branched chain alkoxides of the number of carbon atoms specified (e.g., $C_{1-6}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-6}$ alkylthio), or any number within this range [i.e., methylthio (MeS—), ethylthio, isopropylthio, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl (MeSO$_2$—), ethylsulfonyl, isopropylsulfonyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Cycloalkyl" means mono- or bicyclic or bridged saturated carbocyclic rings, each having from 3 to 14 carbon atoms. Examples of cycloalkyl include cyclopropyl, cyclobutyl, cyclopentyl, cyclohexyl, cycloheptyl, cyclooctyl, and decahydronaphthyl, and the like.

"Cycloalkenyl" means nonaromatic, mono- or bicyclic or bridged carbocyclic rings, each having from 3 to 14 carbon atoms and containing at least one double bond. Examples of cycloalkyl include cyclopropenyl, cyclobutenyl, cyclopentenyl, cyclohexenyl, cycloheptenyl, cyclooxtenyl, decahydronaphthyl, bicyclo[2.2.1]hept-5-en-2-yl, and the like.

"Cycloheteroalkyl" means nonaromatic, mono- or bicyclic or bridged saturated carbocyclic rings, each having from 2 to 14 carbon atoms and containing 1, 2, 3, 4 or 5 heteroatoms selected from N, NH, O and S. Examples of cycloheteroalkyl include tetrahydrofuranyl, azetidinyl, perhydroazepinyl, dihydrofuranyl, dioxanyl, oxanyl, morpholinyl, 1,4-dithianyl, piperazinyl, piperidinyl, 1,3-dioxolanyl, imidazolidinyl, imidazolinyl, pyrrolinyl, pyrrolidinyl, pyranyl, tetrahydropyranyl, dihydropyranyl, oxathiolanyl, dithiolanyl, 1,3-dithianyl, oxathianyl, thiomorpholinyl, dioxidoisothiazolidinyl, azacycloheptyl, diazobicyclo[3.2.1]-octane, and hexahydroindazolyl. The cycloheteroalkyl ring may be substituted on the ring carbons and/or the ring nitrogens.

"Cycloheteroalkenyl" means nonaromatic mono- or bicyclic or bridged rings each having from 2 to 14 carbon atoms containing at least one double bond and containing 1, 2, 3, 4 or 5 heteroatoms selected from N, NH, O and S. Examples of cycloheteroalkenyl include 1,2,4-oxadiazol-5-one, 1,2,4- thiadiazol-5-one, 1,2,4-triazol-3-one, and 1,2,3,6-tetrahydropyridine, dihydro-1,3,4-oxadiazole, and [1,6]-dihydropyridine and the like. In one embodiment of the present invention, cycloheteroalkenyl is dihydro-1,3,4-oxadiazole. In another embodiment of the present invention, cycloheteroalkenyl is [1,6]-dihydropyridine.

"Aryl" means a monocyclic, bicyclic or tricyclic ring system containing 5-14 carbon atoms, wherein at least one of the rings is aromatic. Aryl thus includes ring systems in which an aromatic ring is fused to a non-aromatic ring, such as a cycloalkyl or cycloalkenyl ring. Examples of aryl include phenyl, naphthalene, biphenyl, indane and 5,6,7,8-tetrahydronaphthalene, and the like. In one embodiment of the present invention, aryl is phenyl, naphthalene, biphenyl, indane, and 5,6,7,8-tetrahydronaphthalene. In another embodiment of the present invention, aryl is phenyl, naphthalene, indane and 5,6,7,8-tetrahydronaphthalene. In one class of this embodiment, aryl is phenyl and naphthalene. In another class of this embodiment, aryl is phenyl. In another class of this embodiment, aryl is naphthalene.

"Heteroaryl" means a monocyclic, bicyclic or tricyclic ring system containing 5-14 carbon atoms and containing 1, 2, 3, 4 or 5 heteroatoms selected from N, NH, O and S wherein at least one of the heteroatom containing rings is aromatic. Heteroaryls thus includes heteroaryls fused to other kinds of rings, such as aryls, cycloalkyls and heterocycles that are not aromatic. Heteroaryl includes ring systems in which an aromatic heteroatom containing ring is fused to a non-aromatic ring, such as a cycloalkyl, cycloalkenyl, cycloheteroalkyl or cycloheteroalkenyl ring, and also includes ring systems in which an aryl ring is fused to a non-aromatic heteroatom containing ring, such as a cycloheteroalkyl or cycloheteroalkenyl ring. Examples of heteroaryls include: pyrazole, pyridine, pyrazine, pyrrole, pyrimidine, pyridazine, benzoimidazole, quinoline, isothiazole, isoquinoline, indole, indazole, carbazole, benzotriazole, benzofuran, benzothiazole, benzothiophene, benzoisooxazole, oxazole, oxadiazole, furan, benzoxazole, isoxazole, indoline, isoindoline, tetrazole, imidazole, oxadiazole (in particular, 1,3,4-oxadiazol-2-yl and 1,2,4-oxadiazol-3-yl), thiazole, thiophene, thiadiazole, triazole, triazine, tetrazole, thiene, benzothiazole, bernzopyrazole, benzothiadiazole, dihydrobenzofuran, indazole, isoindole, dihydrobenzothiene, indolizine, cinnoline, phthalazine, quinazoline, naphthyridine, carbazole, quinoxaline, purine, isobenzylfuran, benzothiene, isoquinoline, dibenzofuran, isothiazole, imidazopyridine, benzodioxole, dihydropyridine, dihydropyrrolopyridine, dihydrobenzooxazine, benzodioxole, benzodioxine, pyrrolopyridine, triazolopyridine, dihydropyridooxazine, dihydrobenzoxazine, dihydroindole, dihydroisoindole, dihydrobenzoimidazole, dihydroquinoline, tetrahydroisoquinoline, tetrahydrocyclopentaindole, tetrahydroquinoxaline, and tetrahydropyridine. For heterocycloalkyl and heteroaryl groups, rings and ring systems containing from 3-15 atoms are included, forming 1-3 rings.

"Halogen" includes fluorine, chlorine, bromine and iodine. Chlorine and fluorine are generally preferred. Fluorine is most preferred when the halogens are substituted on an alkyl or alkoxy group (e.g. $CF_{3O}$ and $CF_3CH_2O$). In one embodiment of the present invention, halogen is selected from fluorine, chlorine, and bromine.

"Oxo" means the functional group "=O" which is an oxygen atom connected to the molecule via a double bond, such as, for example, (1) "C=(O)", that is a carbonyl group; (2) "S=(O)", that is, a sulfoxide group; and (3) "N=(O)", that is, an N-oxide group, such as pyridyl-N-oxide.

In choosing compounds of the present invention, one of ordinary skill in the art will recognize that the various substituents, i.e. $R^1$, $R^2$, etc., are to be chosen in conformity with well-known principles of chemical structure connectivity and stability. When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the functional group adjacent to the point of attachment is described first, with our without a bond "—", followed by the terminal portion of the designated side chain. For example, a —$C_{1-5}$ alkylcarbonylamino $C_{1-6}$ alkyl substituent is equivalent to:

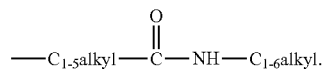

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The terms "compounds of structural formula I" and "formula I" include the compounds of structural formulas I-1, I-2, Ia-1, Ia-2, Ib-1, Ib-2, Ic-1, Ic-2, Id-1, and Id-2, and pharmaceutically acceptable salts thereof.

Compounds of structural formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration. Alternatively, any stereoisomer of a compound of the general structural formula I may be obtained by stereospecific synthesis using optically pure starting materials or reagents of known absolute configuration.

Compounds of the Formula I may be separated into diastereoisomeric pairs of enantiomers by, for example, fractional crystallization from a suitable solvent, for example MeOH or ethyl acetate or a mixture thereof. The pair of enantiomers thus obtained may be separated into individual stereoisomers by conventional means, for example by the use of an optically active amine as a resolving agent or on a chiral HPLC column. Alternatively, any enantiomer of a compound of the general Formula I may be obtained by stereospecific synthesis using optically pure starting materials or reagents of known configuration.

If desired, racemic mixtures of the compounds may be separated so that the individual enantiomers are isolated. Racemic mixtures can be separated into their individual enantiomers by any of a number of conventional methods, which include chiral chromatography, derivatization with a chiral auxiliary followed by separation by chromatography or crystallization, and fractional crystallization of diastereomeric salts. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

In the compounds of structural formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations. The compounds of the present invention may be administered in the form of a pharmaceutically acceptable salt.

The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetyl, pivaloyl, benzoyl, and aminoacyl, can be employed. Included are those esters and acyl groups known in the art for modifying the solubility or hydrolysis characteristics for use as sustained-release or prodrug formulations.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

The compounds of formula I are effective as inhibitors of prolylcarboxypeptidase (PRCP). The compounds of formula I are therefore useful for the treatment, control and/or prevention of diseases, disorders or conditions responsive to the inhibition of the prolylcarboxypeptidase (PRCP) enzyme, including but not limited to: abnormal metabolism, obesity, diabetes, metabolic syndrome, obesity related disorders, diabetes related disorders, hypertension, dyslipidemia, stroke, gallbladder disease, cardiovascular disease, osteoarthritis, rheumatoid arthritis, hypercholesterolemia, stable angina, unstable angina, artherosclerosis, sleep apnea, respiratory problems, cancer, and stroke.

One aspect of the present invention provides a method for the treatment or prevention of disorders, diseases or conditions responsive to the inhibition of prolylcarboxypeptidase in a subject in need thereof which comprises administering to the subject a therapeutically or prophylactically effective amount of a compound of formula I, or a pharmaceutically acceptable salt thereof.

Another aspect of the present invention provides a method for the treatment or prevention of obesity, diabetes, an obesity related disorder or a diabetes related disorder in a subject in need thereof which comprises administering to said subject a therapeutically or prophylactically effective amount of a prolylcarboxypeptidase inhibitor of formula I. Another aspect of the present invention provides a method for the treatment or prevention of obesity in a subject in need thereof which comprises administering to the subject a therapeutically or prophylactically effective amount of a compound of formula I, or a pharmaceutically acceptable salt thereof. Another aspect of the present invention provides a method for reducing food intake in a subject in need thereof which comprises administering to the subject a therapeutically or prophylactically effective amount of a compound of formula I, or a pharmaceutically acceptable salt thereof. Another aspect of the present invention provides a method for reducing body fat mass in a subject in need thereof which comprises administering to the subject a therapeutically or prophylactically effective amount of a compound of formula I, or a pharmaceutically acceptable salt thereof. Another aspect of the present invention provides a method for losing weight in a subject in need thereof which comprises administering to the subject a therapeutically or prophylactically effective amount of a compound of formula I, or a pharmaceutically acceptable salt thereof.

Another aspect of the present invention provides a method for the treatment or prevention of an obesity-related disorder selected from the group consisting of: overeating, binge eating, hypertension, elevated plasma insulin concentrations, insulin resistance, hyperlipidemia, endometrial cancer, breast cancer, prostate cancer, colon cancer, kidney cancer, osteoarthritis, obstructive sleep apnea, heart disease, abnormal heart rhythms and arrythmias, myocardial infarction, congestive heart failure, coronary heart disease, sudden death, stroke, polycystic ovary disease, craniopharyngioma, metabolic syndrome, insulin resistance syndrome, sexual and reproductive dysfunction, infertility, hypogonadism, hirsutism, obesity-related gastro-esophageal reflux, Pickwickian syndrome, inflammation, systemic inflammation of the vasculature, arteriosclerosis, hypercholesterolemia, hyperuricaemia, lower back pain, gallbladder disease, gout, constipation, irritable bowel syndrome, inflammatory bowel syndrome, cardiac hypertrophy, left ventricular hypertrophy, in a subject in need thereof which comprises administering to the subject a therapeutically or prophylactically effective amount of a compound of formula I, or a pharmaceutically acceptable salt thereof.

Another aspect of the present invention provides a method for the treatment or prevention of diabetes, in a subject in need thereof which comprises administering to the subject a therapeutically or prophylactically effective amount of a compound of formula I, or a pharmaceutically acceptable salt thereof.

Another aspect of the present invention provides a method for the treatment or prevention of a diabetes related disorder in a subject in need thereof which comprises administering to the subject a therapeutically or prophylactically effective amount of a compound of formula I, or a pharmaceutically acceptable salt thereof.

Another aspect of the present invention provides a method for the treatment or prevention of a diabetes related disorder selected from the group consisting of: hyperglycemia, low glucose tolerance, insulin resistance, obesity, lipid disorders, dyslipidemia, hyperlipidemia, hypertriglyceridemia, hypercholesterolemia, low HDL levels, high LDL levels, atherosclerosis and its sequelae, vascular restenosis, irritable bowel syndrome, inflammatory bowel disease, including Crohn's disease and ulcerative colitis, other inflammatory conditions, pancreatitis, abdominal obesity, neurodegenerative disease, retinopathy, nephropathy, neuropathy, Syndrome X, and ovarian hyperandrogenism (polycystic ovarian syndrome), in a subject in need thereof which comprises administering to the subject a therapeutically or prophylactically effective amount of a compound of formula I, or a pharmaceutically acceptable salt thereof.

The present invention also relates to methods for treating or preventing obesity by administering a compound of formula I in combination with a therapeutically or prophylactically effective amount of another agent known to be useful to treat or prevent the condition. The present invention also relates to methods for treating or preventing diabetes by administering a compound of formula I in combination with a therapeutically or prophylactically effective amount of another agent known to be useful to treat or prevent the condition. The present invention also relates to methods for treating or preventing obesity related disorders by administering a compound of formula I in combination with a therapeutically or prophylactically effective amount of another agent known to be useful to treat or prevent the condition.

Yet another aspect of the present invention relates to the use of a therapeutically effective amount of a compound of formula I, or a pharmaceutically acceptable salt or ester thereof, and a therapeutically effective amount of at least one agent selected from the group consisting of simvastatin, mevastatin, ezetimibe, atorvastatin, sitagliptin, metformin, sibutramine, orlistat, Qnexa, topiramate, phentermine, losartan, losartan with hydrochlorothiazide, or rimonabant, or a pharmaceutically acceptable salt or ester or prodrug thereof, for the manufacture of a medicament useful for the treatment, control, or prevention of obesity, diabetes, a diabetes related disorder, or an obesity-related disorder in a subject in need of such treatment.

Another aspect of the present invention provides a pharmaceutical composition comprising a compound of formula I, and a pharmaceutically acceptable carrier.

Yet another aspect of the present invention relates to the use of a compound of formula I for the manufacture of a medicament useful for the treatment or prevention, or suppression of a disease mediated by prolylcarboxypeptidase (PRCP) in a subject in need thereof.

Yet another aspect of the present invention relates to the use of a compound of formula I for the manufacture of a medicament useful for the treatment or prevention, or suppression of a disease mediated by prolylcarboxypeptidase (PRCP), wherein the disease is selected from the group consisting of obesity, diabetes, an obesity-related disorder and a diabetes related disorder in a subject in need thereof.

Yet another aspect of the present invention relates to the use of a therapeutically effective amount of a compound of formula I, or a pharmaceutically acceptable salt thereof, and a therapeutically effective amount of an agent selected from the group consisting of an insulin sensitizer, an insulin mimetic, a sulfonylurea, an α-glucosidase inhibitor, a dipeptidyl peptidase 4 (DPP-4) inhibitor, a glucagons like peptide 1 (GLP-1) agonist, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a melanocortin 4 receptor agonist, a bombesin receptor subtype 3 agonist, a ghrelin receptor antagonist, PYY, $PYY_{3-36}$, and a NK-1 antagonist, or a pharmaceutically acceptable salt thereof, for the manufacture of a medicament useful for the treatment, control, or prevention of obesity, diabetes or an obesity-related disorder in a subject in need of such treatment. Yet another aspect of the present invention relates to the use of a therapeutically effective amount of a compound of formula I, and pharmaceutically acceptable salts and esters thereof, and a therapeutically effective amount of an agent selected from the group consisting of an insulin sensitizer, an insulin mimetic, a sulfonylurea, an α-glucosidase inhibitor, a dipeptydyl peptidase 4 inhibitor, a glucagon-like peptide 1 agonist, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a melanocortin 4 receptor agonist, a bombesin receptor subtype 3 agonist, a ghrelin receptor antagonist, PYY, $PYY_{3-36}$, and a NK-1 antagonist, or a pharmaceutically acceptable salt thereof, for the manufacture of a medicament for treatment or prevention of obesity, diabetes, an obesity related disorder or a diabetes related disorder which comprises an effective amount of a the compound of formula I, and an effective amount of the agent, together or separately. Yet another aspect of the present invention relates to a product containing a therapeutically effective amount of a compound of formula I, or a pharmaceutically acceptable salt thereof; and a therapeutically effective amount of an agent selected from the group consisting of an insulin sensitizer, an insulin mimetic, a sulfonylurea, an α-glucosidase inhibitor, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanocortin 4 receptor agonist, a melanin-concentrating hormone receptor antagonist, a bombesin receptor subtype 3 agonist, a ghrelin receptor antagonist, PYY, $PYY_{3-6}$, and a NK-1 antagonist, or a pharmaceutically acceptable salt thereof, as a combined preparation for simultaneous, separate or sequential use in obesity, diabetes, an obesity-related disorder or a diabetes related disorder.

The compounds of formula I can be provided in kit. Such a kit typically contains an active compound in dosage forms for administration. A dosage form contains a sufficient amount of active compound such that a beneficial effect can be obtained when administered to a patient during regular intervals, such as 1, 2, 3, 4, 5 or 6 times a day, during the course of 1 or more days. Preferably, a kit contains instructions indicating the use of the dosage form for weight reduction (e.g., to treat obesity) and the amount of dosage form to be taken over a specified time period.

Compounds of formula I are inhibitors of prolylcarboxypeptidase (PRCP) and as such are useful in the treatment, control or prevention of diseases, disorders or conditions responsive to the modulation of prolylcarboxypeptidase (PRCP). Such diseases, disorders or conditions include, but are not limited to, abnormal metabolism, obesity, diabetes, metabolic syndrome, obesity related disorders, diabetes related disorders, hypertension, dyslipidemia, stroke, gallbladder disease, cardiovascular disease, osteoarthritis, rheumatoid arthritis, hypercholesterolemia, stable angina, unstable angina, artherosclerosis, sleep apnea, respiratory problems, cancer, and stroke. Such diseases, conditions and disorders also include non-obese overweight conditions and normal weight conditions where weight control or management is desired in order to prevent an obese or overweight condition from developing, or to maintain a healthy weight.

The compounds of formula I, and compositions thereof, are useful for the treatment or prevention of disorders associated with excessive food intake, such as obesity and obesity-related disorders. The obesity herein may be due to any cause, whether genetic or environmental.

The obesity-related disorders herein are associated with, caused by, or result from obesity. Examples of obesity-related disorders include overeating, binge eating, bulimia nervosa, hypertension, type 2 diabetes, elevated plasma insulin concentrations, hyperinsulinemia, insulin resistance, glucose intolerance, dyslipidemia, hyperlipidemia, endometrial cancer, breast cancer, prostate cancer, kidney cancer, colon cancer, osteoarthritis, obstructive sleep apnea, cholelithiasis, cholecystitis, gallstones, gout, gallbladder disease, abnormal heart rhythms and arrythmias, myocardial infarction, congestive heart failure, coronary heart disease, angina pectoris, sudden death, stroke, metabolic syndrome, psychological disorders (depression, eating disorders, distorted bodyweight, and low self esteem), and other pathological conditions showing reduced metabolic activity or a decrease in resting energy expenditure as a percentage of total fat-free mass, e.g., children with acute lymphoblastic leukemia. Further examples of obesity-related disorders are sexual and reproductive dysfunction, such as polycystic ovary disease, infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. Additionally, the present compounds are useful in the treatment of any condition in which it is desirable to lose weight or to reduce food intake. Additionally, the present compounds are useful in the treatment of any condition in which it is desirable to enhance cognition and memory, such as Alzheimer's Disease. The compositions of the present invention are also useful for reducing the risk of secondary outcomes of obesity, such as reducing the risk of left ventricular hypertrophy. Therefore, the present invention provides methods of treatment or prevention of such diseases, conditions and/or disorders modulated by prolylcarboxypeptidase (PRCP) in an animal which comprises administering to the animal in need of such treatment a compound of formula I, in particular a therapeutically or prophylactically effective amount thereof.

The term "inhibitor" as used herein means a composition of matter which when administered to a mammal, such as a human, inhibits the biological activity attributable to the level or presence of an endogenous compound in the mammal. Inhibition of PrCP includes, but is not limited to, inhibiting the biological activity of the PrCP enzyme or molecule.

The term "subject" means a mammal. One embodiment of the term "mammal" is a "human," said human being either male or female. The instant compounds are also useful for treating or preventing obesity and obesity related disorders in cats and dogs. As such, the teen "mammal" includes companion animals such as cats and dogs. The term "mammal in need thereof" refers to a mammal who is in need of treatment or prophylaxis as determined by a researcher, veterinarian, medical doctor or other clinician.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The term "metabolic syndrome", also known as syndrome X, is defined in the Third Report of the National Cholesterol Education Program Expert Panel on Detection, Evaluation and Treatment of High Blood Cholesterol in Adults (ATP-III). E. S. Ford et al., JAMA, vol. 287 (3), Jan. 16, 2002, pp 356-359. Briefly, a person is defined as having metabolic syndrome if the person has three or more of the following symptoms: abdominal obesity, hypertriglyceridemia, low HDL cholesterol, high blood pressure, and high fasting plasma glucose. The criteria for these are defined in ATP-III.

The term "diabetes," as used herein, includes both insulin-dependent diabetes mellitus (i.e., IDDM, also known as type I diabetes) and non-insulin-dependent diabetes mellitus (i.e., NIDDM, also known as Type II diabetes). Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compositions of the present invention are useful for treating both Type I and Type II diabetes. The compositions are especially effective for treating Type II diabetes. The compounds or combinations of the present invention are also useful for treating and/or preventing gestational diabetes mellitus.

Diabetes is characterized by a fasting plasma glucose level of greater than or equal to 126 mg/dl. A diabetic subject has a fasting plasma glucose level of greater than or equal to 126 mg/dl. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of $\geq 140$ mg/dl and <200 mg/dl); or insulin resistance, resulting in an increased risk of developing diabetes.

"Diabetes related disorders" are diseases, disorders and conditions that are related to Type 2 diabetes, and therefore may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequalae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component. In Syndrome X, also known as Metabolic Syndrome, obesity is thought to promote insulin resistance, diabetes, dyslipidemia, hypertension, and increased cardiovascular risk. Therefore, inhibitors of prolylcarboxypeptidase (PRCP) may also be useful to treat hypertension associated with this condition.

Treatment of diabetes mellitus refers to the administration of a compound or combination of the present invention to treat diabetes. One outcome of treatment may be decreasing the glucose level in a subject with elevated glucose levels. Another outcome of treatment may be improving glycemic control. Another outcome of treatment may be decreasing insulin levels in a subject with elevated insulin levels. Another outcome of the treatment of diabetes is to reduce an increased plasma glucose concentration. Another outcome of the treatment of diabetes is to reduce an increased insulin concentration. Still another outcome of the treatment of diabetes is to reduce an increased blood triglyceride concentration. Still another outcome of the treatment of diabetes is to increase insulin sensitivity. Still another outcome of the treatment of diabetes may be enhancing glucose tolerance in a subject with glucose intolerance. Still another outcome of the treatment of diabetes is to reduce insulin resistance. Another outcome of the treatment of diabetes is to lower plasma insulin levels. Still another outcome of treatment of diabetes is an improvement in glycemic control, particularly in type 2 diabetes.

Prevention of diabetes mellitus, in particular diabetes associated with obesity, refers to the administration of a compound or combination of the present invention to prevent or treat the onset of diabetes in a subject in need thereof. A subject in need of preventing diabetes in a pre-diabetic subject.

"Obesity" is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asia-Pacific, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes, non-insulin dependent diabetes mellitus—type II (2), impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

Treatment of obesity and obesity-related disorders refers to the administration of the compounds or combinations of the present invention to reduce or maintain the body weight of an obese subject. One outcome of treatment may be reducing the body weight of an obese subject relative to that subject's body weight immediately before the administration of the compounds or combinations of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and in weight reduction in subjects in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds or combinations of the present invention to reduce or maintain the body weight of a subject at risk of obesity. One outcome of prevention may be reducing the body weight of a subject at risk of obesity relative to that subject's body weight immediately before the administration of the compounds or combinations of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovary disease, cardiovascular diseases, osteoarthritis, hypertension, dyslipidemia, insulin resistance, hypercholesterolemia, hypertriglyceridemia, and cholelithiasis.

The terms "administration of" and or "administering" a compound should be understood to mean providing a compound of the invention or a prodrug of a compound of the invention to a subject in need of treatment. The administration of the compounds of the present invention in order to practice the present methods of therapy is carried out by administering a therapeutically effective amount of the compound to a subject in need of such treatment or prophylaxis. The need for a prophylactic administration according to the methods of the present invention is determined via the use of well known risk factors.

The term "therapeutically effective amount" as used herein means the amount of the active compound that will elicit the biological or medical response in a tissue, system, subject, mammal, or human that is being sought by the researcher, veterinarian, medical doctor or other clinician, which includes alleviation of the symptoms of the disorder being treated. The novel methods of treatment of this invention are for disorders known to those skilled in the art. The term "prophylactically effective amount" as used herein means the amount of the active compound that will elicit the biological or medical response in a tissue, system, subject, mammal, or human that is being sought by the researcher, veterinarian, medical doctor or other clinician, to prevent the onset of the disorder in subjects as risk for obesity or the disorder. The therapeutically or prophylactically effective amount, or dosage, of an individual compound is determined, in the final analysis, by the physician in charge of the case, but depends on factors such as the exact disease to be treated, the severity of the disease and other diseases or conditions from which the patient suffers, the chosen route of administration, other drugs and treatments which the patient may concomitantly require, and other factors in the physician's judgement.

Administration and Dose Ranges

Any suitable route of administration may be employed for providing a subject or mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally or topically.

The effective dosage of active ingredient employed may vary depending on the particular compound employed, the mode of administration, the condition being treated and the severity of the condition being treated. Such dosage may be ascertained readily by a person skilled in the art.

Generally satisfactory results are obtained when the compounds of formula I are administered at a daily dosage of from about 0.001 milligram to about 50 milligrams per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

In the case where an oral composition is employed, a suitable dosage range is, e.g. from about 0.01 mg to about 1500 mg of a compound of Formula I per day, preferably from about 0.1 mg to about 600 mg per day, more preferably from about 0.1 mg to about 100 mg per day. For oral administration, the compositions are preferably provided in the form of tablets containing from 0.01 to 1,000 mg, preferably 0.01, 0.05, 0.1, 0.5, 1, 2.5, 5, 10, 15, 20, 25, 30, 40, 50, 100, 250, 500, 600, 750, 1000, 1250 or 1500 milligrams of the active ingredient for the symptomatic adjustment of the dosage to the patient to be treated.

For use where a composition for intranasal administration is employed, intranasal formulations for intranasal administration comprising 0.001-10% by weight solutions or suspensions of the compounds of formula I in an acceptable intranasal formulation may be used.

For use where a composition for intravenous administration is employed, a suitable dosage range is from about 0.001 mg to about 50 mg, preferably from 0.01 mg to about 50 mg, more preferably 0.1 mg to 10 mg, of a compound of formula I per kg of body weight per day. This dosage regimen may be adjusted to provide the optimal therapeutic response. It may be necessary to use dosages outside these limits in some cases.

For the treatment of diseases of the eye, ophthalmic preparations for ocular administration comprising 0.001-1% by weight solutions or suspensions of the compounds of formula I in an acceptable ophthalmic formulation may be used.

The magnitude of prophylactic or therapeutic dosage of the compounds of the present invention will, of course, vary depending on the particular compound employed, the mode of administration, the condition being treated and the severity of the condition being treated. It will also vary according to the age, weight and response of the individual patient. Such dosage may be ascertained readily by a person skilled in the art.

Combination Therapy

Compounds of Formula I may be used in combination with other drugs that may also be useful in the treatment or amelioration of the diseases or conditions for which compounds of Formula I are useful. Such other drugs may be administered, by a route and in an amount commonly used therefor, contemporaneously or sequentially with a compound of Formula I. In the treatment of patients who have Type 2 diabetes, insulin resistance, obesity, metabolic syndrome, and co-morbidities that accompany these diseases, more than one drug is commonly administered. The compounds of this invention may generally be administered to a patient who is already taking one or more other drugs for these conditions. Often the compounds will be administered to a patient who is already being treated with one or more antidiabetic compound, such as metformin, sulfonylureas, and/or PPAR agonists, when the patient's glycemic levels are not adequately responding to treatment.

When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) PPAR gamma agonists and partial agonists, including both glitazones and non-glitazones (e.g. troglitazone, pioglitazone, englitazone, MCC-555, rosiglitazone, balaglitazone, netoglitazone, T-131, LY-300512, LY-818, and compounds disclosed in WO02/08188, WO2004/020408, and WO2004/020409.
(b) biguanides, such as metformin and phenformin;
(c) protein tyrosine phosphatase-1B (PTP-1B) inhibitors;
(d) dipeptidyl peptidase-IV (DPP-4) inhibitors, such as sitagliptin, saxagliptin, vildagliptin, and alogliptin;
(e) insulin or insulin mimetics;
(f) sulfonylureas such as tolbutamide, glimepiride, glipizide, and related materials;
(g) α-glucosidase inhibitors (such as acarbose);
(h) agents which improve a patient's lipid profile, such as (i) HMG-CoA reductase inhibitors (lovastatin, simvastatin, rosuvastatin, pravastatin, fluvastatin, atorvastatin, rivastatin, itavastatin, ZD-4522 and other statins), (ii) bile acid sequestrants (cholestyramine, colestipol, and dialkylaminoalkyl derivatives of a cross-linked dextran), (iii) niacin receptor agonists, nicotinyl alcohol, nicotinic acid, or a salt thereof, (iv) PPARα agonists, such as fenofibric acid derivatives (gemfibrozil, clofibrate, fenofibrate and bezafibrate), (v) cholesterol absorption inhibitors, such as ezetimibe, (vi) acyl CoA: cholesterol acyltransferase (ACAT) inhibitors, such as avasimibe, (vii) CETP inhibitors, such as torcetrapib, and (viii) phenolic antioxidants, such as probucol;
(i) PPARα/γ dual agonists, such as muraglitazar, tesaglitazar, farglitazar, and JT-501;
(j) PPARδ agonists, such as those disclosed in WO97/28149;
(k) anti-obesity compounds, such as fenfluramine, dexfenfluramine, phentiramine, subitramine, orlistat, neuropeptide Y Y5 inhibitors, MC4R agonists, cannabinoid receptor 1 (CB-1) antagonists/inverse agonists (e.g., rimonabant and taranabant), and $β_3$ adrenergic receptor agonists;
(l) ileal bile acid transporter inhibitors;
(m) agents intended for use in inflammatory conditions, such as aspirin, non-steroidal anti-inflammatory drugs, glucocorticoids, azulfidine, and cyclooxygenase-2 (Cox-2) selective inhibitors;
(n) glucagon receptor antagonists;
(o) GLP-1;
(p) GIP-1;
(q) GLP-1 analogs and derivatives, such as exendins, (e.g., exenatide and liruglatide);
(r) 11β-hydroxysteroid dehydrogenase-1 (HSD-1) inhibitors;
(s) inhibitors of cholesteryl ester transfer protein (CETP), such as torcetrapib;
(t) SSTR3 antagonists;
(u) other SSTR5 antagonists;
(v) acetyl CoA carboxylase-1 and/or -2 inhibitors;
(w) AMPK activators;
(x) agonists of GPR-119;
(y) glucokinase agonists; and
(z) FGF-21 agonists.

The above combinations include combinations of a compound of the present invention not only with one other active compound, but also with two or more other active compounds. Non-limiting examples include combinations of compounds having Formula I with two or more active compounds selected from biguanides, sulfonylureas, HMG-CoA reductase inhibitors, other PPAR agonists, PTP-1B inhibitors, DPP-4 inhibitors, and cannabinoid receptor 1 (CB 1) inverse agonists/antagonists.

Antiobesity compounds that can be combined with compounds described herein include fenfluramine, dexfenfluramine, phentermine, sibutramine, orlistat, neuropeptide Y1 or Y5 antagonists, cannabinoid CB 1 receptor antagonists or inverse agonists, melanocortin receptor agonists, in particular, melanocortin-4 receptor agonists, ghrelin antagonists, bombesin receptor agonists, and melanin-concentrating hormone (MCH) receptor antagonists. For a review of anti-obesity compounds that can be combined with compounds described herein, see S. Chaki et al., "Recent advances in feeding suppressing agents: potential therapeutic strategy for the treatment of obesity," *Expert Opin. Ther. Patents*, 11: 1677-1692 (2001); D. Spanswick and K. Lee, "Emerging antiobesity drugs," *Expert Opin. Emerging Drugs*, 8: 217-237 (2003); and J. A. Fernandez-Lopez, et al., "Pharmacological Approaches for the Treatment of Obesity," *Drugs*, 62: 915-944 (2002).

Neuropeptide Y5 antagonists that can be combined with compounds described herein include those disclosed in U.S. Pat. No. 6,335,345 (1 Jan. 2002) and WO 01/14376 (1 Mar. 2001); and specific compounds identified as GW 59884A; GW 569180A; LY366377; and CGP-71683A.

Cannabinoid CB1 receptor antagonists that can be combined with compounds described herein include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. No. 5,532,237; U.S. Pat. No. 5,292,736; PCT Publication WO 03/086288; PCT Publication WO 03/087037; PCT Publication WO 04/048317; PCT Publication WO 03/007887; PCT Publication WO 03/063781; PCT Publication WO 03/075660; PCT Publication WO 03/077847; PCT Publication WO 03/082190; PCT Publication WO 03/082191; PCT Publication WO 03/087037; PCT Publication WO 03/086288; PCT Publication WO 04/012671; PCT Publication WO 04/029204; PCT Publication WO 04/040040; PCT Publication WO 01/64632; PCT Publication WO 01/64633; and PCT Publication WO 01/64634.

Suitable melanocortin-4 receptor (MC4R) agonists include, but are not limited to, those disclosed in U.S. Pat. No. 6,294,534, U.S. Pat. Nos. 6,350,760, 6,376,509, 6,410,548, 6,458,790, U.S. Pat. No. 6,472,398, U.S. Pat. No. 5,837,521, U.S. Pat. No. 6,699,873, which are hereby incorporated by reference in their entirety; in US Patent Application Publication Nos. US 2002/0004512, US2002/0019523, US2002/0137664, US2003/0236262, US2003/0225060, US2003/0092732, US2003/109556, US 2002/0177151, US 2002/187932, US 2003/0113263, which are hereby incorporated by reference in their entirety; and in WO 99/64002, WO 00/74679, WO 02/15909, WO 01/70708, WO 01/70337, WO 01/91752, WO 02/068387, WO 02/068388, WO 02/067869, WO 03/007949, WO 2004/024720, WO 2004/089307, WO 2004/078716, WO 2004/078717, WO 2004/037797, WO 01/58891, WO 02/070511, WO 02/079146, WO 03/009847, WO 03/057671, WO 03/068738, WO 03/092690, WO 02/059095, WO 02/059107, WO 02/059108, WO 02/059117, WO 02/085925, WO 03/004480, WO 03/009850, WO 03/013571, WO 03/031410, WO 03/053927, WO 03/061660, WO 03/066597, WO 03/094918, WO 03/099818, WO 04/037797, WO 04/048345, WO 02/018327, WO 02/080896, WO 02/081443, WO 03/066587, WO 03/066597, WO 03/099818, WO 02/062766, WO 03/000663, WO 03/000666, WO 03/003977, WO 03/040107, WO 03/040117, WO 03/040118, WO 03/013509, WO 03/057671, WO 02/079753, WO 02/092566, WO 03/-093234, WO 03/095474, and WO 03/104761.

Specific compounds of use in combination with a compound of the present invention include: simvastatin, mevastatin, ezetimibe, atorvastatin, sitagliptin, metformin, sibutramine, orlistat, Qnexa, topiramate, naltrexone, bupriopion, phentermine, and losartan, losartan with hydrochlorothiazide.

Examples of other anti-obesity agents that can be employed in combination with a compound of formula I, II, III or IV are disclosed in "Patent focus on new anti-obesity agents," *Exp. Opin. Ther. Patents*, 10: 819-831 (2000); "Novel anti-obesity drugs," *Exp. Opin. Invest. Drugs*, 9: 1317-1326 (2000); and "Recent advances in feeding suppressing agents: potential therapeutic strategy for the treatment of obesity, *Exp. Opin. Ther. Patents*, 11: 1677-1692 (2001). The role of neuropeptide Y in obesity is discussed in *Exp. Opin. Invest. Drugs*, 9: 1327-1346 (2000). Cannabinoid receptor ligands are discussed in *Exp. Opin. Invest. Drugs*, 9: 1553-1571 (2000).

The instant invention also includes administration of a single pharmaceutical dosage formulation which contains both a compound of formula I in combination with a second active ingredient, as well as administration of each active agent in its own separate pharmaceutical dosage formulation. Where separate dosage formulations are used, the individual components of the composition can be administered at essentially the same time, i.e., concurrently, or at separately staggered times, i.e. sequentially prior to or subsequent to the administration of the other component of the composition. The instant invention is therefore to be understood to include all such regimes of simultaneous or alternating treatment, and the terms "administration" and "administering" are to be interpreted accordingly. Administration in these various ways are suitable for the present compositions as long as the beneficial pharmaceutical effect of the combination of the compound of formula I and the second active ingredient is realized by the patient at substantially the same time. Such beneficial effect is preferably achieved when the target blood level concentrations of each active ingredient are maintained at substantially the same time. It is preferred that the combination of the compound of formula I and the second active ingredient be co-administered concurrently on a once-a-day dosing schedule; however, varying dosing schedules, such as the compound of formula I once a day and the second active ingredient once, twice or more times per day or the compound of formula I three times a day and the second active ingredient once, twice or more times per day, is also encompassed herein. A single oral dosage formulation comprised of both a compound of formula I and a second active ingredient is preferred. A single dosage formulation will provide convenience for the patient, which is an important consideration especially for patients with diabetes or obese patients who may be in need of multiple medications.

The compounds in the combinations of the present invention may be administered separately, therefore the invention also relates to combining separate pharmaceutical compositions into a kit form. The kit, according to this invention, comprises two separate pharmaceutical compositions: a first unit dosage form comprising a prophylactically or therapeutically effective amount of the compound of formula I, or a pharmaceutically acceptable salt or ester thereof, and a pharmaceutically acceptable carrier or diluent in a first unit dosage form, and a second unit dosage form comprising a prophylactically or therapeutically effective amount of the second active ingredient or drug, or a pharmaceutically acceptable salt or ester thereof, and a pharmaceutically acceptable carrier or diluent in a second unit dosage form. In one embodiment, the kit further comprises a container. Such kits are especially suited for the delivery of solid oral forms such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days or time in the treatment schedule in which the dosages can be administered.

Pharmaceutical Compositions

Another aspect of the present invention provides pharmaceutical compositions which comprise a compound of formula I, as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the typical oral dosage unit form, in which case solid pharmaceutical carriers are typically employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Preparation of Compounds of the Invention

The compounds of formula I of the present invention can be prepared according to the procedures of the following Schemes and Examples, using appropriate materials and are further exemplified by the following specific examples. Moreover, by utilizing the procedures described herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogencarbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. All temperatures are degrees Celsius unless otherwise noted. Mass spectra (MS) were measured by electrospray ion-mass spectroscopy (ESMS).

The phrase "standard peptide coupling reaction conditions" means coupling a carboxylic acid with an amine using an acid activating agent such as EDC, DCC, and HOP in an inert solvent such as dichloromethane in the presence of a catalyst such as HOBT. The use of protecting groups for the amine and carboxylic acid functionalities to facilitate the desired reaction and minimize undesired reactions is well documented. Conditions required to remove protecting groups are found in standard textbooks such as Greene, T. and Wuts, P. G. M., *Protective Groups in Organic Synthesis*, John Wiley & Sons, Inc., New York, N.Y., 1991. CBZ and BOC are commonly used protecting groups in organic synthesis, and their removal conditions are known to those skilled in the art. For example, CBZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of CBZ groups can also be achieved by treatment with a solution of hydrogen bromide in acetic acid or by treatment with a mixture of TFA and dimethylsulfide. Removal of BOC protecting groups is carried out with a strong acid, such as trifluoroacetic acid, hydrochloric acid, or hydrogen chloride gas, in a solvent such as methylene chloride, methanol, or ethyl acetate.

General Methods

Reactions sensitive to moisture or air were performed under nitrogen using anhydrous solvents and reagents. The progress of reactions was determined by either analytical thin layer chromatography (TLC) performed with E. Merck pre-coated TLC plates, silica gel 60E-254, layer thickness 0.25 mm or liquid chromatography-mass spectrum (LC-MS). Analytical HPLC/MS—Standard Method: Mass analysis was performed on a Waters Micromass® ZQ™ with electrospray ionization in positive ion detection mode. For HPLC/MS data, the two HPLC conditions used were as follows: 1) LC2 (Waters C18 XTerra™ 3.5 µm 2.1×20 mm column with gradient 10:90-98:2 v/v $CH_3CN/H_2O$+v 0.05% TFA over 1.25 min then hold at 98:2 v/v $CH_3CN/H_2O$+v 0.05% TFA for 0.75 min; flow rate 1.5 mL/min, UV wavelength 254 nm); and 2) LC4 (Waters C18 XTerra 3.5 µm 2.1×20 mm column with gradient 10:90-98:2 v/v $CH_3CN/H_2O$+v 0.05% TFA over 3.25 min then hold at 98:2 v/v $CH_3CN/H_2O$+v 0.05% TFA for 0.75 min; flow rate 1.5 mL/min, UV wavelength 254 nm). Preparative reverse phase high performance liquid chromatography (RP-HPLC) used for the purification of samples was performed using a Gilson™ RP-HPLC system with an Akzo-Nobel Kromasil™ 100-5C18 column (21.2 mm×10 cm), 25 mL/min gradient elution 10:90 to 100:0 $CH_3CN/H_2O$+v 0.05% TFA over 12 min. Concentration of solutions was carried out on a rotary evaporator under reduced pressure. Flash chromatography was performed using a Biotage Isolera™, Horizon™ or SP1 Flash Chromatography apparatus (Dyax Corp.) on silica gel (32-63 μM particle size, KP-Sil 60 Å packing material type) in pre-packed cartridges or using an ISCO CombiFlash™ Sq 16× or CombiFlash® Companion™ apparatus on silica gel (32-63 μM, 60 Å) in pre-packed cartridges. Microwave reactions were carried out on a Biotage Initiator™ 2.0 or CEM Discover™ system.

Abbreviations Used in the Description of the Preparation of the Compounds of the Present Invention:

ACN is acetonitrile; $Ac_2O$ is acetic anhydride; Ac is acetyl; AcOH is acetic acid; aq is aqueous; Boc and BOC is tert-butoxycarbonyl; $BOC_2O$ is di-tert-butyl Bicarbonate; Bn is benzyl; BuLi is butyl lithium; brine is saturated aqueous sodium chloride solution; CDT is 1,1'-carbonyldiimidazole; Celite™ is diatomaceous earth; $CO_2$ is carbon dioxide; CO is carbon monoxide; DCM or $CH_2Cl_2$ is dichloromethane; dppf is 1,1''-bis(diphenylphosphino)ferrocene; DBU is 1,8-diazabicyclo[5.4.0]undec-7-ene; DEA is diethylamine; DIPEA and DIEA is N,N-diisopropylethylamine; DMAP is 4-N,N-dimethylaminopyridine; DME is 1,2-dimethoxyethane; DMF is N,N-dimethyl-formamide; DMA is N,N-dimethylacetamide; DMSO is dimethyl sulfoxide; EDC is N-ethyl-N'-(3-dimethylaminopropyl)carbodiimide; EtOH is ethyl alcohol; EtOAc is ethyl acetate; Et (et) is ethyl; EA and EtOAc is ethyl acetate; equiv is equivalent(s); ESI is electrospray ionization; $Et_3N$ is triethylamine; $Et_3SiH$ is triethylsilane; EtOH is ethanol; $Et_2O$ or ether is diethyl ether; g is grams; h or hr is hour(s); HATU is O-(7-azabenzotriazol-1-yl)-N,N,N',N'-tetramethyluronium hexafluorophosphate; HBTU is N,N,N',N'-tetramethyl-O-(1H-benzotriazol-1-yl)uronium hexafluorophosphate; HCl is hydrochloric acid; HOAt is 3H-[1,2,3]-triazolo[4,5-b]pyridin-3-ol; HOBT or HOBt is 1-hydroxybenzotriazole; HPLC is high-performance liquid chromatography; HPLC/MS is high-performance liquid chromatography mass spectroscopy; in vacuo is rotary evaporation under reduced pressure; i-Pr is isopropyl; i-PrOH or IPA is isopropyl alcohol; LC is liquid chromatography; LC/MS is liquid chromatography/mass spectroscopy; L is liter(s); m-CPBA is 3-chloroperbenzoic acid; mg is milligrams; ml and mL is milliliter; M is molar; mmol is millimole(s); Me is methyl; MeCN or ACN is acetonitrile; MeOH is methanol; min is minute(s); ms or MS is mass spectrum; MTBE is methyl-tert-butyl ether; μg is microgram(s); μL is microliter(s); N is normal; NaOEt is sodium ethoxide; NaOMe is sodium methoxide; NaOAc is sodium acetate; NMP is N-methyl-2-pyrrolidinone; NMR is nuclear magnetic resonance spectroscopy; NOE is nuclear Overhauser effect; PE is petroleum ether; Ph is phenyl; PTFE is polytetrafluoroethylene; RP or rp is reverse phase; HPLC is high-performance liquid chromatography; RP-HPLC is reverse phase high-performance liquid chromatography; $R_t$ is retention time; RT, r.t. and rt is room temperature; sat., sat'd., and sat is saturated; SF is supercritical fluid; SFC is supercritical fluid chromatography; SFC conditions are supercritical CO2 eluant modified with acetonitrile and/or methanol and/or additional modifiers such as diethylamine using the stated column packing material; TEA is triethyl amine; TFA is trifluoroacetic acid; TFAA is trifluoroacetic anhydride; THF is tetrahydrofuran; TLC is thin layer chromatography; TMS is trimethylsilyl or tetramethylsilane; OTMS is trimethylsilyloxy; TsOH is para-toluene sulfonic acid; v is volume; v/v is volume per volume (ratio); and wt % is weight percent.

The compounds of this invention may be prepared in the manner depicted in the following schemes using methods known in the literature and by the methods outlined in the experimental procedures. The procedures given within this invention are for illustration of how an individual skilled in the art of organic synthesis may prepare the exemplary compounds, and therefore are not limited to the examples shown or to the particular substituents shown.

The required 4-(1,2,4-triazol-5-yl)piperidines were prepared according the general method shown in Scheme 1 (Lin, Y.-I et al *Journal of Heterocyclic Chemistry* 1983, 20, 1693-1695). 1-(tert-Butoxycarbonyl)piperidine-4-carboxylic acid (1-1) was activated using a reagent such as HATU and condensed with a suitable thioamide in the presence of a base such as DIEA. The resulting thioylamide (1-2) is then condensed with a suitable hydrazine under buffered acidic conditions such as NaOAc in acetic acid to afford 1-3. The BOC group is then removed under acidic conditions such as TFA with or without dichloromethane as a co-solvent to afford 1-4.

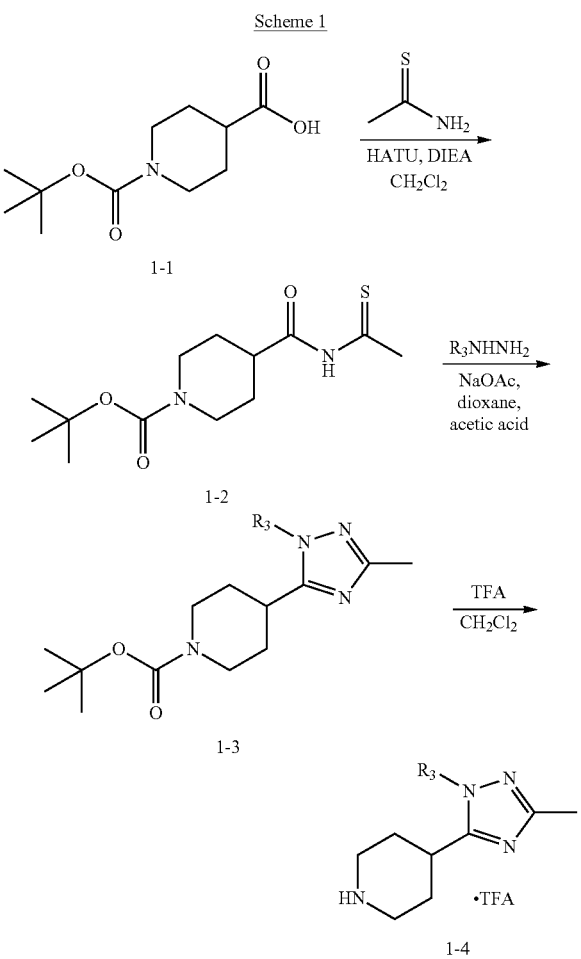

The required 4-(pyrazol-5-yl)piperidines and 4-(pyrazol-3-yl)piperidines were prepared according to the general method shown in Scheme 2. A suitably functionalized tert-butyl 4-(3-oxopropanoyl)piperidine-1-carboxylate (2-1) is condensed under basic conditions to afford a mixture of the pyrazole regioisomers (2-2 and 2-3). The formation of 2-2 and 2-3 can be highly regioselective or can afford mixtures of regioisomers which are separated using chromatography on silica gel or C-18 functionalized silica gel or carried forward as a mixture. The BOC-group is then removed under acidic conditions to afford 2-4 and 2-5 separately or as a mixture which is then separated using chromatography on silica gel or C-18 functionalized solid support.

Scheme 2

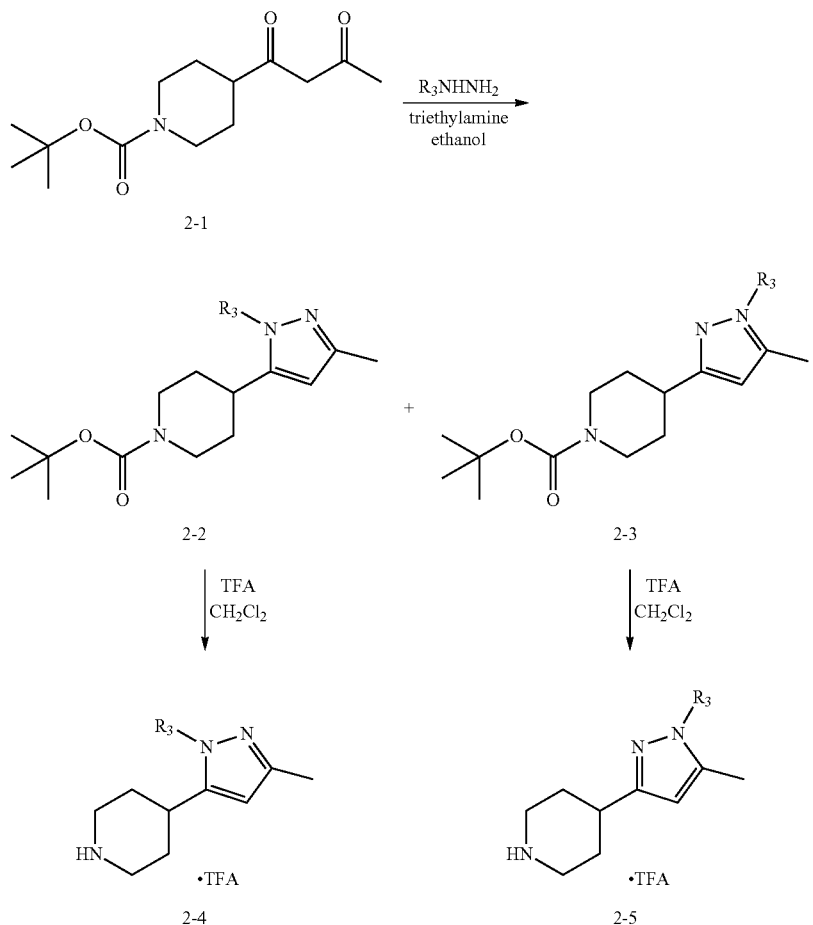

An alternate method for accessing the 4-(pyrazol-5-yl) piperidines and 4-(pyrazol-3-yl)piperidine motifs is shown in Scheme 3. Treatment of a suitably functionalized tert-butyl 4-(3-oxopropanoyl)piperidine-1-carboxylate (3-1) with TFA or other suitably acidic conditions affords the corresponding piperidine 3-2, which is condensed with a suitably functionalized carboxylic acid (3-3) under standard amide formation conditions to afford the amide 3-4. The resulting diketoamide 3-4 is condensed with a suitable hydrazine under basic conditions to afford 3-5 and 3-6. The conversion of 3-4 to 3-5 and 3-6 can be highly regioselective, favoring 3-5 or the mixture can be separated using chromatography on silica gel or C-18 functionalized solid support.

Scheme 3

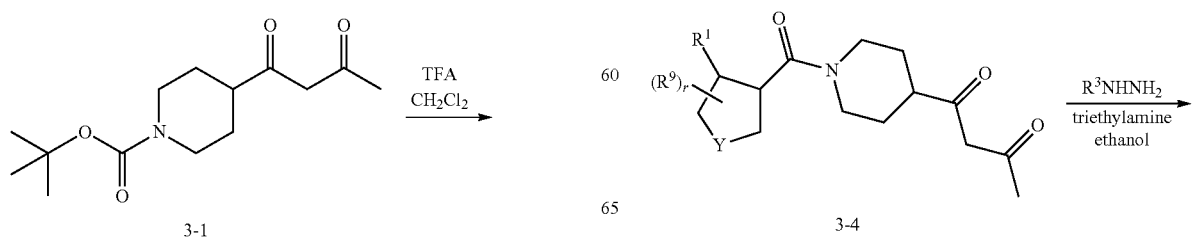

-continued

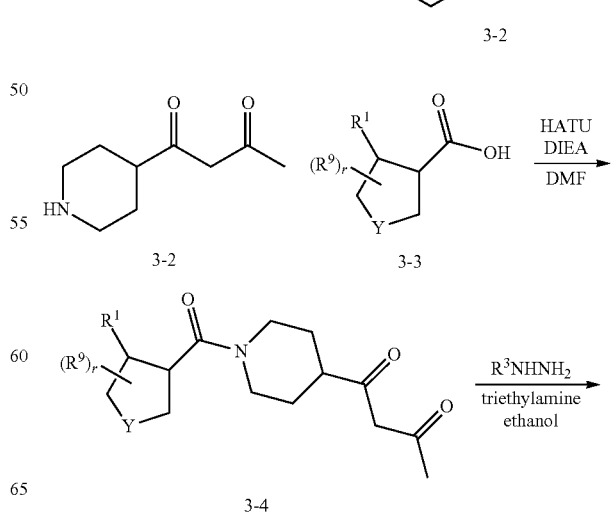

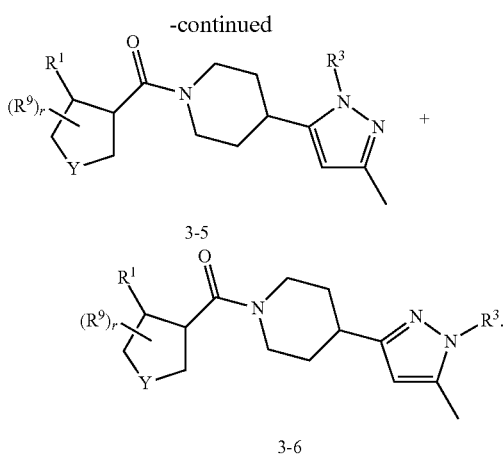

The functionalized piperidines from Scheme 1, 2 and 4 were further derivatized as shown in Scheme 5 using standard amide formation conditions to afford amides sch as 5-3.

Scheme 5

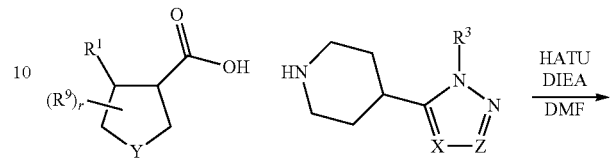

The required 4-(tetrazol-5-yl)piperidines were prepared as shown in Scheme 4. A suitably functionalized carboxylic acid such as 4-1 is condensed with a suitable aniline using standard amide formation conditions to afford 4-2. The amide 4-2 is converted to the tetrazole using literature methods, such as those described in Duncia, J. V. et al., *J. Org. Chem.*, 1991, 56, 2395-2400. Triazole 4-4 is obtained from intermediate 1-3 by basic hydrolysis of the carbamate group.

Scheme 4

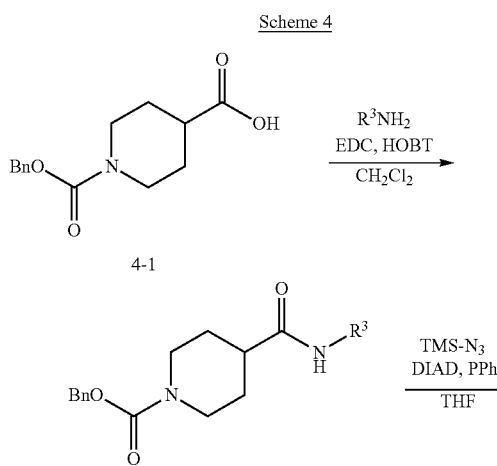

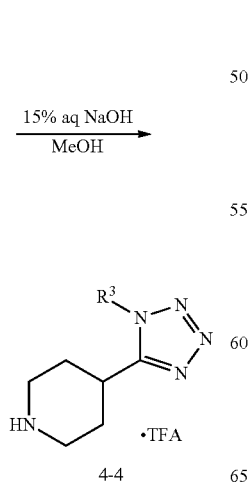

Additional derivatives can be prepared as shown in Scheme 6. A ketone such as 6-1 can be converted to an amine such as 6-2 using standard reductive amination conditions or similar methods of organic synthesis.

Scheme 6

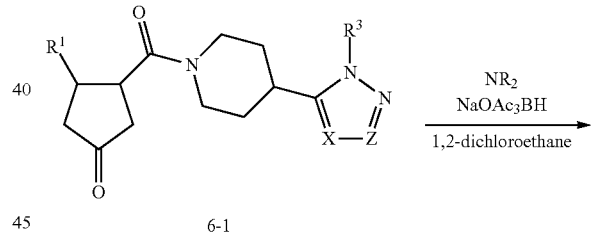

Additional derivatives can also be prepared as shown in Scheme 7. An amine such as 7-1 can be further functionalized by alkylation or acylation conditions or similar methods of organic synthesis.

Scheme 7

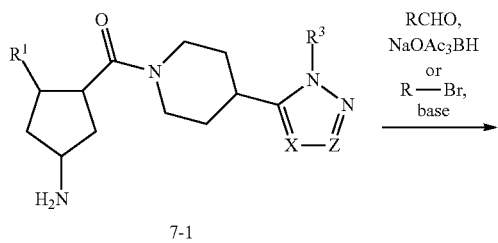

The following Intermediates and Examples are provided to illustrate the invention and are not to be construed as limiting the scope of the invention in any manner.

Intermediate 1

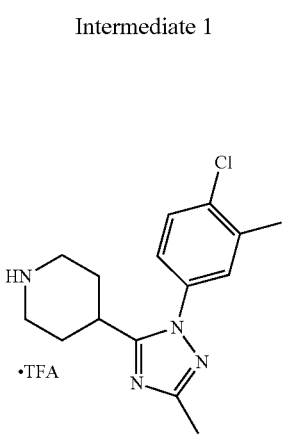

Step A: tert-butyl 4-(ethanethioylcarbamoyl)piperidine-1-carboxylate 1-(tert-Butoxycarbonyl)piperidine-4-carboxylic acid (2.213 g, 9.65 mmol), HATU (4.050 g, 10.65 mmol) and thioacetamide (1.597 g, 21.26 mmol) were mixed in anhydrous dichloromethane (25 mL). The reaction mixture was stirred at room temperature for 30 min. N,N-diisopropyl-N-ethylamine (5.3 mL, 30.3 mmol) was added and the reaction mixture was stirred at room temperature for 16 h. The solution was concentrated and the crude residue was purified on SiO$_2$ (10 to 60% ethyl acetate, hexanes) to afford the title compound, which was used without further purification. HPLC/MS: 112.1 (M−174), R$_t$=3.00 (LC4).

Step B: tert-butyl 4-[1-(4-chloro-3-methylphenyl)-3-methyl-1H-1,2,4-triazol-5-yl]piperidine-1-carboxylate The product from step A (3.09 g, 10.79 mmol), sodium acetate (0.879, 10.7 mmol) and (4-chloro-3-methylphenyl)hydrazine hydrochloride (2.24 g, 11.6 mmol) were mixed in dioxane (25 mL) and acetic acid (25 mL). The reaction mixture was warmed at 90° C. with stirring for 16 h, cooled to rt and the volatiles were removed. Purification of the residue on SiO$_2$ (5 to 60% ethyl acetate, hexanes) afforded the title compound, which was used without further purification. HPLC/MS: 335.0, 337.0 (M−55), R$_t$=3.40 (LC4).

Step C: 4-[1-(4-chloro-3-methylphenyl)-3-methyl-1H-1,2,4-triazol-5-yl]piperidine trifluoroacetate salt The product from step B (145.7 mg, 0.373 mmol) was dissolved in anhydrous dichloromethane (1 mL). Trifluoroacetic acid (100 uL, 1.298 mmol) was added dropwise with stirring. The reaction solution was stirred at room temperature for 16 h. The solution was concentrated and the crude residue was purified by RP-HPLC(C18; acetonitrile, water, 0.1% TFA) to afford the title compound. HPLC/MS: 291.0/ 293.0 (M+1), R$_t$=2.09 (LC4).

Intermediate 2

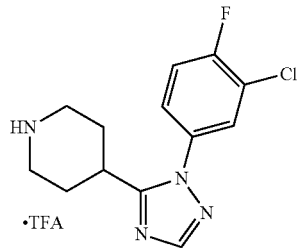 [SMILES: Fc1ccc(-n2ncnc2C2CCNCC2)cc1Cl]

Step A: thioformamide

Phosphorus pentasulfide (603.7 mg, 2.72 mmol) was mixed with formamide (275 uL, 6.9 mmol) in dioxane (12 mL). The suspension was warmed to 102° with stirring for 2 hours. The resulted suspension was filtered and the filter cake was washed with dichloromethane. The combined filtrate was concentrated to afford the crude title compound, which was used without further purification.

Step B: tert-butyl 4-(thioformylcarbamoyl)piperidine-1-carboxylate 1-(tert-butoxycarbonyl)piperidine-4-carboxylic acid (747 mg, 3.26 mmol), HATU (1549 mg, 4.07 mmol) and the product from step A (166 mg, 2.72 mmol) were mixed in anhydrous dichloromethane (5 mL). The reaction mixture was stirred at room temperature for 30 min. N,N-diisopropyl-N-ethylamine (1.423 mL, 8.15 mmol) was added. The reaction mixture was stirred at room temperature for 16 h. The solution was concentrated and the crude was purified on SiO$_2$ (10 to 60% ethyl acetate/hexanes) to afford the title compound. HPLC/MS: 170.1 (M−102), R$_t$=2.91 (LC4).

Step C: tert-butyl 4-[2-(3-chloro-4-fluoro-phenyl)-1,2,4-triazol-3-yl]piperidine-1-carboxylate The product from step B (250 mg, 0.918 mmol), sodium acetate (111.7 mg, 1.362 mmol) and 3-chloro-4-fluorophenylhydrazine hydrochloride (260.65 mg, 1.323 mmol) were mixed in dioxane (1 mL) and acetic acid (1 mL). The reaction mixture was warmed to 90° C. with stirring for 2 hours. The mixture was cooled to rt and the volatiles were removed. The crude product was purified on $SiO_2$ (5 to 60% ethyl acetate/hexanes) to afford the title compound. HPLC/MS: 325.1/327.1 (M-55), $R_t$=3.24 (LC4).

Step D: 4-[1-(3-chloro-4-fluorophenyl)-1H-1,2,4-triazol-5-yl]piperidine trifluoroacetate salt The product from step C (350 mg, 0.919 mmol) was dissolved in dichloromethane (4 mL). Trifluoroacetic acid (1 mL, 12.98 mmol) was added dropwise. The reaction solution was stirred at room temperature for 3 hours. The solution was then concentrated and the crude product was purified by RP-HPLC(C18, 5 to 50% acetonitrile/water+0.05% TFA) to afford the title compound. HPLC/MS: 198.1/200.1 (M-82), $R_t$=2.55 (LC4).

Intermediate 3

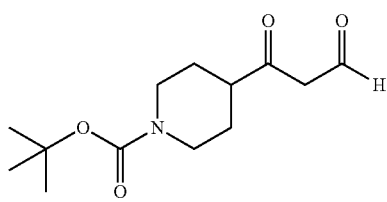 [SMILES: CC(C)(C)OC(=O)N1CCC(C(=O)CC=O)CC1]

Tert-butyl 4-(3-oxopropanoyl)piperidine-1-carboxylate

The title compound was prepared according to the procedure disclosed in US 2002/094989.

Intermediate 4

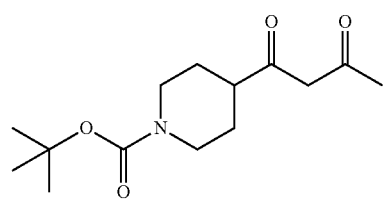 [SMILES: CC(=O)CC(=O)C1CCN(C(=O)OC(C)(C)C)CC1]

Tert-butyl 4-(3-oxobutanoyl)piperidine-1-carboxylate

The title compound was prepared according to the procedure disclosed WO 2006/120478.

Intermediate 5

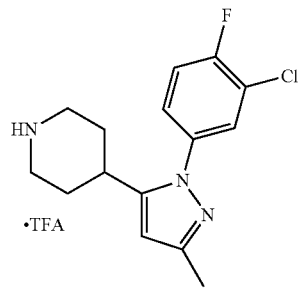 [SMILES: Cc1cc(C2CCNCC2)n(-c2ccc(F)c(Cl)c2)n1]

Step A: tert-butyl 4-[1-(3-chloro-4-fluorophenyl)-3-methyl-1H-pyrazol-5-yl]piperidine-1-carboxylate Intermediate 4 (547.6 mg, 2.033 mmol) and 3-chloro-4-fluorophenylhydrazine hydrochloride (481 mg, 2.44 mmol) were mixed in ethanol (10 mL). Triethylamine (1.134 mL, 8.13 mmol) was added to the reaction mixture. The reaction solution was stirred at room temperature for 16 h. The solution was concentrated and volatiles were removed by azeotroping with toluene to afford the crude title compound. HPLC/MS: 394.3/396.2 (M+1); $R_t$=3.48 min (LC4).

Step B: 4-[1-(3-chloro-4-fluorophenyl)-3-methyl-1H-pyrazol-5-yl]piperidine trifluoroacetate salt The crude product from step A (801 mg, 2.033 mmol) was dissolved in anhydrous dichloromethane (4 mL). Trifluoroacetic acid (2 mL, 26 mmol) was added dropwise. Then the solution was stirred at room temperature for 3 hours. The solution was concentrated and volatiles were removed by azeotroping with toluene. The resulting crude product was purified by RP-HPLC(C18; 5% to 50% acetonitrile/water+0.05% TFA) to afford the title compound. HPLC/MS: 294.1/296.1 (M+1); 2.08 min (LC4).

Intermediate 6

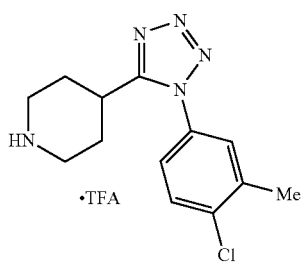 [SMILES: Cc1cc(-n2nnnc2C2CCNCC2)ccc1Cl]

Step A: Benzyl 4-[(4-chloro-3-methyl-phenyl)carbamoyl]piperidine-1-carboxylate 1-Benzyloxycarbonylpiperidine-4-carboxylic acid (1.00 g, 3.80 mmol) and 4-chloro-3-methyl-aniline (0.592 g, 4.18 mmol) in CH$_2$Cl$_2$ (5 mL) were treated with HOBT (0.582, 3.80 mmol) and EDC (1.46 g, 7.60 mmol), and stirred at rt for 16 h. The mixture was directly purified on SiO$_2$ (50 to 100% EtOAc, hexanes) to afford the title compound. HPLC/MS: 387.2/389.1 (M+1); R$_t$=1.22 min (LC2).

Step B: Benzyl 4-[1-(4-chloro-3-methylphenyl)-1H-tetrazol-5-yl]piperidine-1-carboxylate The product from step A (840 mg, 2.171 mmol) and triphenylphosphine (1139 mg, 4.34 mmol) in THF (8.0 ml) was treated with diisopropylazodicarboxylate (0.844 ml, 4.34 mmol) and trimethylsilyl azide (0.574 ml, 4.34 mmol) at rt. The mixture was stirred at rt for 24 h, then quenched with aqueous saturated NaHCO$_3$, and extracted with MTBE. The combined organic layers were concentrated. Purification of the resulting crude product on SiO$_2$ (0 to 100% EtOAc, hexanes) afforded the title compound as a clear colorless oil. HPLC/MS: 412.2/414.1 (M+1); R$_t$=1.22 min (LC2).

Step C: 4-[1-(4-Chloro-3-methylphenyl)-1H-tetrazol-5-yl]piperidine trifluoroacetate salt The product from step B was diluted with MeOH (2 mL) and treated with 15% aq NaOH (2 mL) and then heated by microwave (125° C., 15 min). Then the reaction mixture was cooled to rt, and treated with glacial acetic acid (3 mL). The mixture was concentrated and purified by RP-HPLC (5 to 50% acetonitrile/water+0.05% TFA) to afford the title compound. HPLC/MS: 279.0 (M+1), R$_t$=1.08 (LC2).

Intermediate 7

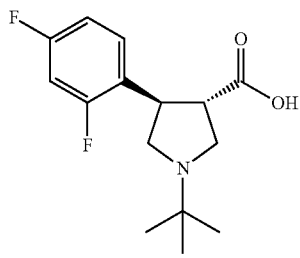 [SMILES: CC(C)(C)N1C[C@@H](C(=O)O)[C@H](c2ccc(F)cc2F)C1]

1-tert-Butyl-4-(2,4-difluorophenyl)pyrrolidine-3-carboxylic acid

The title compound was prepared according to the procedure disclosed in Guo, L. et. Al. *Bioorganic and Medicinal Chemistry Letters* 2008, 18, 3242-3247.

Intermediate 8

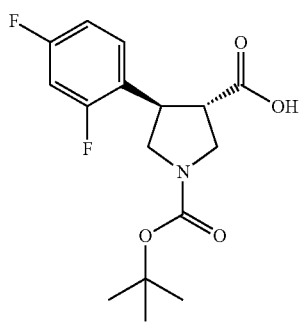 [SMILES: CC(C)(C)OC(=O)N1C[C@@H](C(=O)O)[C@H](c2ccc(F)cc2F)C1]

(3S,4R)-1-tert-Butoxycarbonyl-4-(2,4-difluorophenyl)pyrrolidine-3-carboxylic acid The title compound was prepared according to the procedure disclosed in WO 2008/039418.

Intermediate 9

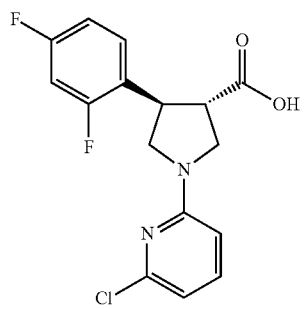 [SMILES: O=C(O)[C@@H]1CN(c2cccc(Cl)n2)C[C@H]1c1ccc(F)cc1F]

Step A: Methyl (3S,4R)-1-(6-chloropyridin-2-yl)-4-(2,4-difluorophenyl)pyrrolidine-3-carboxylate Methyl (3S,4R)-4-(2,4-difluorophenyl)pyrrolidine-3-carboxylate hydrochloride (prepared according to Young, J. R. et. al. *Bioorganic and Medicinal Chemistry Letters* 2007, 17, 5310-5315; 100 mg, 0.360 mmol), 2,6-dichloropyridine (107 mg, 0.720 mmol) and N,N-diisopropyl-N-ethylamine (0.189 ml, 1.080 mmol) in NMP (2.0 ml) was heated by microwave (150° C., 30 min). The mixture was cooled to rt, poured into water and extracted with MTBE. Purification on SiO$_2$ (0 to 30% EtOAc, hexanes) afforded the title compound. HPLC/MS: 353.1/354.9 (M+1); R$_t$=1.22 min (LC2).

Step B: (3S,4R)-1-(6-chloropyridin-2-yl)-4-(2,4-difluorophenyl)pyrrolidine-3-carboxylic acid The product from step A (41 mg, 0.116 mmol) in THF (2.0 ml) was treated with 1M aqueous LiOH (0.349 ml, 0.349 mmol) at rt. The mixture was stirred at rt for 12 h, poured into 2M aq NaHSO$_4$ and extracted with MTBE. The combined organics were dried with anhydrous Na$_2$SO$_4$, filtered and concentrated to afford the title compound which was used without further purification. HPLC/MS: 339.1/340.9 (M+1); R$_t$=1.16 min (LC2).

Intermediate 10

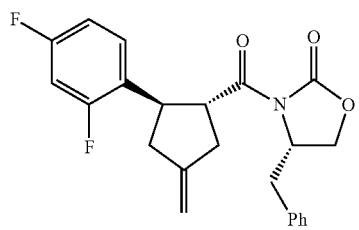 [SMILES: C=C1C[C@@H](C(=O)N2C(=O)OC[C@@H]2Cc2ccccc2)[C@H](c2ccc(F)cc2F)C1]

(5R)-5-benzyl-1-[(1R,2R)-2-(2,4-difluorophenyl)-4-methylenecyclopentanecarbonyl]-pyrrolidin-2-one The title compound was prepared according to the procedure disclosed in WO 2007/047496.

Intermediates 11 an 12

11

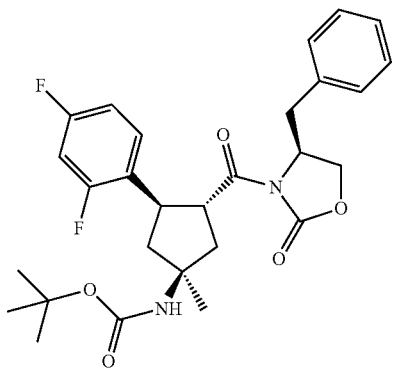

12

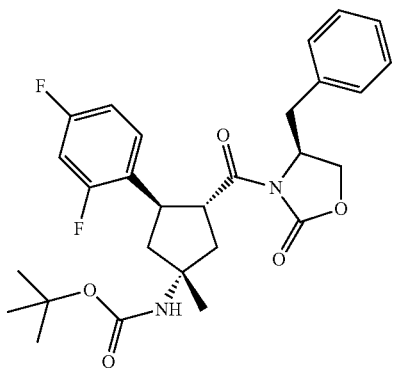

Tert-butyl N-[(1S,3R,4R)-3-[(4S)-4-benzyl-2-oxo-oxazolidine-3-carbonyl]-4-(2,4-difluorophenyl)-1-methyl-cyclopentyl]carbamate and tert-butyl N-[(1R,3R,4R)-3-[(4S)-4-benzyl-2-oxo-oxazolidine-3-carbonyl]-4-(2,4-difluorophenyl)-1-methyl-cyclopentyl]carbamate Step 1: A mixture of Intermediate 10 (15.34 g, 38.7 mmol), chloroacetonitrile (11.68 g, 154.8 mmol) and AcOH (12.58 mL, 304.5 mmol) was cooled in an ice-water bath (temp 5° C.). H$_2$SO$_4$ (12.58 mL, 230 mmol) was added dropwise at 5° C., then the ice-water bath was removed. After about 2 hours, the mixture was treated with ice-NaHCO$_3$ (70.0 g, 0.83 mmol) and extracted with CH$_2$Cl$_2$ (80 mL×3). The combined organic layers were dried over Na$_2$SO$_4$ and concentrated to afford a crude residue.
Step 2: The residue from Step 1 (38.6 g, 78.8 mmol) was treated with thiourea, followed by EtOH (156.4 mL) and AcOH (31.3 mL). The mixture was heated to reflux for about 30 to 45 minutes. Then the reaction was concentrated in vacuo and concentrated twice from toluene (100 mL) to afford a crude residue, which was used without further purification.

Step 3: The residue from step 2 was treated with CH$_2$Cl$_2$ (400 mL) followed by Et$_3$N (32.9 mL, 236 mmol), 5% NaOH (62.5 mL) and Boc$_2$O (20.6 g, 94.6 mmol). Then the reaction was stirred for 2 h. The reaction mixture was diluted with water then extracted with CH$_2$Cl$_2$ (250 mL×3). Purification by silica gel chromatography (petroleum ether: ethyl acetate=10:1) gave Intermediate 11, HPLC/MS: 459.1 (M-55); R$_t$=2.50 min (LC4) and Intermediate 12. HPLC/MS: 515.2 (M+1); R$_t$=2.50 min (LC4).

Intermediate 13

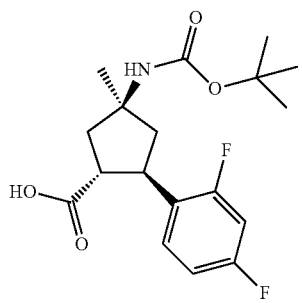 [SMILES: CC(C)(C)OC(=O)N[C@]1(C)C[C@@H](C(=O)O)[C@H](c2ccc(F)cc2F)C1]

(1R,2R,4S)-4-(tert-butoxycarbonylamino)-2-(2,4-difluorophenyl)-4-methyl-cyclopentanecarboxylic acid Intermediate 11 (5 g, 9.72 mmol) in THF (20 ml) cooled to 0° C. and treated with hydrogen peroxide (2.55 ml, 29.2 mmol) and LiOH (19.43 ml, 19.43 mmol). The reaction was allowed to warm to rt, and then stirred for 12 h at rt. The reaction was poured into water, washed with ethyl acetate and the washings were discarded. The aqueous portion was acidified (pH<2) with 2 M aqueous NaHSO$_4$ and extracted with ethyl acetate. The combined ethyl acetate extracts were dried with anhydrous Na$_2$SO$_4$, and filtered. The filtrate was concentrated to afford the title compound. HPLC/MS: 356.2 (M+1); R$_t$=1.15 min (LC2).

Intermediate 14

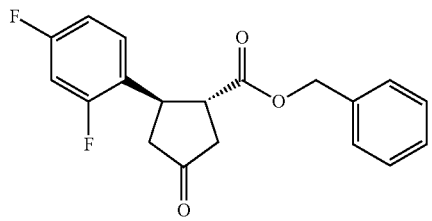 [SMILES: O=C1C[C@@H](C(=O)OCc2ccccc2)[C@H](c2ccc(F)cc2F)C1]

Benzyl (1R,2R)-2-(2,4-difluorophenyl)-4-oxo-cyclopentanecarboxylate

The title compound was prepared according to the procedure disclosed in WO 2007/047496.

Intermediate 15

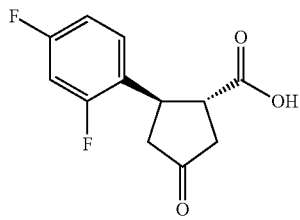 [SMILES: O=C1C[C@@H](C(=O)O)[C@H](c2ccc(F)cc2F)C1]

(1R,2R)-2-(2,4-difluorophenyl)-4-oxo-cyclopentanecarboxylic acid

Intermediate 14 (500 mg, 1.514 mmol) was added to a THF (6 mL) suspension of Pd/C (32.2 mg). The suspension was flushed with $N_2$ and then $H_2$ (1 atm), and then stirred under $H_2$ at rt for 12 h. Then the suspension was filtered through a 0.45 micrometer PTFE syringe filter and the resulting filtrate was concentrated to afford the title compound. HPLC/MS: 241.01 (M+1); $R_t$=0.76 min (LC2).

Intermediates 16 and 17

16

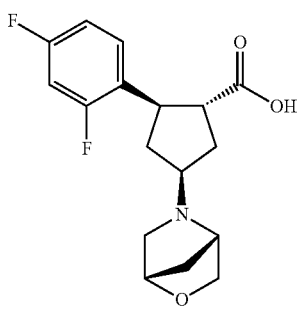

17

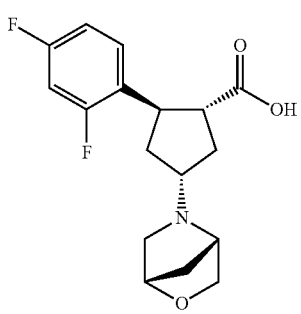

(1R,2R,4S)-2-(2,4-difluorophenyl)-4-[(1S,4S)-2-oxa-5-azabicyclo[2.2.1]heptan-5-yl]cyclopentanecarboxylic acid and (1R,2R,4R)-2-(2,4-difluorophenyl)-4-[(1S,4S)-2-oxa-5-azabicyclo[2.2.1]heptan-5-yl] cyclopentanecarboxylic acid The title compounds were prepared according to the procedure disclosed in WO2007/047496.

Intermediate 18

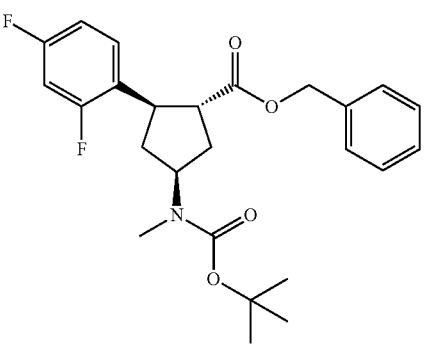 [SMILES: CN(C(=O)OC(C)(C)C)[C@@H]1C[C@@H](C(=O)OCc2ccccc2)[C@H](c2ccc(F)cc2F)C1]

Benzyl (1R,2R,4S)-4-(tert-butoxycarbonyl(methyl) amino)-2-(2,4-difluorophenyl)-cyclopentanecarboxylate The title compound was prepared according to the procedure disclosed in WO 2007/047496.

Intermediate 19

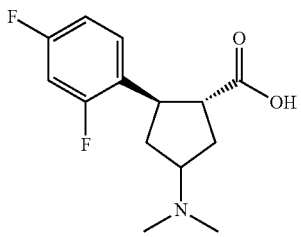 [SMILES: CN(C)C1C[C@@H](C(=O)O)[C@H](c2ccc(F)cc2F)C1]

(1R,2R-2-(2,4-difluorophenyl)-4-dimethylamino-cyclopentanecarboxylic acid

The title compound was prepared according to the procedure disclosed in WO 2002/067869.

Intermediate 20

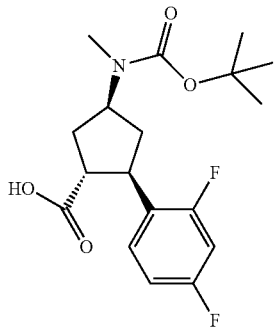 [SMILES: CN(C(=O)OC(C)(C)C)[C@@H]1C[C@@H](C(=O)O)[C@H](c2ccc(F)cc2F)C1]

(1R,2R,4S)-4-tert-butoxycarbonyl)methyl)amino-2-(2,4-difluorophenyl)cyclopentane-carboxylic acid A flask containing Intermediate 18 (500 mg, 1.122 mmol) and 5% Pd/C (30 mg) in THF (3.0 ml) was purged with $N_2$ then $H_2$ (1 atm). The mixture was stirred at rt under $H_2$ (1 atm) for 24 h, and then filtered. The filtrate was concentrated to afford the title compound. HPLC/MS: 356.2 (M+1); $R_t$=1.13 min (LC2).

Intermediate 21

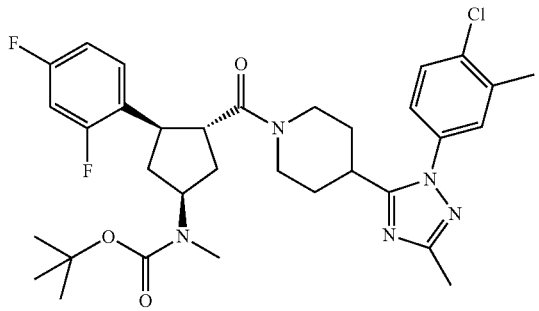 [SMILES: Cc1nc(C2CCN(C(=O)[C@@H]3C[C@@H](N(C)C(=O)OC(C)(C)C)C[C@H]3c3ccc(F)cc3F)CC2)n(-c2ccc(Cl)c(C)c2)n1]

Tert-butyl N-[(1S,3R,4R)-3-[4-[2-(4-chloro-3-methyl-phenyl)-5-methyl-1,2,4-triazol-3-yl]piperidine-1-carbonyl]-4-(2,4-difluorophenyl)cyclopentyl]-N-methyl-carbamate A mixture of Intermediate 20 (398 mg, 1.120 mmol), Intermediate 1 (358 mg, 1.232 mmol), HBTU (510 mg, 1.344 mmol) and triethylamine (0.156 ml, 1.120 mmol) in DMF (4 ml) was stirred at rt for 16 h. The crude reaction mixture was purified by RP-HPLC(C18, acetonitrile, $H_2O$, 0.05% TFA) to afford the title compound. HPLC/MS: 628.3/629.7 (M+1); $R_t$=1.23 min (LC2).

Intermediate 22

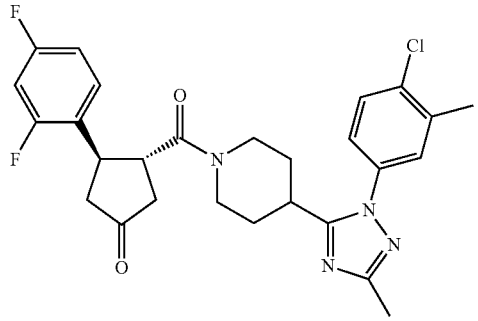 [SMILES: Cc1nc(C2CCN(C(=O)[C@@H]3CC(=O)C[C@H]3c3ccc(F)cc3F)CC2)n(-c2ccc(Cl)c(C)c2)n1]

(3R,4R)-3-[4-[2-(4-chloro-3-methyl-phenyl)-5-methyl-1,2,4-triazol-3-yl]piperidine-1-carbonyl]-4-(2,4-difluorophenyl)cyclopentanone Intermediate 15 (362 mg, 1.507 mmol) and Intermediate 1 (732 mg, 1.808 mmol) in $CH_2Cl_2$ (4.0 ml) were treated with HBTU (686 mg, 1.808 mmol) and triethylamine (0.462 ml, 3.32 mmol) at rt. The reaction was stirred at rt for 12 h, and then quenched with aqueous $NaHCO_3$ and extracted with MTBE. The combined organic layers were dried with $Na_2SO_4$, filtered and concentrated. Purification of the resulting residue on $SiO_2$ (0 to 10% MeOH, $CH_2Cl_2$) afforded the title compound. HPLC/MS: 513.2/515.1 (M+1); $R_t$=1.14 min (LC2).

Intermediate 23

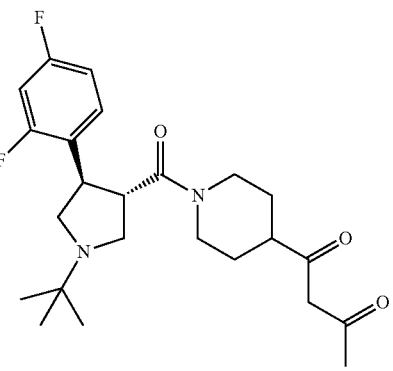

1-(1-{[(3S,4R)-1-tert-butyl-4-(2,4-difluorophenyl)pyrrolidin-3-yl]carbonyl}piperidin-4-yl)butane-1,3-dione Step A: 1-(4-piperidyl)butane-1,3-dione trifluoroacetate salt Intermediate 4 (1.2409 g, 4.61 mmol) was dissolved in dichloromethane (6 mL) and treated at rt with trifluoroacetic acid (2 mL, 26 mmol). The reaction was stirred at room temperature for 3 h. Then the volatiles were removed to afford the title compound. HPLC/MS: 112.0 (M-57); $R_t$=0.33 min (LC4).

Step B: 1-(1-{[(3S,4R)-1-tert-butyl-4-(2,4-difluorophenyl)pyrrolidin-3-yl]carbonyl}piperidin-4-yl)butane-1,3-dione Intermediate 7 (1.60 g, 5.00 mmol) and HATU (2.20 g, 5.78 mmol) were dissolved in DMF (24 mL). The solution was stirred for 15 minutes and then treated with the product from step A (1.31 g, 4.61 mmol) and N,N-diisopropyl-N-ethylamine (2.53 mL, 14.5 mmol). The mixture was stirred at room temperature for 16 h. The reaction mixture was partitioned between dichloromethane and water, and the organic phase was separated and concentrated. The resulting crude residue was purified by RP-HPLC (C18, acetonitrile, water, 10 to 100% over 12 min, 0.1% TFA) to afford the title compound. HPLC/MS: 435.4 (M+1); $R_t$=2.3 min (LC4).

EXAMPLE 1

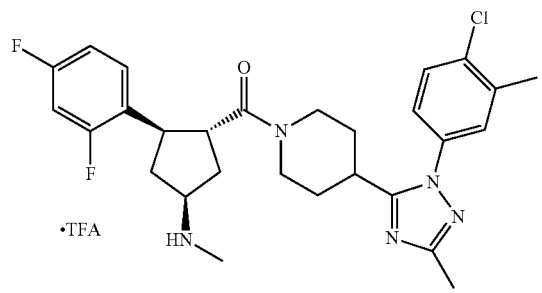 [SMILES: CN[C@@H]1C[C@@H](C(=O)N2CCC(c3nc(C)nn3-c3ccc(Cl)c(C)c3)CC2)[C@H](c2ccc(F)cc2F)C1]

[4-[2-(4-chloro-3-methyl-phenyl)-5-methyl-1,2,4-triazol-3-yl]-1-piperidyl]-[(1R,2R)-2-(2,4-difluorophenyl)-4-methylamino-cyclopentyl]methanone trifluoroacetate salt Intermediate 21 (20 mg, 0.032 mmol) was treated with TFA and DCM (1:1, 2 mL), and stirred at rt for 6 h. The reaction mixture was concentrated and the resulting residue was purified by RP-HPLC(C-18, acetonitrile, H₂O, 10 to 100% over 12 min, 0.05% TFA) to afford the title compound. HPLC/MS: 528.3/530.3 (M+1); $R_t$=1.66 min (LC4).

EXAMPLE 2

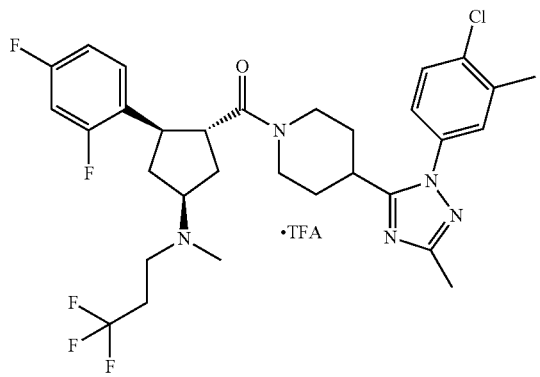 [SMILES: Cc1nc(C2CCN(C(=O)[C@@H]3C[C@@H](N(C)CCC(F)(F)F)C[C@H]3c3ccc(F)cc3F)CC2)n(-c2ccc(Cl)c(C)c2)n1]

[4-[2-(4-chloro-3-methyl-phenyl)-5-methyl-1,2,4-triazol-3-yl]-1-piperidyl]-[(1R,2R,4S)-2-(2,4-difluorophenyl)-4-(methyl(3,3,3-trifluoropropyl)amino)cyclopentyl]methanone trifluoroacetate salt The product from Example 1 (30 mg, 0.047 mmol) and potassium carbonate (32.3 mg, 0.234 mmol) in acetonitrile (2 mL) was treated at rt with 3-bromo-1,1,1-trifluoropropane (16.54 mg, 0.093 mmol). The reaction was stirred at 60° C. until complete. Then the reaction mixture was filtered and purified by RP-HPLC(C-18, acetonitrile, H₂O, 10 to 100% over 12 min, 0.05% TFA) to afford title compound. HPLC/MS: 624.3/626.1 (M+1); $R_t$=1.14 min (LC2).

EXAMPLE 3

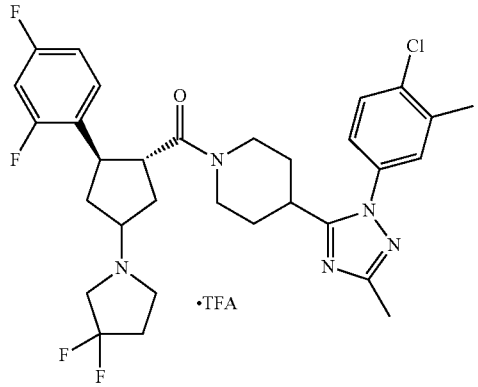 [SMILES: Cc1nc(C2CCN(C(=O)[C@@H]3CC(N4CCC(F)(F)C4)C[C@H]3c3ccc(F)cc3F)CC2)n(-c2ccc(Cl)c(C)c2)n1]

[4-[2-(4-chloro-3-methyl-phenyl)-5-methyl-1,2,4-triazol-3-yl]-1-piperidyl]-[(1R,2R)-2-(2,4-difluorophenyl)-4-(3,3-difluoropyrrolidin-1-yl)cyclopentyl]methanone trifluoroacetate salt Intermediate 22 (50 mg, 0.097 mmol), 3,3-difluoropyrrolidine hydrochloride (70.0 mg, 0.487 mmol), sodium triacetoxyborohydride (103 mg, 0.487 mmol) and sodium acetate (19.99 mg, 0.244 mmol) in 1,2-dichloroethane (1.0 ml) were stirred at rt for 4 h. Then the reaction was quenched with 2M aqueous NaOH and extracted with MTBE. The organic portions were combined and concentrated. Purification of the resulting residue by RP-HPLC(C-18, acetonitrile, H₂O, 10 to 100% over 12 min, 0.05% TFA) afforded the title compound. HPLC/MS: 604.2/605.6 (M+1); 1.76 min (LC2).

EXAMPLE 4

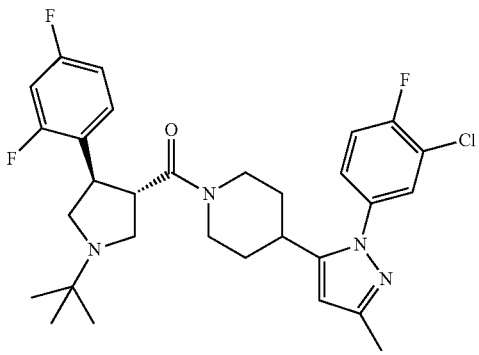 [SMILES: Cc1cc(C2CCN(C(=O)[C@@H]3CN(C(C)(C)C)C[C@H]3c3ccc(F)cc3F)CC2)n(-c2ccc(F)c(Cl)c2)n1]

[(3S,4R)-1-tert-butyl-4-(2,4-difluorophenyl)pyrrolidin-3-yl]{4-[1-(3-chloro-4-fluorophenyl)-3-methyl-1H-pyrazol-5-yl]piperidin-1-yl}methanone Intermediate 23 (23.4 mg, 0.043 mmol) and 3-chloro-4-fluorophenylhydrazine hydrochloride (11.4 mg, 0.071 mmol) were mixed in ethanol (1 mL). Then N,N-diisopropyl-N-ethylamine (25 uL, 0.143 mmol) was added and the reaction was stirred at room temperature until it was complete. Then the reaction mixture was concentrated and the resulting crude product was purified with RP-HPLC(C-18, acetonitrile, H₂O, 10 to 100% over 12 min, 0.05% TFA) to afford the title compound. HPLC/MS: 559.4/561.4 (M+1); $R_t$=2.86 min (LC4).

EXAMPLE 5

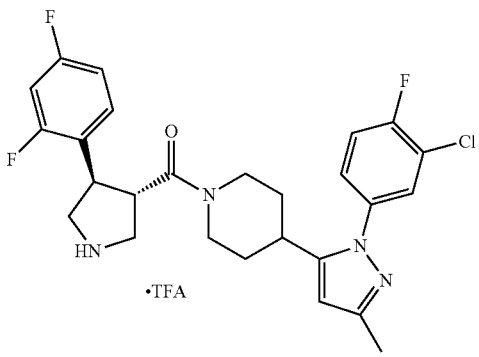 [SMILES: Cc1cc(C2CCN(C(=O)[C@@H]3CNC[C@H]3c3ccc(F)cc3F)CC2)n(-c2ccc(F)c(Cl)c2)n1]

Step A: tert-butyl (3S,4R)-3-({4-[1-(3-chloro-4-fluorophenyl)-3-methyl-1H-pyrazol-5-yl]piperidin-1-yl}carbonyl)-4-(2,4-difluorophenyl)pyrrolidine-1-carboxylate A mixture of Intermediate 8 (75 mg, 0.229 mmol) and Intermediate 5 (93 mg, 0.229 mmol) in DMA (1 ml) were treated with HBTU (130 mg, 0.344 mmol) and triethylamine (70 mg, 0.687 mmol) at rt. The reaction was stirred at rt until it was complete. Then the reaction mixture was diluted with aqueous DMSO and purified by RP-HPLC (C18, acetonitrile, H₂O, 10 to 100% over 12 min, 0.05% TFA) to afford the title compound. HPLC/MS: 603.2/605.2 (M+1); $R_t$=2.25 min (LC4).

Step B: [4-[2-(3-chloro-4-fluoro-phenyl)-5-methyl-pyrazol-3-yl]-1-piperidyl]-[(3S,4R)-4-(2,4-difluorophenyl)pyrrolidin-3-yl]methanone trifluoroacetate salt The product from step A was dissolved in CH₂Cl₂ (5 mL) and treated with TFA (2.5 mL). The mixture was stirred at rt for 6 h, concentrated and purified by RP-HPLC (C-18, acetonitrile, H₂O, 10 to 100% over 12 min, 0.05% TFA) to afford the title compound. HPLC/MS: 503.2/505.2 (M+1); $R_t$=1.62 min (LC4).

EXAMPLE 6

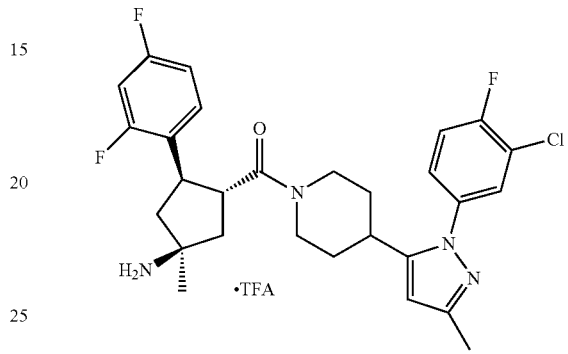

[(1R,2R,4S)-4-amino-2-(2,4-difluorophenyl)-4-methylcyclopentyl]{4-[1-(3-chloro-4-fluorophenyl)-3-methyl-1H-pyrazol-5-yl]piperidin-1-yl}methanone trifluoroacetate salt The title compound was prepared in a similar manner to Example 5 from Intermediate 13 and Intermediate 5 to afford the title compound. HPLC/MS: 531.2/533.2 (M+1); $R_t$=1.09 min (LC2).

EXAMPLE 7

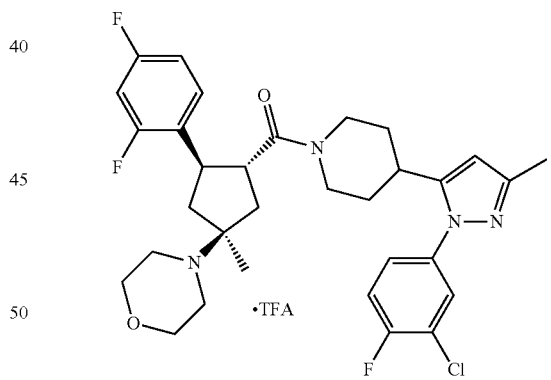

{4-[1-(3-chloro-4-fluorophenyl)-3-methyl-1H-pyrazol-5-yl]piperidin-1-yl}[(1R,2R,4S)-2-(2,4-difluorophenyl)-4-methyl-4-(morpholin-4-yl)cyclopentyl]methanone trifluoroacetate salt The product from Example 6 (17.2 mg, 0.027 mmol) in DMA (1 mL) was treated with cesium carbonate (63.3 mg, 0.194 mmol) and 2-iodoethyl ether (15.8 mg, 0.049 mmol) at rt. The mixture was heated at 110° C. for 16 h, then cooled to rt and filtered. The filtrate was directly purified by RP-HPLC (15 to 100% acetonitrile/water+0.05% TFA) to afford the title compound. HPLC/MS: 601.4/603.4 (M+1); $R_t$=2.92 min (LC4).

EXAMPLE 8

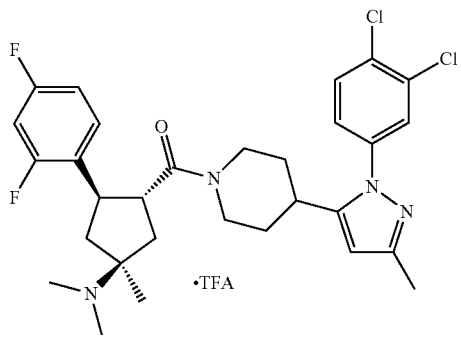 [SMILES: Cc1cc(C2CCN(C(=O)[C@@H]3C[C@@](C)(N(C)C)C[C@H]3c3ccc(F)cc3F)CC2)n(-c2ccc(Cl)c(Cl)c2)n1]

{4-[1-(3,4-dichlorophenyl)-3-methyl-1H-pyrazol-5-yl]piperidin-1-yl}[(1R,2R,4S)-2-(2,4-difluorophenyl)-4-(dimethylamino)-4-methylcyclopentyl]methanone trifluoroacetate salt

[(1R,2R,4S)-4-amino-2-(2,4-difluorophenyl)-4-methylcyclopentyl]{4-[1-(3,4-dichlorophenyl)-3-methyl-1H-pyrazol-5-yl]piperidin-1-yl}methanone trifluoroacetate salt (54.5 mg, 0.082 mmol; prepared in a similar manner to Example 6 in dioxane (0.25 mL) was treated with 96 wt % aqueous formic acid (0.044 mL, 1.10 mmol) and 34 wt % aqueous formaldehyde (0.089 mL, 1.10 mmol). The mixture was heated at 100° C. for 1 h. Then the mixture was cooled to rt and directly purified by RP-HPLC (C18, 20% to 70% acetonitrile/water+0.05% TFA) to afford the title compound. HPLC/MS: 575.3/577.4 (M+1); $R_t$=2.98 min (LC4).

The Examples in Table 1 were prepared according to procedures of for Examples 1-8, using the appropriate intermediates.

TABLE 1

| Example Number | Structure | Calc'd Exact Mass (Parent) | Parent ion m/z (ESI-MS); $R_t$ (LC method) |
|---|---|---|---|
| 9 [4-[2-(4-chloro-3-methyl-phenyl)-5-methyl-1,2,4-triazol-3-yl]-1-piperidyl]-[(1R,2R,4R)-2-(2,4-difluorophenyl)-4-(methyl-(3,3,3-trifluoropropyl)-amino)cyclopentyl]methanone trifluoroacetate salt | 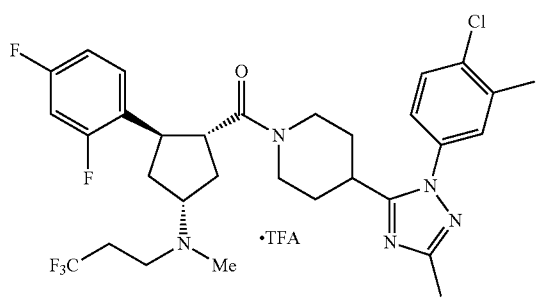 [SMILES: Cc1nc(C2CCN(C(=O)[C@@H]3C[C@H](N(C)CCC(F)(F)F)C[C@H]3c3ccc(F)cc3F)CC2)n(-c2ccc(Cl)c(C)c2)n1] | 623.2 | 624.3/626.1 (M + 1); 1.79 min (LC4) |
| 10 [4-[2-(4-chloro-3-methyl-phenyl)-5-methyl-1,2,4-triazol-3-yl]-1-piperidyl]-[(1R,2R,4S)-2-(2,4-difluorophenyl)-4-(methyl-(2,2,2-trifluoroethyl)amino)-cyclopentyl]methanone trifluoroacetate salt | 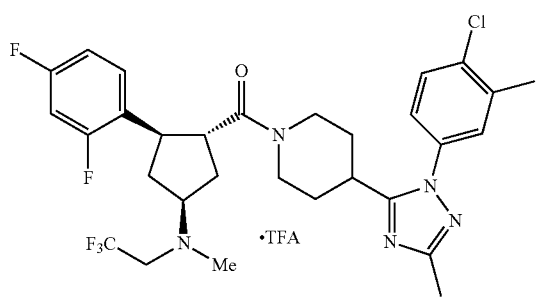 [SMILES: Cc1nc(C2CCN(C(=O)[C@@H]3C[C@@H](N(C)CC(F)(F)F)C[C@H]3c3ccc(F)cc3F)CC2)n(-c2ccc(Cl)c(C)c2)n1] | 609.2 | 610.3/611.9 (M + 1); 1.16 (LC2) |
| 11 [4-[2-(4-chloro-3-methyl-phenyl)-5-methyl-1,2,4-triazol-3-yl]-1-piperidyl]-[(1R,2R,4S)-2-(2,4-difluorophenyl)-4-(2-fluoroethyl(methyl)amino)cyclopentyl]methanone trifluoroacetate salt | 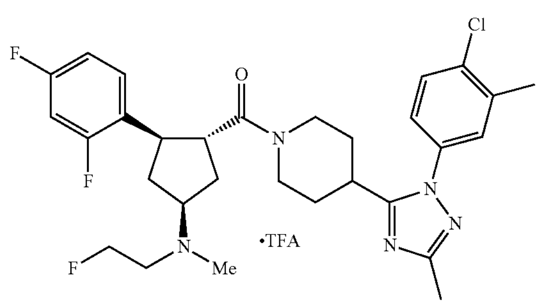 [SMILES: Cc1nc(C2CCN(C(=O)[C@@H]3C[C@@H](N(C)CCF)C[C@H]3c3ccc(F)cc3F)CC2)n(-c2ccc(Cl)c(C)c2)n1] | 573.2 | 574.3/575.9 (M + 1); 1.11 min (LC2) |

TABLE 1-continued

| Example Number | Structure | Calc'd Exact Mass (Parent) | Parent ion m/z (ESI-MS); R$_t$ (LC method) |
|---|---|---|---|
| 12 [4-[2-(4-chloro-3-methyl-phenyl)-5-methyl-1,2,4-triazol-3-yl]-1-piperidyl]-[(1R,2R,4R)-2-(2,4-difluorophenyl)-4-morpholinocyclopentyl]-methanone trifluoroacetate salt | 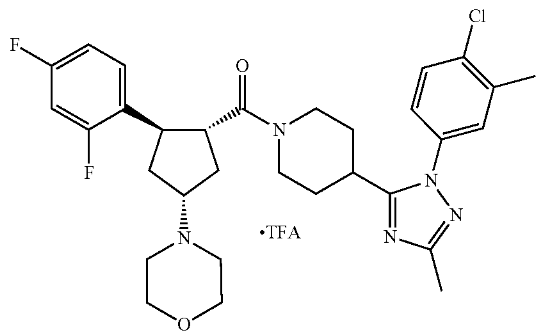 [SMILES: Cc1nc(C2CCN(C(=O)[C@@H]3C[C@H](N4CCOCC4)C[C@H]3c3ccc(F)cc3F)CC2)n(-c2ccc(Cl)c(C)c2)n1] | 583.3 | 584.3/586.4 (M + 1); 1.66 min (LC4) |
| 13 [4-[2-(4-chloro-3-methyl-phenyl)-5-methyl-1,2,4-triazol-3-yl]-1-piperidyl]-[(1R,2R,4S)-2-(2,4-difluorophenyl)-4-morpholinocyclopentyl]-methanone trifluoroacetate salt | 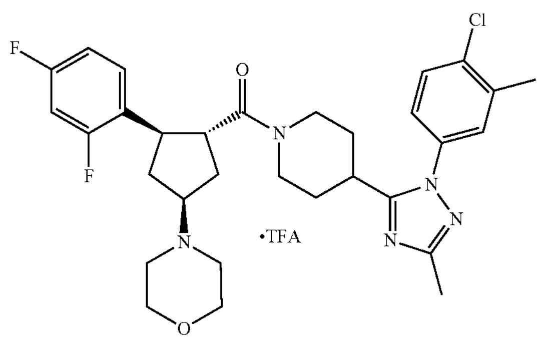 [SMILES: Cc1nc(C2CCN(C(=O)[C@@H]3C[C@@H](N4CCOCC4)C[C@H]3c3ccc(F)cc3F)CC2)n(-c2ccc(Cl)c(C)c2)n1] | 583.3 | 584.3/586.4 (M + 1); 1.66 min (LC4) |
| 14 [4-[2-(4-chloro-3-methyl-phenyl)-5-methyl-1,2,4-triazol-3-yl]-1-piperidyl]-[(1R,2R,4R)-2-(2,4-difluorophenyl)-4-dimethyl-amino-cyclo-pentyl]-methanone trifluoroacetate salt | 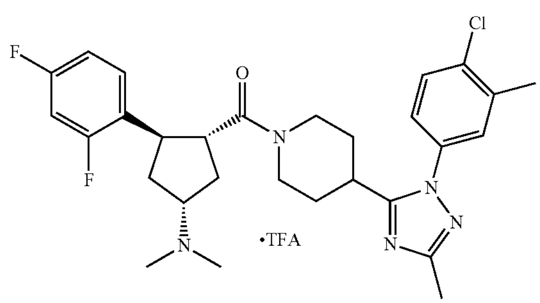 [SMILES: Cc1nc(C2CCN(C(=O)[C@@H]3C[C@H](N(C)C)C[C@H]3c3ccc(F)cc3F)CC2)n(-c2ccc(Cl)c(C)c2)n1] | 541.2 | 542.4/544.1 (M + 1); 1.08 (L2) |
| 15 [4-[2-(4-chloro-3-methyl-phenyl)-5-methyl-1,2,4-triazol-3-yl]-1-piperidyl]-[(1R,2R,4S)-2-(2,4-difluoro-phenyl)-4-dimethylamino-cyclopentyl]methanone trifluoroacetate salt | 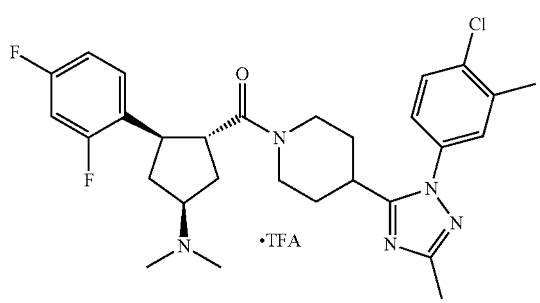 [SMILES: Cc1nc(C2CCN(C(=O)[C@@H]3C[C@@H](N(C)C)C[C@H]3c3ccc(F)cc3F)CC2)n(-c2ccc(Cl)c(C)c2)n1] | 541.2 | 542.3/544.3 (M + 1); 1.65 (LC4) |

TABLE 1-continued

| Example Number | Structure | Calc'd Exact Mass (Parent) | Parent ion m/z (ESI-MS); R_t (LC method) |
|---|---|---|---|
| 16 {4-[1-(4-chloro-3-methylphenyl)-3-methyl-1H-1,2,4-triazol-5-yl]piperidin-1-yl}{(1R,2R)-2-(2,4-difluorophenyl)-4-[(2-phenylpropan-2-yl)amino]-cyclopentyl}methanone trifluoroacetate salt | 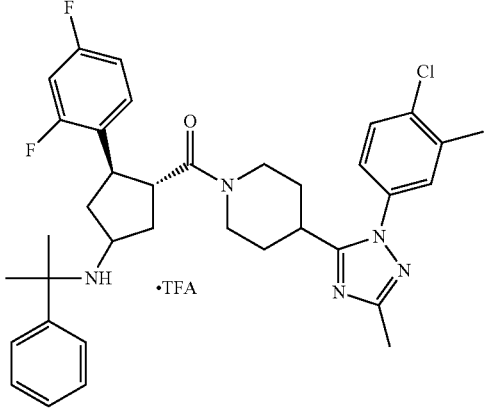 [SMILES: Cc1nc(C2CCN(C(=O)[C@@H]3CC(NC(C)(C)c4ccccc4)C[C@H]3c3ccc(F)cc3F)CC2)n(-c2ccc(Cl)c(C)c2)n1] | 631.3 | 513.2/515.3 (M − 118); 1.93 (LC4) |
| 17 [(1R,2R)-4-(tert-butyl-amino)-2-(2,4-difluoro-phenyl)cyclopentyl]{4-[1-(4-chloro-3-methylphenyl)-3-methyl-1H-1,2,4-triazol-5-yl]piperidin-1-yl}methanone trifluoroacetate salt | 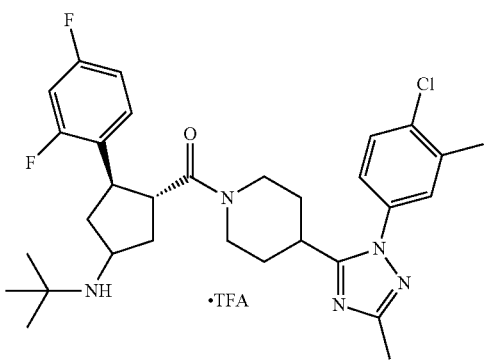 [SMILES: Cc1nc(C2CCN(C(=O)[C@@H]3CC(NC(C)(C)C)C[C@H]3c3ccc(F)cc3F)CC2)n(-c2ccc(Cl)c(C)c2)n1] | 569.3 | 513.2/515.2 (M − 56); 1.92 (LC4) |
| 18 {4-[1-(4-chloro-3-methyl-phenyl)-3-methyl-1H-1,2,4-triazol-5-yl]piperidin-1-yl}[(1R,2R)-4-(cyclobutyl-amino)-2-(2,4-difluoro-phenyl)cyclopentyl]methanone trifluoroacetate salt | 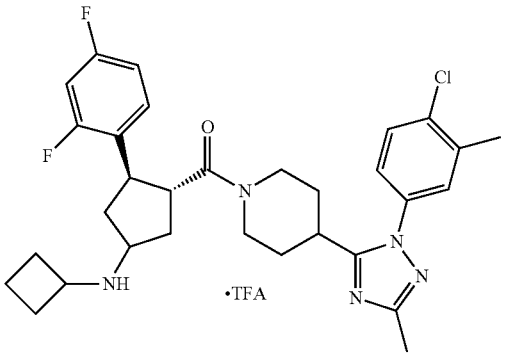 [SMILES: Cc1nc(C2CCN(C(=O)[C@@H]3CC(NC4CCC4)C[C@H]3c3ccc(F)cc3F)CC2)n(-c2ccc(Cl)c(C)c2)n1] | 567.3 | 568.3/569.7 (M + 1); 1.79 (LC4) |
| 19 {4-[1-(4-chloro-3-methyl-phenyl)-3-methyl-1H-1,2,4-triazol-5-yl]piperidin-1-yl}{(1R,2R)-2-(2,4-difluoro-phenyl)-4-[(2-methoxy-ethyl)amino]cyclopentyl}methanone trifluoroacetate salt | 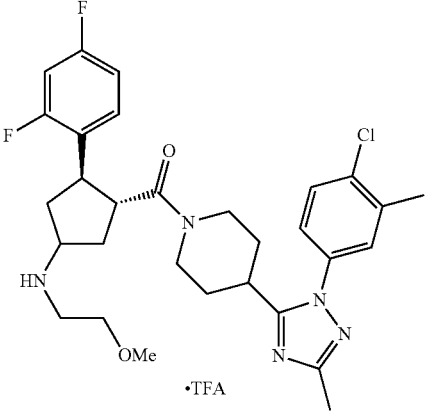 [SMILES: COCCNC1C[C@@H](C(=O)N2CCC(c3nc(C)nn3-c3ccc(Cl)c(C)c3)CC2)[C@H](c2ccc(F)cc2F)C1] | 571.3 | 572.3/573.7 (M + 1); 1.71 min (LC4) |

TABLE 1-continued

| Example Number | Structure | Calc'd Exact Mass (Parent) | Parent ion m/z (ESI-MS); R$_t$ (LC method) |
|---|---|---|---|
| 20 [4-[2-(4-chloro-3-methyl-phenyl)-5-methyl-1,2,4-triazol-3-yl]-1-piperidyl]-[(1R,2R)-2-(2,4-difluoro-phenyl)-4-(2-methoxyethyl-(methyl)amino)cyclopentyl]methanone trifluoroacetate salt | 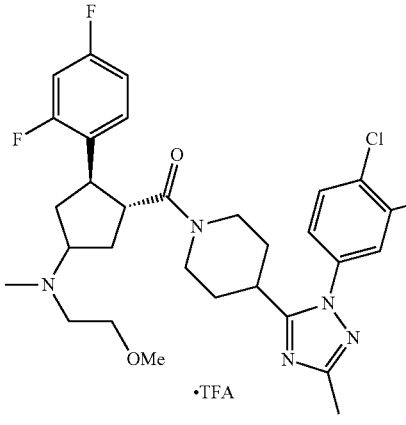 | 585.3 | 586.3/587.8 (M + 1); 1.72 min (LC4) |
| 21 {4-[1-(4-chloro-3-methyl-phenyl)-3-methyl-1H-1,2,4-triazol-5-yl]piperidin-1-yl}[(1R,2R)-2-(2,4-di-fluorophenyl)-4-{methyl-[(1S)-1-phenylethyl]amino}-cyclopentyl]methanone trifluoroacetate salt | 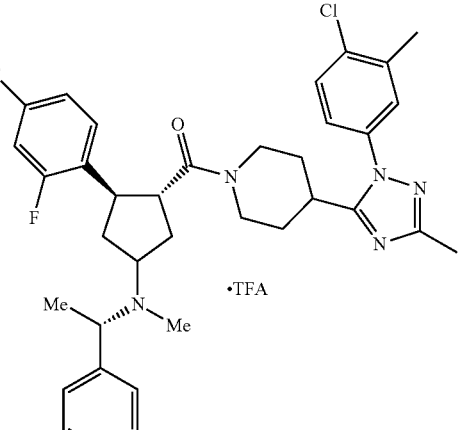 | 631.3 | 632.3/633.7 (M + 1); 1.86 min (LC4) |
| 22 {4-[1-(4-chloro-3-methyl-phenyl)-3-methyl-1H-1,2,4-triazol-5-yl]piperidin-1-yl}[(1R,2R)-2-(2,4-difluoro-phenyl)-4-{methyl[(1R)-1-phenylethyl]amino}cyclopentyl]methanone trifluoroacetate salt | 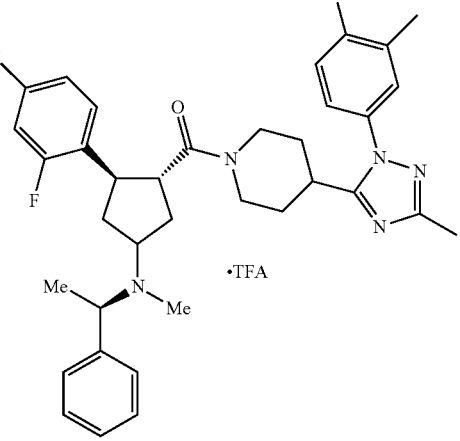 | 631.3 | 632.3/633.6 (M + 1); 1.88 min (LC4) |

TABLE 1-continued

| Example Number | Structure | Calc'd Exact Mass (Parent) | Parent ion m/z (ESI-MS); R$_t$ (LC method) |
|---|---|---|---|
| 23 [(3S,4R)-1-tert-butyl-4-(2,4-difluorophenyl)pyrrolidin-3-yl]{4-[1-(4-chloro-3-methyl-phenyl)-3-methyl-1H-1,2,4-triazol-5-yl]piperidin-1-yl}methanone trifluoroacetate salt | 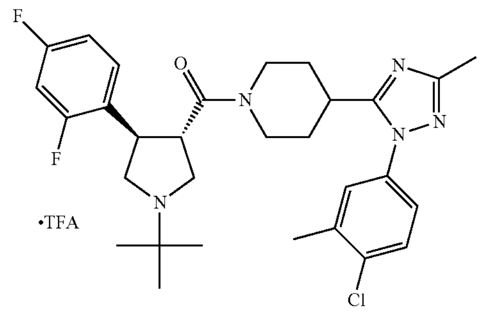 [SMILES: Cc1nc(C2CCN(C(=O)[C@@H]3CN(C(C)(C)C)C[C@H]3c3ccc(F)cc3F)CC2)n(-c2ccc(Cl)c(C)c2)n1] | 555.3 | 556.2, 558.1 (M + 1); 2.81 min. (LC4.) |
| 24 {4-[1-(4-chloro-3-methyl-phenyl)-3-methyl-1H-1,2,4-triazol-5-yl]piperidin-1-yl}[(3S*,4R*)-4-(4-methoxyphenyl)pyrrolidin-3-yl]methanone | 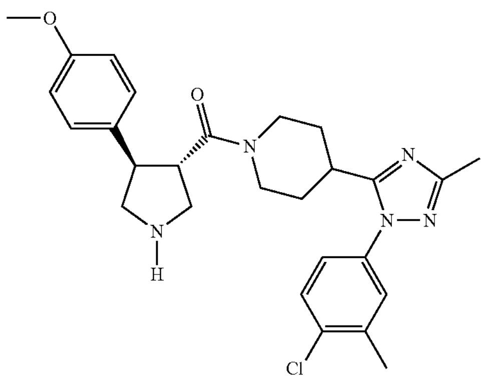 | 493.2 | 494.4/496.3 (M + 1); 2.61 min. (LC4) |
| 25 [(3S,4R)-1-tert-butyl-4-(2,4-difluorophenyl)pyrrolidin-3-yl]{4-[1-(4-chloro-3-methyl-phenyl)-3-(pyridin-3-yl)-1H-1,2,4-triazol-5-yl]piperidin-1-yl}methanone | 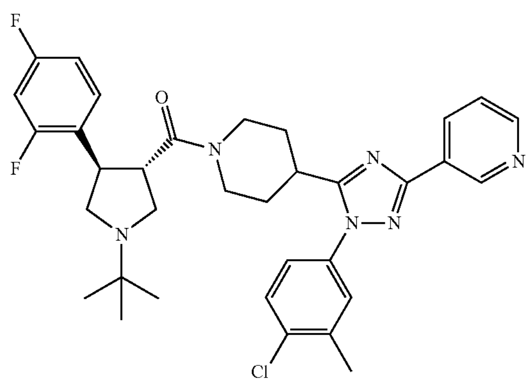 [SMILES: Cc1cc(-n2nc(-c3cccnc3)nc2C2CCN(C(=O)[C@@H]3CN(C(C)(C)C)C[C@H]3c3ccc(F)cc3F)CC2)ccc1Cl] | 618.3 | 619.5/621.4 (M + 1); 2.68 min. (LC4) |
| 26 {4-[1-(4-chloro-3-methyl-phenyl)-3-methyl-1H-1,2,4-triazol-5-yl]piperidin-1-yl}[(3S,4R)-4-(2,4-difluoro-phenyl)pyrrolidin-3-yl]-methanone | 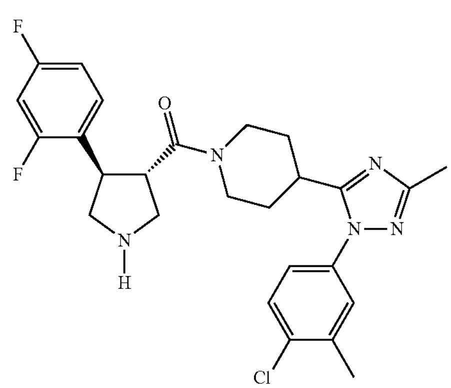 [SMILES: Cc1nc(C2CCN(C(=O)[C@@H]3CNC[C@H]3c3ccc(F)cc3F)CC2)n(-c2ccc(Cl)c(C)c2)n1] | 499.2 | 500.2/502.1 (M + 1); 2.71 min. (LC4) |

TABLE 1-continued

| Example Number | Structure | Calc'd Exact Mass (Parent) | Parent ion m/z (ESI-MS); R$_t$ (LC method) |
|---|---|---|---|
| 27 [(3S,4R)-1-tert-butyl-4-(2,4-difluorophenyl)pyrrolidin-3-yl]{4-[1-(4-chloro-3-methyl-phenyl)-3-(pyridin-2-yl)-1H-1,2,4-triazol-5-yl]piperidin-1-yl}methanone | 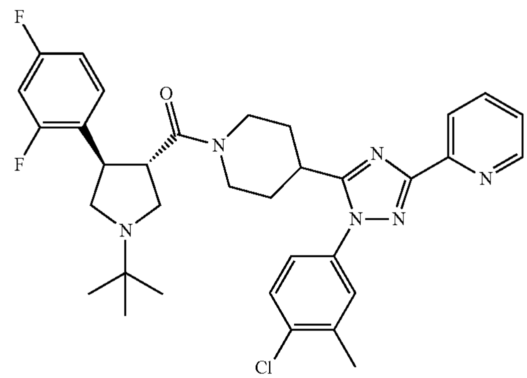 [SMILES: Cc1cc(-n2nc(-c3ccccn3)nc2C2CCN(C(=O)[C@@H]3CN(C(C)(C)C)C[C@H]3c3ccc(F)cc3F)CC2)ccc1Cl] | 618.3 | 619.5/621.5 (M + 1); 2.79 min. (LC4) |
| 28 {4-[1-(4-chloro-3-methylphenyl)-3-methyl-1H-1,2,4-triazol-5-yl]piperidin-1-yl}[(3S,4R)-1-(6-chloro-pyridin-2-yl)-4-(2,4-difluorophenyl)pyrrolidin-3-yl]methanone | | 610.2 | 611.2/613.2 (M + 1); 2.38 min (LC4) |
| 29 [(3S,4R)-1-tert-butyl-4-(2,4-difluorophenyl)pyrrolidin-3-yl]{4-[1-(3,4-difluoro-phenyl)-3-methyl-1H-1,2,4-triazol-5-yl]piperidin-1-yl}-methanone trifluoroacetate salt | 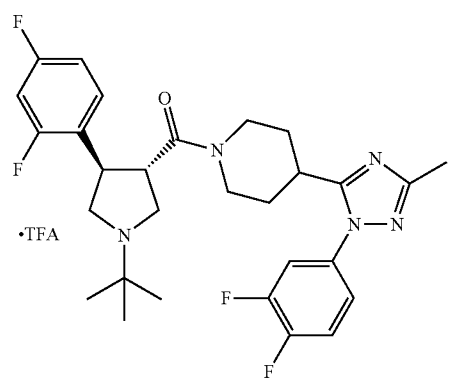 [SMILES: Cc1nc(C2CCN(C(=O)[C@@H]3CN(C(C)(C)C)C[C@H]3c3ccc(F)cc3F)CC2)n(-c2ccc(F)c(F)c2)n1] | 543.3 | 544.4 (M + 1); 2.71 min. (LC4) |
| 30 [(3S,4R)-1-tert-butyl-4-(3-fluoropyridin-4-yl)-pyrrolidin-3-yl]{4-[1-(3-chloro-4-fluorophenyl)-3-methyl-1H-1,2,4-triazol-5-yl]piperidin-1-yl}methanone | 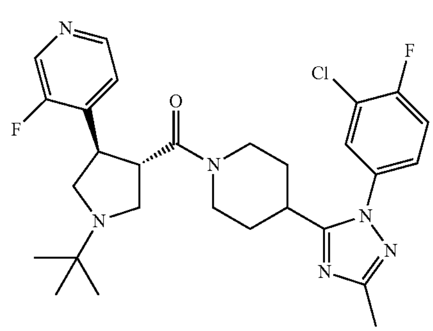 [SMILES: Cc1nc(C2CCN(C(=O)[C@@H]3CN(C(C)(C)C)C[C@H]3c3ccncc3F)CC2)n(-c2ccc(F)c(Cl)c2)n1] | 542.2 | 543.3/545.4 (M + 1); 2.48 min (LC4) |

TABLE 1-continued

| Example Number | Structure | Calc'd Exact Mass (Parent) | Parent ion m/z (ESI-MS); R$_t$ (LC method) |
|---|---|---|---|
| 31 [(3S,4R)-1-tert-butyl-4-(2,4-difluorophenyl)pyrrolidin-3-yl]{4-[1-(2,4-dichlorophenyl)-3-methyl-1H-pyrazol-5-yl]piperidin-1-yl}methanone | | 575.2 | 575.4/577.5 (M + 1); 2.87 min. (LC4) |
| 32 [(3S,4R)-1-tert-butyl-4-(2,4-difluorophenyl)pyrrolidin-3-yl]{4-[1-(2-chlorophenyl)-3-methyl-1H-pyrazol-5-yl]-piperidin-1-yl}methanone | 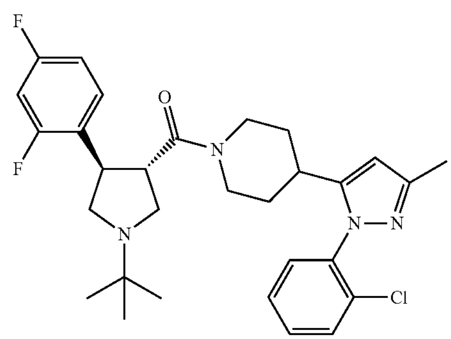 [SMILES: Cc1cc(C2CCN(C(=O)[C@@H]3CN(C(C)(C)C)C[C@H]3c3ccc(F)cc3F)CC2)n(-c2ccccc2Cl)n1] | 540.2 | 541.4/542.4 (M + 1); 2.66. (LC4) |
| 33 [(3S,3R)-1-tert-butyl-4-(2,4-difluorophenyl)pyrrolidin-3-yl]{4-[1-(3,4-dichlorophenyl)-3-methyl-1H-pyrazol-5-yl]piperidin-1-yl}methanone | | 574.2 | 575.4/577.4 (M + 1); 3.00. (LC4) |
| 34 [(3S,4R)-1-tert-butyl-4-(2,4-difluorophenyl)pyrrolidin-3-yl]{4-[1-(3-chlorophenyl)-3-methyl-1H-pyrazol-5-yl]-piperidin-1-yl}methanone | 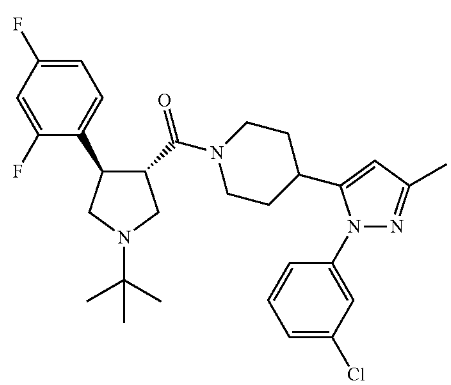 [SMILES: Cc1cc(C2CCN(C(=O)[C@@H]3CN(C(C)(C)C)C[C@H]3c3ccc(F)cc3F)CC2)n(-c2cccc(Cl)c2)n1] | 540.2 | 541.4/543.3 (M + 1); 2.82. (LC4) |

TABLE 1-continued

| Example Number | Structure | Calc'd Exact Mass (Parent) | Parent ion m/z (ESI-MS); R$_t$ (LC method) |
|---|---|---|---|
| 35 [(3S,4R)-1-tert-butyl-4-(2,4-difluorophenyl)pyrrolidin-3-yl](4-{3-methyl-1-[4-(trifluoromethoxy)phenyl]-1H-pyrazol-5-yl}piperidin-1-yl)methanone | 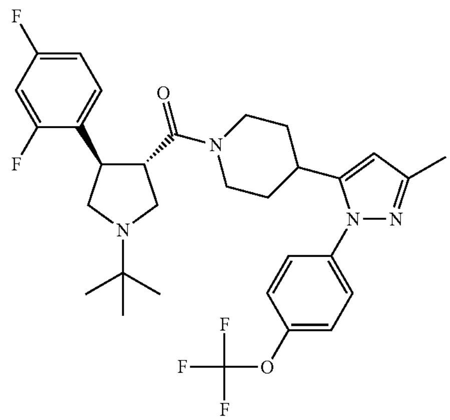 [SMILES: Cc1cc(C2CCN(C(=O)[C@@H]3CN(C(C)(C)C)C[C@H]3c3ccc(F)cc3F)CC2)n(-c2ccc(OC(F)(F)F)cc2)n1] | 590.3 | 591.5 (M + 1); 2.96 min. (LC4) |
| 36 4-[5-(1-{[(3S,4R)-1-tert-butyl-4-(2,4-difluorophenyl)pyrrolidin-3-yl]carbonyl}piperidin-4-yl)-3-methyl-1H-pyrazol-1-yl]benzonitrile | | 531.3 | 532.5 (M + 1); 2.63 min. (LC4) |
| 37 [(3S,4R)-1-tert-butyl-4-(2,4-difluorophenyl)pyrrolidin-3-yl]{4-[1-(4-fluorophenyl)-3-methyl-1H-pyrazol-5-yl]-piperidin-1-yl}methanone | 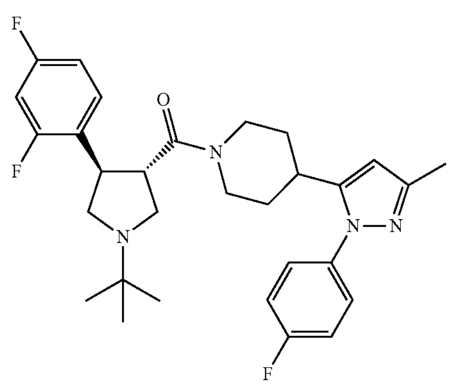 [SMILES: Cc1cc(C2CCN(C(=O)[C@@H]3CN(C(C)(C)C)C[C@H]3c3ccc(F)cc3F)CC2)n(-c2ccc(F)cc2)n1] | 524.3 | 525.5 (M + 1); 2.66 min. (LC4) |

TABLE 1-continued

| Example Number | Structure | Calc'd Exact Mass (Parent) | Parent ion m/z (ESI-MS); R$_t$ (LC method) |
|---|---|---|---|
| 38 [(3S,4R)-1-tert-butyl-4-(2,4-difluorophenyl)pyrrolidin-3-yl](4-{3-methyl-1-[3-(trifluoromethyl)phenyl]-1H-pyrazol-5-yl}piperidin-1-yl)methanone | 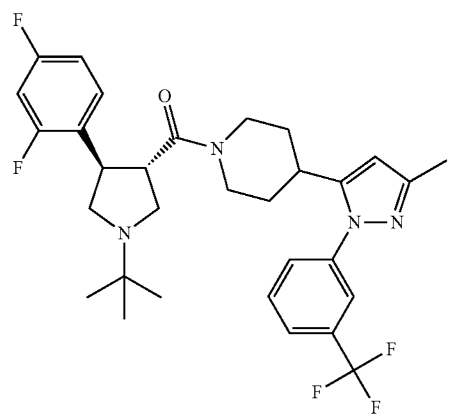 [SMILES: Cc1cc(C2CCN(C(=O)[C@@H]3CN(C(C)(C)C)C[C@H]3c3ccc(F)cc3F)CC2)n(-c2cccc(C(F)(F)F)c2)n1] | 574.3 | 575.5 (M + 1); 2.94 min. (LC4) |
| 39 [(3S,4R)-1-tert-butyl-4-(2,4-difluorophenyl)pyrrolidin-3-yl]{4-[1-(4-chloro-2-methylphenyl)-3-methyl-1H-pyrazol-5-yl]piperidin-1-yl}methanone | 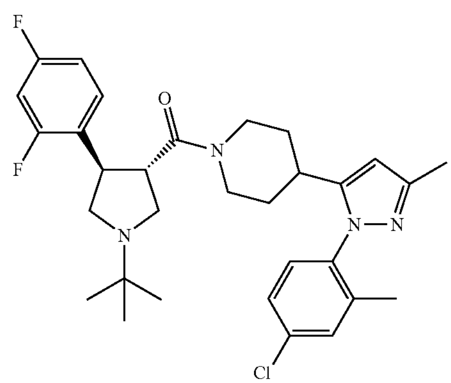 [SMILES: Cc1cc(C2CCN(C(=O)[C@@H]3CN(C(C)(C)C)C[C@H]3c3ccc(F)cc3F)CC2)n(-c2ccc(Cl)cc2C)n1] | 554.3 | 555.5/557.5 (M + 1); 2.87 min. (LC4) |
| 40 [(3S,4R)-1-tert-butyl-4-(2,4-difluorophenyl)pyrrolidin-3-yl](4-{3-methyl-1-[2-(trifluoromethyl)phenyl]-1H-pyrazol-5-yl}piperidin-1-yl)methanone | 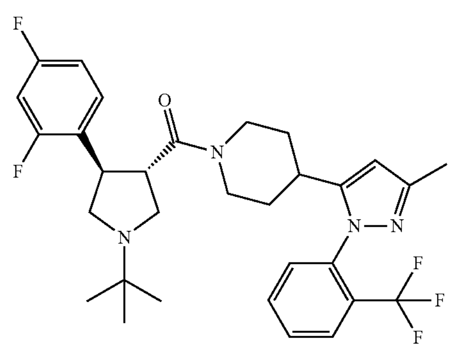 [SMILES: Cc1cc(C2CCN(C(=O)[C@@H]3CN(C(C)(C)C)C[C@H]3c3ccc(F)cc3F)CC2)n(-c2ccccc2C(F)(F)F)n1] | 574.3 | 575.5 (M + 1); 2.75 min. (LC4) |
| 41 [(3S,4R)-1-tert-butyl-4-(2,4-difluorophenyl)pyrrolidin-3-yl]{4-[1-(2,4-difluorophenyl)-3-methyl-1H-pyrazol-5-yl]piperidin-1-yl}methanone | | 542.3 | 543.5 (M + 1); 2.66 min. (LC4) |

TABLE 1-continued

| Example Number | Structure | Calc'd Exact Mass (Parent) | Parent ion m/z (ESI-MS); R$_t$ (LC method) |
|---|---|---|---|
| 42 [(3S,4R)-1-tert-butyl-4-(2,4-difluorophenyl)pyrrolidin-3-yl]{4-[1-(3-chloro-4-methylphenyl)-3-methyl-1H-pyrazol-5-yl]piperidin-1-yl}methanone | 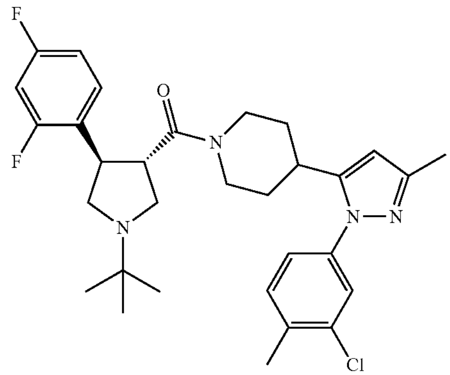 [SMILES: Cc1cc(C2CCN(C(=O)[C@@H]3CN(C(C)(C)C)C[C@H]3c3ccc(F)cc3F)CC2)n(-c2ccc(C)c(Cl)c2)n1] | 554.3 | 555.4/557.4 (M + 1); 2.93 min. (LC4) |
| 43 4-[5-(1-{[(3S,4R)-1-tert-butyl-4-(2,4-difluorophenyl)-pyrrolidin-3-yl]carbonyl}-piperidin-4-yl)-3-methyl-1H-pyrazol-1-yl]-3-chloro-benzonitrile | 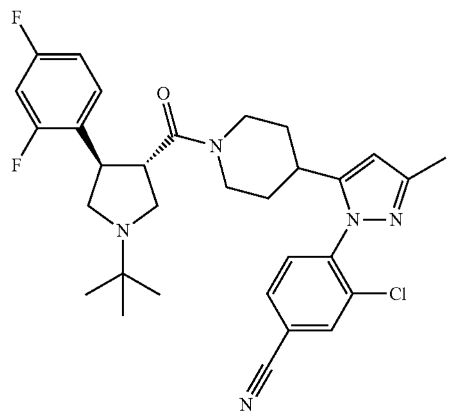 [SMILES: Cc1cc(C2CCN(C(=O)[C@@H]3CN(C(C)(C)C)C[C@H]3c3ccc(F)cc3F)CC2)n(-c2ccc(C#N)cc2Cl)n1] | 565.2 | 566.5/568.5 (M + 1); 2.75 min. (LC4) |
| 44 [(3S,4R)-1-tert-butyl-4-(2,4-difluorophenyl)pyrrolidin-3-yl]{4-[1-(3,5-difluorophenyl)-3-methyl-1H pyrazol-5-yl]piperidin-1-yl}methanone | | 542.3 | 543.5 (M + 1); 2.78 min. (LC4) |
| 45 [(3S,4R)-1-tert-butyl-4-(2,4-difluorophenyl)pyrrolidin-3-yl]{4-[1-(2,3-dichlorophenyl)-3-methyl-1H-pyrazol-5-yl]piperidin-1-yl}methanone | | 574.2 | 575.4/577.3 (M + 1); 2.84 min. (LC4) |

TABLE 1-continued

| Example Number | Structure | Calc'd Exact Mass (Parent) | Parent ion m/z (ESI-MS); R$_t$ (LC method) |
|---|---|---|---|
| 46 [(3S,4R)-1-tert-butyl-4-(2,4-difluorophenyl)pyrrolidin-3-yl]{4-[1-(4-methoxyphenyl)-3-methyl-1H-pyrazol-5-yl]piperidin-1-yl}methanone | 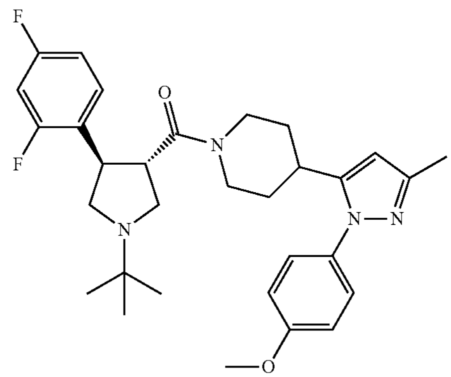 [SMILES: COc1ccc(-n2nc(C)cc2C2CCN(C(=O)[C@@H]3CN(C(C)(C)C)C[C@H]3c3ccc(F)cc3F)CC2)cc1] | 536.3 | 537.5 (M + 1); 2.60 min. (LC4) |
| 47 [(3S,4R)-1-tert-butyl-4-(2,4-difluorophenyl)pyrrolidin-3-yl](4-{3-methyl-1-[4-(trifluoromethyl)phenyl]-1H-pyrazol-5-yl}piperidin-1-yl)methanone | 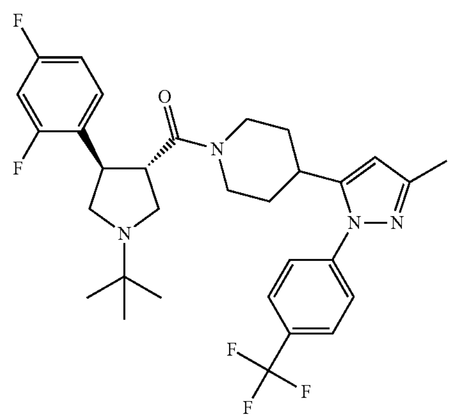 [SMILES: Cc1cc(C2CCN(C(=O)[C@@H]3CN(C(C)(C)C)C[C@H]3c3ccc(F)cc3F)CC2)n(-c2ccc(C(F)(F)F)cc2)n1] | 574.3 | 575.5 (M + 1); 2.95 min. (LC4) |
| 48 [(3S,4R)-1-tert-butyl-4-(2,4-difluorophenyl)pyrrolidin-3-yl]{4-[1-(4-chloro-2-fluorophenyl)-3-methyl-1H-pyrazol-5-yl]piperidin-1-yl}methanone | 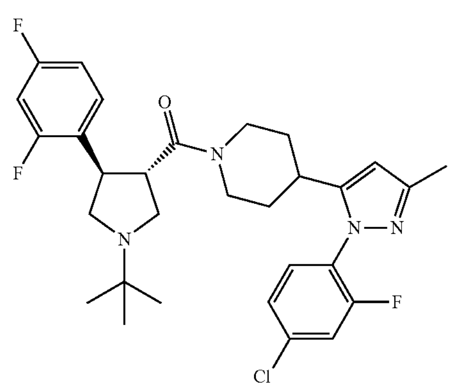 | 558.2 | 559.5/561.4 (M + 1); 2.81 min. (LC4) |

TABLE 1-continued

| Example Number | Structure | Calc'd Exact Mass (Parent) | Parent ion m/z (ESI-MS); R$_t$ (LC method) |
| --- | --- | --- | --- |
| 49 [(3S,4R)-1-tert-butyl-4-(2,4-difluorophenyl)pyrrolidin-3-yl]{4-[1-(4-chloro-3-methylphenyl)-3-methyl-1H-pyrazol-5-yl]piperidin-1-yl}methanone trifluoroacetate salt | 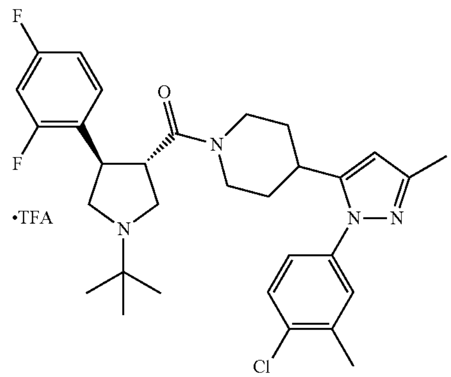 [SMILES: Cc1cc(C2CCN(C(=O)[C@@H]3CN(C(C)(C)C)C[C@H]3c3ccc(F)cc3F)CC2)n(-c2ccc(Cl)c(C)c2)n1] | 554.3 | 555.4/557.4 (M + 1); 2.92 min. (LC4) |
| 50 [(3S,4R)-1-tert-butyl-4-(2,4-difluorophenyl)pyrrolidin-3-yl]{4-[1-(3,4-difluorophenyl)-3-methyl-1H-pyrazol-5-yl]piperidin-1-yl}methanone trifluoroacetate salt | 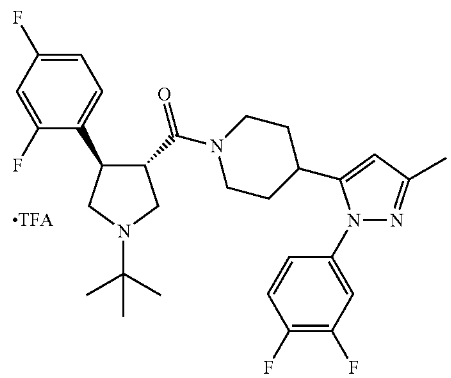 [SMILES: Cc1cc(C2CCN(C(=O)[C@@H]3CN(C(C)(C)C)C[C@H]3c3ccc(F)cc3F)CC2)n(-c2ccc(F)c(F)c2)n1] | 542.3 | 543.4 (M + 1); 2.85 min. (LC4) |
| 51 [(3S,4R-1-tert-butyl-4-(2,4-difluorophenyl)pyrrolidin-3-yl]{4-[1-(2-chloro-5-fluoro-phenyl)-3-methyl-1H-pyrazol-5-yl]piperidin-1-yl}methanone trifluoro-acetate salt | 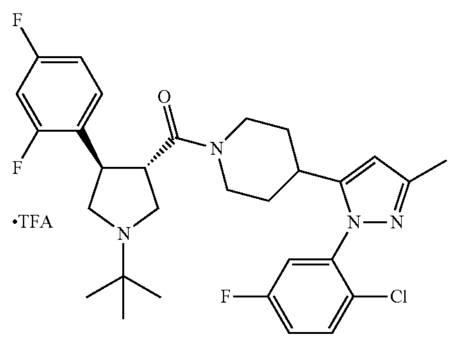 [SMILES: Cc1cc(C2CCN(C(=O)[C@@H]3CN(C(C)(C)C)C[C@H]3c3ccc(F)cc3F)CC2)n(-c2cc(F)ccc2Cl)n1] | 558.2 | 559.2/561.0 (M + 1); 1.10 min (LC2) |
| 52 [(3S,4R)-1-tert-butyl-4-(2,4-difluorophenyl)pyrrolidin-3-yl]{4-[1-(4-chlorophenyl)-3-methyl-1H-pyrazol-5-yl]-piperidin-1-yl}methanone trifluoroacetate salt | 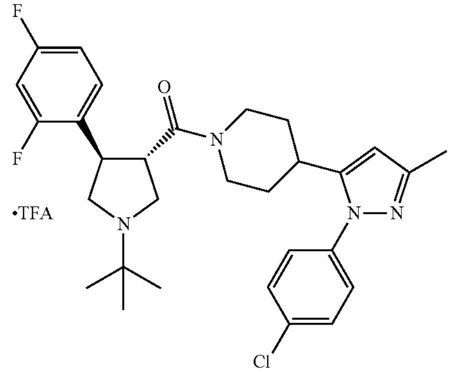 [SMILES: Cc1cc(C2CCN(C(=O)[C@@H]3CN(C(C)(C)C)C[C@H]3c3ccc(F)cc3F)CC2)n(-c2ccc(Cl)cc2)n1] | 540.2 | 541.4/543.4 (M + 1); 2.90 min. (LC4) |

TABLE 1-continued

| Example Number | Structure | Calc'd Exact Mass (Parent) | Parent ion m/z (ESI-MS); R$_t$ (LC method) |
|---|---|---|---|
| 53 [(3S,4R)-1-tert-butyl-4-(2,4-difluorophenyl)pyrrolidin-3-yl]{4-[3-methyl-1-(2,3,5-trifluorophenyl)-1H-pyrazol-5-yl]piperidin-1-yl}-methanone trifluoroacetate salt | | 560.3 | 561.4 (M + 1); 2.87 min. (LC4) |
| 54 [(3S,4R)-1-tert-butyl-4-(2,4-difluorophenyl)pyrrolidin-3-yl]{4-[1-(3-chloro-2-fluorophenyl)-3-methyl-1H-pyrazol-5-yl]piperidin-1-yl}methanone trifluoroacetate salt | | 558.2 | 559.4/561.4 (M + 1); 2.87 min. (LC4) |
| 55 [(3S,4R)-1-tert-butyl-4-(2,4-difluorophenyl)pyrrolidin-3-yl]{4-[1-(2,5-dichlorophenyl)-3-methyl-1H-pyrazol-5-yl]piperidin-1-yl}methanone trifluoroacetate salt | | 574.2 | 575.4/577.3 (M + 1); 2.85 min. (LC4) |
| 56 [(3S,4R)-1-tert-butyl-4-(2,4-difluorophenyl)pyrrolidin-3-yl]{4-[1-(5-chloro-2-fluoro-phenyl)-3-methyl-1H-pyrazol-5-yl]piperidin-1-yl}methanone trifluoroacetate salt | | 558.2 | 559.2/561.3 (M + 1); 1.67 min (LC4) |

TABLE 1-continued

| Example Number | Structure | Calc'd Exact Mass (Parent) | Parent ion m/z (ESI-MS); R_t (LC method) |
|---|---|---|---|
| 57 [(3S,4S)-1-tert-butyl-4-(5-fluoropyridin-2-yl)-pyrrolidin-3-yl]{4-[1-(3-chloro-4-fluorophenyl)-3-methyl-1H-pyrazol-5-yl]-piperidin-1-yl}methanone formic acid salt | 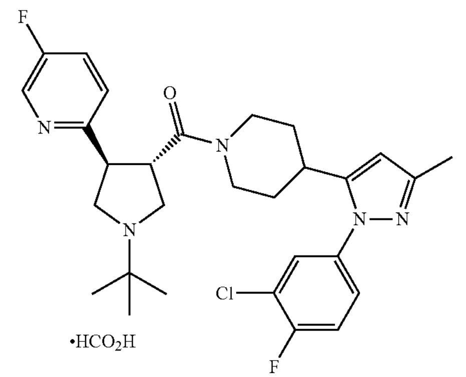 [SMILES: Cc1cc(C2CCN(C(=O)[C@@H]3CN(C(C)(C)C)C[C@H]3c3ccc(F)cn3)CC2)n(-c2ccc(F)c(Cl)c2)n1 ; "·HCO2H"] | 542.1 | 542.4/544.4 (M + 1); 2.77 min. (LC4) |
| 58: {4-[1-(2,5-dichlorophenyl)-3-methyl-1H-pyrazol-5-yl]piperidin-1-yl}[(3S,4R)-4-(2,4-difluorophenyl)-pyrrolidin-3-yl]methanone trifluoroacetate salt | 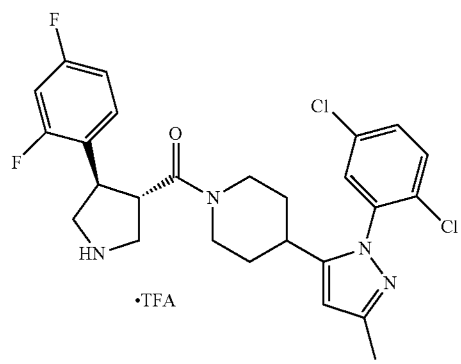 [SMILES: Cc1cc(C2CCN(C(=O)[C@@H]3CNC[C@H]3c3ccc(F)cc3F)CC2)n(-c2cc(Cl)ccc2Cl)n1] | 518.2 | 519.1 (M + 1); 1.60 (LC4) |
| 59 {4-[1-(3,4-dichlorophenyl)-3-methyl-1H-pyrazol-5-yl]piperidin-1-yl}[(3S,4R)-4-(2,4-difluorophenyl)-pyrrolidin-3-yl]methanone trifluoroacetate salt | 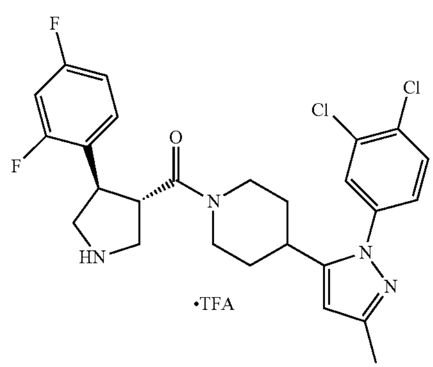 [SMILES: Cc1cc(C2CCN(C(=O)[C@@H]3CNC[C@H]3c3ccc(F)cc3F)CC2)n(-c2ccc(Cl)c(Cl)c2)n1] | 518.2 | 519.1 (M + 1); 1.73 min (LC4) |
| 60 {4-[1-(3-chloro-4-fluorophenyl)-3-methyl-1H-pyrazol-5-yl]piperidin-1-yl}[(3S,4R)-4-(2-methylphenyl)pyrrolidin-3-yl]methanone trifluoroacetate salt | | 480.2 | 481.2 (M + 1); 1.10 min (LC2) |

TABLE 1-continued

| Example Number | Structure | Calc'd Exact Mass (Parent) | Parent ion m/z (ESI-MS); R$_t$ (LC method) |
|---|---|---|---|
| 61 {4-[1-(2,5-dichlorophenyl)-3-methyl-1H-pyrazol-5-yl]piperidin-1-yl}[(1R,2R,4S)-2-(2,4-di-fluorophenyl)-4-(di-methylamino)-4-methyl-cyclopentyl]methanone | 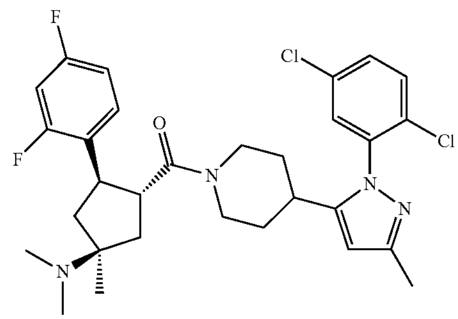 [SMILES: Cc1cc(C2CCN(C(=O)[C@@H]3C[C@@](C)(N(C)C)C[C@H]3c3ccc(F)cc3F)CC2)n(-c2cc(Cl)ccc2Cl)n1] | 574.2 | 575.4/577.2 (M + 1), 2.88 min. (LC4) |
| 62 {4-[1-(2,4-dichlorophenyl)-3-methyl-1H-pyrazol-5-yl]piperidin-1-yl}-[(1R,2R,4S)-2-(2,4-difluoro-phenyl)-4-(dimethyl-amino)-4-methylcyclopentyl]-methanone | 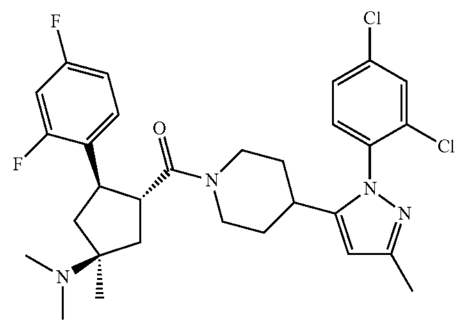 [SMILES: Cc1cc(C2CCN(C(=O)[C@@H]3C[C@@](C)(N(C)C)C[C@H]3c3ccc(F)cc3F)CC2)n(-c2ccc(Cl)cc2Cl)n1] | 574.2 | 575.4/577.3 (M + 1); 2.89 min. (LC4) |
| 63 {4-[1-(4-chloro-2-fluoro-phenyl)-3-methyl-1H-pyrazol-5-yl]piperidin-1-yl}[(1R,2R,4S)-2-(2,4-difluoro-phenyl)-4-(di-methylamino)-4-methyl-cyclopenlyl]-methanone | 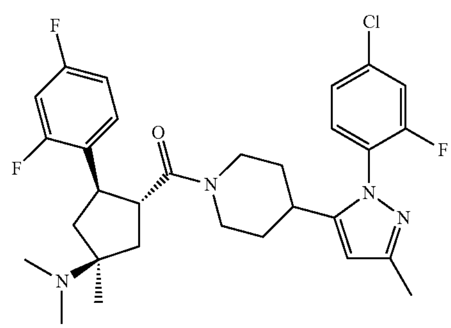 [SMILES: Cc1cc(C2CCN(C(=O)[C@@H]3C[C@@](C)(N(C)C)C[C@H]3c3ccc(F)cc3F)CC2)n(-c2ccc(Cl)cc2F)n1] | 558.2 | 559.4/561.4 (M + 1); 2.85 min. (LC4) |
| 64 {4-[1-(3-chloro-4-fluorophenyl)-3-methyl-1H-pyrazol-5-yl]piperidin-1-yl}[(1R,2R,4S)-2-(2,4-difluorophenyl)-4-(dimethyl-amino)-4-methylcyclo-pentyl]methanone formic acid salt | 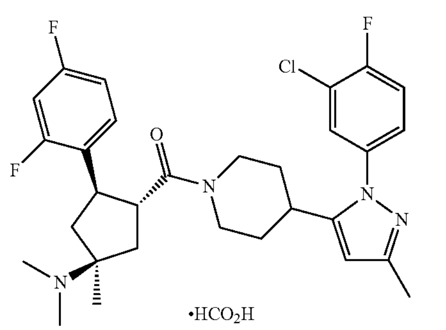 [SMILES: Cc1cc(C2CCN(C(=O)[C@@H]3C[C@@](C)(N(C)C)C[C@H]3c3ccc(F)cc3F)CC2)n(-c2ccc(F)c(Cl)c2)n1 ; "·HCO2H"] | 558.2 | 559.4/561.4 (M + 1); 2.89 min. (LC4) |

TABLE 1-continued

| Example Number | Structure | Calc'd Exact Mass (Parent) | Parent ion m/z (ESI-MS); R$_t$ (LC method) |
|---|---|---|---|
| 65 [(1R,2R,4S)-4-amino-2-(2,4-difluorophenyl)-4-methyl-cyclopentyl]{4-[1-(3,4-dichlorophenyl)-3-methyl-1H-pyrazol-5-yl]piperidin-1-yl}methanone trifluoroacetate salt | | 546.2 | 530.2/532.1 (M − 17 + 1); 2.91 min. (LC4) |
| 66 [(1R,2R,4S)-4-amino-2-(2,4-difluorophenyl)-4-methyl-cyclopentyl]{4-[1-(2,5-dichlorophenyl)-3-methyl-1H-pyrazol-5-yl]piperidin-1-yl}methanone trifluoroacetate salt | | 546.2 | 530.2/532.1 (M − 17 + 1); 2.77 min. (LC4) |
| 67 [(1R,2R,4R)-4-amino-2-(2,4-difluorophenyl)-4-methyl-cyclopentyl]{4-[1-(3-chloro-4-fluorophenyl)-3-methyl-1H-pyrazol-5-yl]piperidin-1-yl}methanone trifluoroacetate salt | | 530.2 | 531.2/533.2 (M + 1); 1.71 (LC4) |
| 68 [(1R,2R,4S)-amino-2-(2,4-difluorophenyl)-4-methyl-cyclopentyl]{4-[1-(3-chloro-4-fluorophenyl)-1H-pyrazol-5-yl]piperidin-1-yl}-methanone trifluoroacetate salt | | 516.2 | 517.0/519.0 (M + 1); 1.63 min (LC4) |

TABLE 1-continued

| Example Number | Structure | Calc'd Exact Mass (Parent) | Parent ion m/z (ESI-MS); R$_t$ (LC method) |
|---|---|---|---|
| 69 {4-[1-(3-chloro-4-fluoro-phenyl)-1H-pyrazol-5-yl]-piperidin-1-yl}[(1R,2R,4S)-2-(2,4-difluorophenyl)-4-(dimethylamino)-4-methyl-cyclopentyl]methanone trifluoroacetate salt | 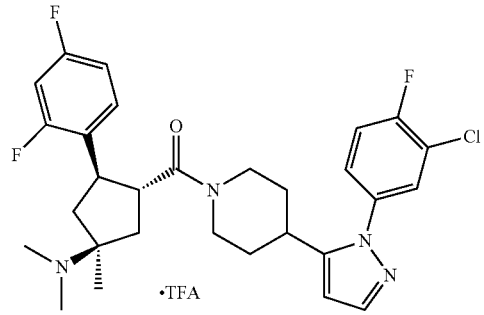 [SMILES: CN(C)[C@]1(C)C[C@@H](C(=O)N2CCC(c3ccnn3-c3ccc(F)c(Cl)c3)CC2)[C@H](c2ccc(F)cc2F)C1] | 544.2 | 545.2/547.0 (M + 1); 1.64 min (LC4) |
| 70 [(1R,2R,4S)-4-amino-2-(2,4-difluorophenyl)-4-methyl-cyclopentyl]{4-[1-(3-chloro-4-fluorophenyl)-1H-pyrazol-5-yl]piperidin-1-yl}-methanone trifluoroacetate salt | 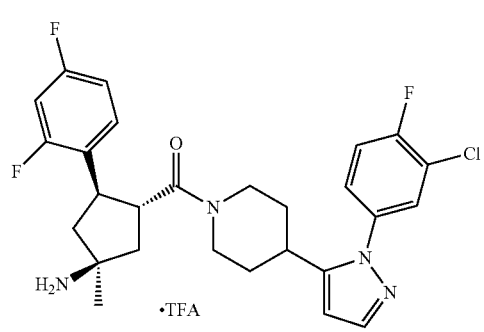 [SMILES: C[C@@]1(N)C[C@@H](C(=O)N2CCC(c3ccnn3-c3ccc(F)c(Cl)c3)CC2)[C@H](c2ccc(F)cc2F)C1] | 516.2 | 517.2/519.2 (M + 1); 1.64 min (LC4) |
| 71 {4-[1-(3-chloro-4-fluoro-phenyl)-1H-pyrazol-5-yl]piperidin-1-yl}-{(1R,2R,4S)-2-(2,4-difluoro-phenyl)-4-methyl-4-[(3,3,3-trifluoropropyl)amino]-cyclopentyl}methanone trifluoroacetate salt | 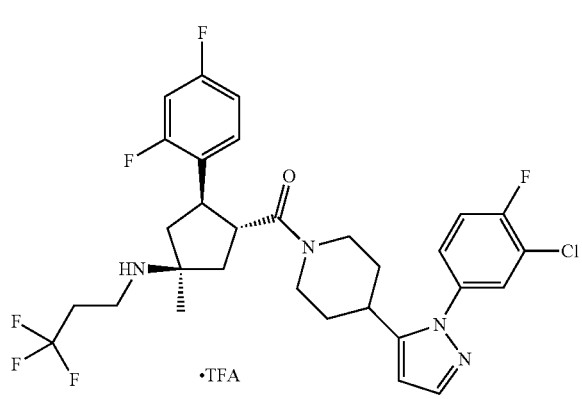 [SMILES: C[C@@]1(NCCC(F)(F)F)C[C@@H](C(=O)N2CCC(c3ccnn3-c3ccc(F)c(Cl)c3)CC2)[C@H](c2ccc(F)cc2F)C1] | 612.2 | 613.2/614.9 (M + 1); 1.78 min (LC4) |
| 72 {4-[1-(3-chloro-4-fluoro-phenyl)-1H-pyrazol-5-yl]piperidin-1-yl}-[(1R,2R,4R)-2-(2,4-difluoro-phenyl)-4-(dimethylamino)-4-methylcyclopentyl]-methanone trifluoroacetate salt | 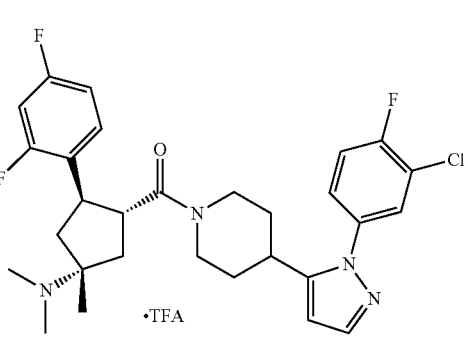 | 544.2 | 545.1/546.5 (M + 1); 1.63 (LC4) |

TABLE 1-continued

| Example Number | Structure | Calc'd Exact Mass (Parent) | Parent ion m/z (ESI-MS); R$_t$ (LC method) |
|---|---|---|---|
| 73 [(1S,2S,4S)-4-amino-2-(2,4-difluorophenyl)-4-methyl-cyclopentyl]{4-[1-(3-chloro-4-fluorophenyl)-3-methyl-1H-pyrazol-5-yl]piperidin-1-yl}-methanone trifluoroacetate salt | | 530.2 | 514.2/516.3 (M + 1); 2.79 min. (LC4) |
| 74 [(1S,2S,4S)-4-amino-2-(2,4-difluorophenyl)-4-methyl-cyclopentyl]{4-[1-(3-chloro-4-fluorophenyl)-3-methyl-1H-pyrazol-5-yl]piperidin-1-yl}-methanone trifluoroacetate salt | | 530.2 | 531.3/533.2 (M + 1); 2.90 min. (LC4) |
| 75 [(3S,4R)-1-tert-butyl-4-(2,4-difluorophenyl)-pyrrolidin-3-yl]{4-[1-(4-chloro-3-methyl-phenyl)-1H-tetrazol-5-yl]piperidin-1-yl}methanone trifluoroacetate salt | | 542.2 | 543.3/545.3 (M + 1); 1.65 min (LC4) |
| 76 [(3S,4R)-1-tert-butyl-4-(2,4-difluorophenyl)pyrrolidin-3-yl]{4-[1-(4-chlorophenyl)-1H-tetrazol-5-yl]piperidin-1-yl}methanone trifluoroacetate salt | | 528.2 | 529.3/531.3 (M + 1); 1.58 (LC4) |

TABLE 1-continued

| Example Number | Structure | Calc'd Exact Mass (Parent) | Parent ion m/z (ESI-MS); $R_t$ (LC method) |
|---|---|---|---|
| 77 [(3S,4R)-1-tert-butyl-4-(2,4-difluorophenyl)pyrrolidin-3-yl]{4-[1-(3-chloro-4-fluorophenyl)-1H-pyrazol-5-yl]piperidin-1-yl}methanone trifluoroacetate salt | 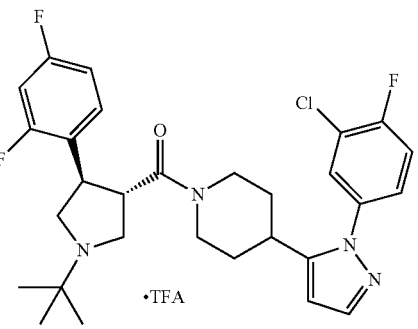 | 544.2 | 545.3/547.1 (M + 1); 1.67 (LC4) |

The utility of the compounds in accordance with the present invention as inhibitors of prolylcarboxypeptidase (PRCP) enzyme activity may be demonstrated by the following assays:

BIOLOGICAL EXAMPLE 1

Prolylcarboxypeptidase (PRCP) Enzyme Activity Assay

The potency of compounds of formula I against PrCP was determined by a fluorescence intensity kinetic assay measuring the $IC_{50}$ values of PrCP inhibitor test compounds. Recombinant human and mouse PrCP enzymes from CHO or HEK expression systems (with comparable results for HEK enzymes) were prepared in-house and used in the assay. The assay was run on a Perkin Elmer Envision 2103 plate reader using a 320 nm excitation filter and a 405 emission filter. The assay was performed using a Hamilton Star liquid handling workstation. The assay employed the internally quenched fluorescent substrate (1S)-1-carboxy-5-[(2,4-dinitrophenyl)amino]pentyl N-[(7-methoxy-2-oxo-2H-chromen-4-yl)acetyl]-L-alanyl-L-prolinate prepared in house.

The assay was run in a 384-well microtiter plate at 37° C. with a total volume of 50 uL. Final assay concentrations were 0.13 nM human PrCP(CHO) or 0.09 nM mouse PrCP(CHO) enzyme, 15 uM substrate and varying concentrations of inhibitor in buffer containing 10 mM NaOAc, 100 mM NaCl and 19.5 ug/mL BSA at pH 5.5. The assay also contained 2% DMSO used to solubilize the substrate and inhibitor. Inhibitors were prepared in 100% DMSO and serial diluted (in 100% DMSO) to generate 11 point titration curves. Either 39 uL of human or mouse PrCP enzyme was added to the wells of the assay plate, followed by a 1 uL addition of the serially diluted inhibitor and mixed three times using a 30 uL mix volume. The reaction was initiated by the addition of 10 uL substrate and mixed three times using a 30 uL mix volume. The reactions were monitored continuously over 25 min at 37° C. to obtain initial velocities. IC50 values were calculated by comparing the resulting rates of reaction of the inhibited and control initial velocities. For the more potent compounds, a modified dilution series at a lower concentration range was used to more accurately determine the potency.

The enzymes were diluted in a mixture of 10 mM NaOAc (pH 5.5)/100 mM NaCl buffer containing 25 ug/mL bovine serum albumin that had been warmed to 37° C. in a water bath. The PrCP inhibitor test compounds were plated in 100% DMSO with a highest concentration of 500 uM. There were 12 dilution points for each compound tested including a blank with DMSO only. The test compounds from the source titration plate were transferred into the assay reaction plate at a 1:50 dilution using the Hamilton Star workstation and mixed, resulting in a final concentration for the test compounds in the range of 10,000 to 0.066 nM. Likewise, two control compounds were similarly titrated and included in each assay, with final starting concentrations starting at 10,000 nM and 200 nM, respectively. The reaction was initiated by the addition of 75 uM of the (1S)-1-carboxy-5-[(2,4-dinitrophenyl)amino]pentyl N-[(7-methoxy-2-oxo-2H-chromen-4-yl)acetyl]-L-alanyl-L-prolinate substrate, which was diluted in a mixture of 10 mM NaOAc (pH 5.5)/100 mM NaCl that had been warmed to 37° C. in a water bath, dispensed using the Hamilton Star workstation and mixed. The substrate was solubilized in 100% DMSO prior to dilution into the assay. The final assay concentrations in the 50 uL reactions were 15 uM of (1S)-1-carboxy-5-[(2,4-dinitrophenyl)amino]pentyl N-[(7-methoxy-2-oxo-2H-chromen-4-yl)acetyl]-L-alanyl-L-prolinate substrate, 0.13 nM Human PrCP(CHO) or 0.09 nM Mouse PrCP (CHO), and 2% DMSO.

The compounds of the present invention, including the compounds of Examples 1 to 77, exhibit a PrCP inhibition constant $IC_{50}$ of less than 10 µM. Preferred compounds of the present invention were found to exhibit a PRCP inhibition constant $IC_{50}$ of less than 1 µM. More preferred compounds of the present invention were found to exhibit a PrCP inhibition constant $IC_{50}$ of less than 100 nM.

| Human PRCP Enzyme Inhibition for Selected Compounds |||
|---|---|---|
| Example Number | $IC_{50}$ (nM) | Cell line |
| 1 | 13.9 | CHO |
| 2 | 5.9 | CHO |
| 3 | 9.8 | CHO |
| 4 | 0.5 | CHO |
| 5 | 10.7 | CHO |
| 6 | 8.1 | CHO |
| 7 | 6.3 | CHO |
| 8 | 0.8 | CHO |
| 23 | 0.9 | CHO |
| 74 | 18 | CHO |

Examples of Pharmaceutical Compositions

As a specific embodiment of an oral composition of a composition of the present invention, 5 mg of Example 1 is formulated with sufficient finely divided lactose to provide a total amount of 580 to 590 mg to fill a size O hard gelatin capsule.

As another specific embodiment of an oral composition of a compound of the present invention, 2.5 mg of Example 1 is formulated with sufficient finely divided lactose to provide a total amount of 580 to 590 mg to fill a size O hard gelatin capsule.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the subject or mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the practices of the present invention. It is intended, therefore, that the invention be limited only by the scope of the claims which follow and that such claims be interpreted as broadly as is reasonable.

What is claimed is:

1. A compound of structural formula I-1 and I-b:

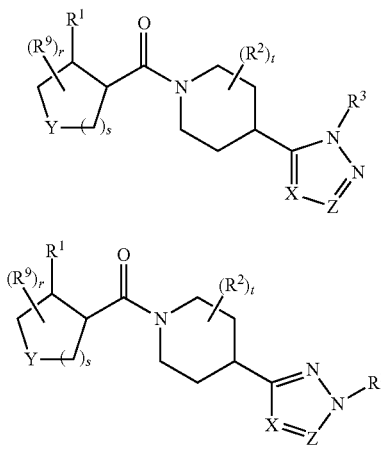

or a pharmaceutically acceptable salt thereof; wherein
X is independently selected from the group consisting of: N and $CR^8$;
Y is independently selected from the group consisting of: $NR^5$ or $CR^6R^7$;
Z is independently selected from the group consisting of: N and $CR^4$;
each $R^1$ is independently selected from the group consisting of:
  (1) —$(CH_2)_n$ $C_{3-7}$cycloalkyl,
  (2) —$(CH_2)_n$ $C_{2-6}$cycloheteroalkyl,
  (3) —$(CH_2)_n$ aryl, and
  (4) —$(CH_2)_n$ heteroaryl, wherein each $CH_2$, cycloalkyl, cycloheteroalkyl, aryl, and heteroaryl is unsubstituted or substituted with one to three groups independently selected from $R^a$;
each $R^2$ is independently selected from the group consisting of:
  (1) hydrogen, and
  (2) —$C_{1-6}$ alkyl;
each $R^3$ is independently selected from the group consisting of:
  (1) —$C_{1-6}$ alkyl,
  (2) —$(CH_2)_m$ $C_{3-7}$cycloalkyl,
  (3) —$(CH_2)_m$ $C_{2-6}$cycloheteroalkyl,
  (4) —$(CH_2)_m$ aryl,
  (5) —$(CH_2)_m$ biphenyl, and
  (6) —$(CH_2)_m$ heteroaryl,
wherein each $CH_2$, alkyl, cycloalkyl, cycloheteroalkyl, aryl, biphenyl and heteroaryl is unsubstituted or substituted with one to four groups independently selected from $R^b$;
each $R^4$ is independently selected from the group consisting of:
  (1) hydrogen,
  (2) —$C_{1-6}$ alkyl,
  (3) —$(CH_2)_p CO_2H$,
  (4) —$(CH_2)_p CO_2 C_{1-6}$ alkyl,
  (5) —$(CH_2)_p COC_{1-6}$ alkyl,
  (6) —$(CH_2)_p$—$NR^h$—$C_{1-6}$ alkyl,
  (7) —$(CH_2)_p$—O—$C_{1-6}$ alkyl,
  (8) —$(CH_2)_p$—S—$C_{1-6}$ alkyl,
  (9) —$(CH_2)_p$ $C_{3-7}$cycloalkyl,
  (10) —$(CH_2)_p$ $C_{2-6}$cycloheteroalkyl,
  (11) —$(CH_2)_p$ aryl, and
  (12) —$(CH_2)_p$ heteroaryl,
wherein each $CH_2$, alkyl, cycloalkyl, cycloheteroalkyl, aryl and heteroaryl is unsubstituted or substituted with one to three groups independently selected from $R^c$;
each $R^5$ is independently selected from the group consisting of:
  (1) hydrogen,
  (2) —$C_{1-6}$ alkyl,
  (3) —$(CH_2)_q CO_2H$,
  (4) —$(CH_2)_q CO_2 C_{1-6}$ alkyl,
  (5) —$(CH_2)_q CO$—$C_{1-6}$ alkyl,
  (6) —$(CH_2)_q CO$—$C_{3-6}$ cycloalkyl,
  (7) —$(CH_2)_q CO$—$C_{2-6}$ cycloheteroalkyl,
  (8) —$(CH_2)_q CO$-aryl,
  (9) —$(CH_2)_q CO$-heteroaryl,
  (10) —$(CH_2)_u$—$NR^h$—$C_{1-6}$ alkyl,
  (11) —$(CH_2)_u$—O—$C_{1-6}$ alkyl,
  (12) —$(CH_2)_u$—S—$C_{1-6}$ alkyl,
  (13) —$(CH_2)_q C_{3-7}$cycloalkyl,
  (14) —$(CH_2)_q C_{2-6}$cycloheteroalkyl,
  (15) —$(CH_2)_q$aryl, and
  (16) —$(CH_2)_q$heteroaryl,
wherein each $CH_2$, alkyl, cycloalkyl, cycloheteroalkyl, aryl and heteroaryl is unsubstituted or substituted with one to three groups independently selected from $R^d$;
each $R^6$ is independently selected from the group consisting of:
  (1) hydrogen,
  (2) —$C_{1-6}$ alkyl,
  (3) —$(CH_2)_v CF_3$,
  (4) —$(CH_2)_v OCF_3$,
  (5) —$(CH_2)_v N(R^h)_2$,
  (6) —$(CH_2)_v CONH(C_{1-4}$ alkyl),
  (7) —$(CH_2)_v CON(C_{1-4}$ alkyl$)_2$,
  (8) —$(CH_2)_v$—$NR^h$—CO—$C_{1-4}$ alkyl, (9) —$(CH_2)_v$—$NR^h$—$CO_2$—$C_{1-4}$ alkyl,
(10) —$(CH_2)_v$—$NR^h$—$(CH_2)_{0-2}$—C3-6cycloalkyl,
(11) —$(CH_2)_v$—$NR^h$—$(CH_2)_{0-2}$—C2-6cycloheteroalkyl,
(12) —$(CH_2)_v$—$NR^h$—$(CH_2)_{0-2}$-aryl,
(13) —$(CH_2)_v$—$NR^h$—$(CH_2)_{0-2}$-heteroaryl,
(14) —$(CH_2)_v$—$NR^h$—$(CH_2)_{1-2}$—O—$(CH_2)_{1-2}$—OH,
(15) —$(CH_2)_v$—$NR^h$—$(CH_2)_{1-2}$—O—$(CH_2)_{1-2}$—$OC_{1-6}$ alkyl,
(16) —$(CH_2)_v$—S—$C_{1-4}$ alkyl,
(17) —$(CH_2)_v$—$SO_2C_{1-4}$ alkyl,
(18) —$(CH_2)_v$—$SO_2$-phenyl,
(19) —$(CH_2)_v$—$NR^h$—$SO_2C_{1-4}$ alkyl,
(20) —$(CH_2)_v$—$NR^h$—$SO_2$phenyl,
(21) —$(CH_2)_v C_{3-7}$cycloalkyl,
(22) —$(CH_2)_v C_{2-6}$cycloheteroalkyl,
(23) —$(CH_2)_v$aryl, and
(24) —$(CH_2)_v$heteroaryl,
wherein each $CH_2$, alkyl, cycloalkyl, cycloheteroalkyl, phenyl, aryl and heteroaryl is unsubstituted or substituted with one to three substituents selected from $R^e$;
each $R^7$ is independently selected from the group consisting of:
(1) hydrogen, and
(2) —$C_{1-6}$ alkyl,
wherein alkyl is unsubstituted or substituted with one to three substituents selected from $R^f$;
each $R^8$ is independently selected from the group consisting of:
(1) hydrogen, and
(2) —$C_{1-6}$ alkyl;
each $R^9$ is independently selected from the group consisting of:
(1) hydrogen, and
(2) —$C_{1-6}$ alkyl;
wherein alkyl is unsubstituted or substituted with one to three substituents selected from $R^g$;
each $R^a$ is independently selected from the group consisting of:
(1) halogen,
(2) —CN,
(3) —OH,
(4) —$C_{1-6}$alkyl,
(5) —$OC_{1-6}$alkyl,
(6) —$CF_3$, and
(7) —$OCF_3$;
each $R^b$ is independently selected from the group consisting of:
(1) halogen,
(2) —CN,
(3) —OH,
(4) —$C_{1-6}$alkyl,
(5) —$OC_{1-6}$alkyl,
(6) —$CF_3$, and
(7) —$OCF_3$;
each $R^c$ is independently selected from the group consisting of:
(1) halogen, and
(2) —$C_{1-6}$ alkyl;
each $R^d$ is independently selected from the group consisting of:
(1) halogen,
(2) —CN,
(3) —OH,
(4) —$C_{1-6}$alkyl,
(5) —$OC_{1-6}$alkyl,
(6) —$CF_3$,
(7) —$OCF_3$, and
(8) —$C(O)C_{1-6}$alkyl;
each $R^e$ is independently selected from the group consisting of:
(1) hydrogen,
(2) halogen,
(3) —CN,
(4) —OH,
(5) —$C_{1-6}$alkyl,
(6) —$OC_{1-6}$alkyl,
(7) —$CF_3$,
(8) —$OCF_3$, and
(9) —$C_{3-6}$ cycloalkyl;
each $R^f$ is independently selected from the group consisting of:
(1) hydrogen,
(2) halogen, and
(3) $C_{1-6}$ alkyl;
each $R^g$ is independently selected from the group consisting of:
(1) hydrogen,
(2) halogen, and
(3) $C_{1-6}$ alkyl;
each $R^h$ is independently selected from the group consisting of:
(1) hydrogen, and
(2) $C_{1-6}$ alkyl;
m is selected from 0, 1, 2, and 3;
n is selected from 0, 1, 2, and 3;
p is selected from 0, 1, 2, and 3;
q is selected from 0, 1, 2, and 3;
r is selected from 0, 1 and 2;
s is selected from 1 and 2;
t is selected from 0, 1, 2, and 3;
u is 1, 2, or 3; and
v is selected from 0, 1, 2, and 3.

2. The compound of claim 1 wherein $R^2$ is hydrogen; or a pharmaceutically acceptable salt thereof.

3. The compound of claim 1 wherein each $R^3$ is —$(CH_2)_m$ aryl, wherein each $CH_2$ and aryl is unsubstituted or substituted with one to three groups independently selected from $R^b$;
or a pharmaceutically acceptable salt thereof.

4. The compound of claim 3 wherein each $R^3$ is phenyl, wherein phenyl is unsubstituted or substituted with one to three groups independently selected from $R^b$;
or a pharmaceutically acceptable salt thereof.

5. The compound of claim 1 wherein each $R^1$ is independently selected from the group consisting of:
(1) —$(CH_2)_n$ aryl, and
(2) —$(CH_2)_n$ heteroaryl,
wherein each $CH_2$, aryl and heteroaryl is unsubstituted or substituted with one to three groups independently selected from $R^a$;
or a pharmaceutically acceptable salt thereof.

6. The compound of claim 5 wherein each $R^1$ is phenyl, wherein phenyl is unsubstituted or substituted with one to three groups independently selected from $R^a$; or a pharmaceutically acceptable salt thereof.

7. The compound of claim 1 wherein each $R^4$ is independently selected from the group consisting of:
(1) hydrogen,
(2) —$C_{1-6}$ alkyl, and
(3) —$(CH_2)_p$ heteroaryl,
wherein each $CH_2$, alkyl and heteroaryl is unsubstituted or substituted with one to three groups independently selected from $R^c$;
or a pharmaceutically acceptable salt thereof.

8. The compound of claim 7 wherein each $R^4$ is $-C_{1-6}$ alkyl, wherein each alkyl is unsubstituted or substituted with one to three groups independently selected from $R^c$;
or a pharmaceutically acceptable salt thereof.

9. The compound of claim 1 wherein each $R^5$ is independently selected from the group consisting of:
   (1) hydrogen,
   (2) $-C_{1-6}$ alkyl, and
   (3) $-(CH_2)_q$ heteroaryl,
wherein each $CH_2$, alkyl and heteroaryl is unsubstituted or substituted with one to three groups independently selected from $R^d$;
or a pharmaceutically acceptable salt thereof.

10. The compound of claim 1 wherein each $R^5$ is independently selected from the group consisting of:
    (1) hydrogen, and
    (2) $-C_{1-6}$ alkyl,
wherein each alkyl is unsubstituted or substituted with one to three groups independently selected from $R^d$;
or a pharmaceutically acceptable salt thereof.

11. The compound of claim 1 wherein each $R^6$ is independently selected from the group consisting of:
    (1) $-(CH_2)_v N(R^h)_2$,
    (2) $-(CH_2)_v-NR^h-(CH_2)_{0-2}-C3\text{-}6\text{cycloalkyl}$,
    (3) $-(CH_2)_v-NR^h-(CH_2)_{0-2}\text{-aryl}$,
    (4) $-(CH_2)_v-NR^h-(CH_2)_{1-2}-O-(CH_2)_{1-2}-OH$,
    (5) $-(CH_2)_v-NR^h-(CH_2)_{1-2}-O-(CH_2)_{1-2}-OC_{1-6}$ alkyl, and
    (6) $-(CH_2)_v C_{2-6}\text{cycloheteroalkyl}$,
wherein each $CH_2$, alkyl, cycloalkyl, cycloheteroalkyl and aryl is unsubstituted or substituted with one to three substituents selected from $R^e$;
or a pharmaceutically acceptable salt thereof.

12. The compound of claim 11 wherein each $R^6$ is independently selected from the group consisting of:
    (1) $-(CH_2)_v N(R^h)_2$,
    (2) $-(CH_2)_v-NR^h-(CH_2)_{0-2}-C3\text{-}6\text{cycloalkyl}$,
    (3) $-(CH_2)_v-NR^h-(CH_2)_{0-2}\text{-aryl}$,
    (4) $-(CH_2)_v-NR^h-(CH_2)_{1-2}-O-(CH_2)_{1-2}-OC_{1-6}$ alkyl, and
    (5) $-(CH_2)_v C_{2-6}\text{cycloheteroalkyl}$,
wherein each $CH_2$, alkyl, cycloalkyl, cycloheteroalkyl and aryl is unsubstituted or substituted with one to three substituents selected from $R^e$;
or a pharmaceutically acceptable salt thereof.

13. The compound of claim 1 wherein each $R^6$ is independently selected from the group consisting of:
    (1) $-(CH_2)_v N(R^h)_2$,
    (2) $-(CH_2)_v-NR^h-(CH_2)_{1-2}-O-(CH_2)_{1-2}-OH$, and
    (3) $-(CH_2)_v C_{2-6}\text{cycloheteroalkyl}$,
wherein each $CH_2$, alkyl and cycloheteroalkyl is unsubstituted or substituted with one to three substituents selected from $R^e$;
or a pharmaceutically acceptable salt thereof.

14. The compound of claim 13 wherein each $R^6$ is independently selected from the group consisting of:
    (1) $-(CH_2)_v N(R^h)_2$, and
    (2) $-(CH_2)_v C_{2-6}\text{cycloheteroalkyl}$,
wherein each $CH_2$, alkyl and cycloheteroalkyl is unsubstituted or substituted with one to three substituents selected from $R^e$;
or a pharmaceutically acceptable salt thereof.

15. The compound of claim 1 wherein Z is $CR^4$; or a pharmaceutically acceptable salt thereof.

16. The compound of claim 1 wherein:
X is independently selected from the group consisting of: N and $CR^8$;
Y is independently selected from the group consisting of: $NR^5$ or $CR^6R^7$;
Z is independently selected from the group consisting of: N and $CR^4$;
$R^1$ is independently selected from the group consisting of:
    (1) $-(CH_2)_n$ aryl, and
    (2) $-(CH_2)_n$ heteroaryl,
wherein each $CH_2$, aryl and heteroaryl is unsubstituted or substituted with one to three groups independently selected from $R^a$;
$R^2$ is hydrogen;
$R^3$ is $-(CH_2)_m$ aryl, wherein each $CH_2$ and aryl is unsubstituted or substituted with one to three groups independently selected from $R^b$;
$R^4$ is independently selected from the group consisting of:
    (1) hydrogen,
    (2) $-C_{1-6}$ alkyl, and
    (3) $-(CH_2)_p$ heteroaryl,
wherein each $CH_2$, alkyl and heteroaryl is unsubstituted or substituted with one to three groups independently selected from $R^c$;
$R^5$ is independently selected from the group consisting of:
    (1) hydrogen,
    (2) $-C_{1-6}$ alkyl, and
    (3) $-(CH_2)_q$ heteroaryl,
wherein each $CH_2$, alkyl and heteroaryl is unsubstituted or substituted with one to three groups independently selected from $R^d$;
$R^6$ is independently selected from the group consisting of:
    (1) $-(CH_2)_v N(R^h)_2$,
    (2) $-(CH_2)_v-NR^h-(CH_2)_{0-2}-C3\text{-}6\text{cycloalkyl}$,
    (3) $-(CH_2)_v-NR^h-(CH_2)_{0-2}\text{-aryl}$,
    (4) $-(CH_2)_v-NR^h-(CH_2)_{1-2}-O-(CH_2)_{1-2}-OH$,
    (5) $-(CH_2)_v-NR^h-(CH_2)_{1-2}-O-(CH_2)_{1-2}-OC_{1-6}$ alkyl, and
    (6) $-(CH_2)_v C_{2-6}\text{cycloheteroalkyl}$,
wherein each $CH_2$, alkyl, cycloalkyl, cycloheteroalkyl and aryl is unsubstituted or substituted with one to three substituents selected from $R^e$;
or a pharmaceutically acceptable salt thereof.

17. The compound of claim 1 wherein:
X is independently selected from the group consisting of: N and CH;
Y is independently selected from the group consisting of: $NR^5$ or $CR^6R^7$;
Z is $CR^4$;
$R^1$ is phenyl, wherein phenyl is unsubstituted or substituted with one to three groups independently selected from $R^a$;
$R^2$ is hydrogen;
$R^3$ is phenyl, wherein phenyl is unsubstituted or substituted with one to three groups independently selected from $R^b$;
$R^4$ is independently selected from the group consisting of: hydrogen, and $-C_{1-6}$ alkyl, wherein each alkyl is unsubstituted or substituted with one to three groups independently selected from $R^c$;
$R^5$ is independently selected from the group consisting of:
    (1) hydrogen, and
    (2) $-C_{1-6}$ alkyl,
wherein each alkyl is unsubstituted or substituted with one to three groups independently selected from $R^d$;
$R^6$ is independently selected from the group consisting of:
    (1) $-(CH_2)_v N(R^h)_2$, and
    (2) $-(CH_2)_v C_{2-6}\text{cycloheteroalkyl}$, wherein each CH₂, alkyl and cycloheteroalkyl is unsubstituted or substituted with one to three substituents selected from R^e;
or a pharmaceutically acceptable salt thereof.
18. The compound of claim 17 selected from the group consisting of:
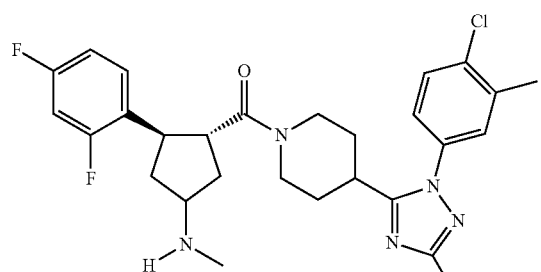
,
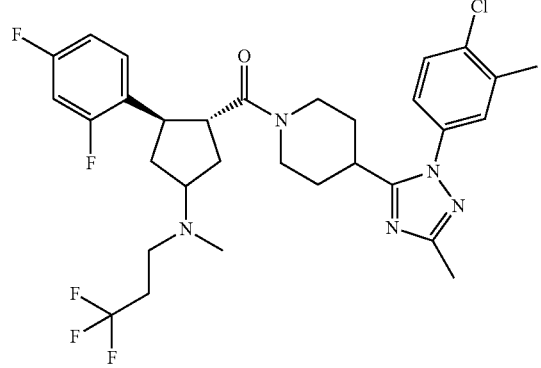
,
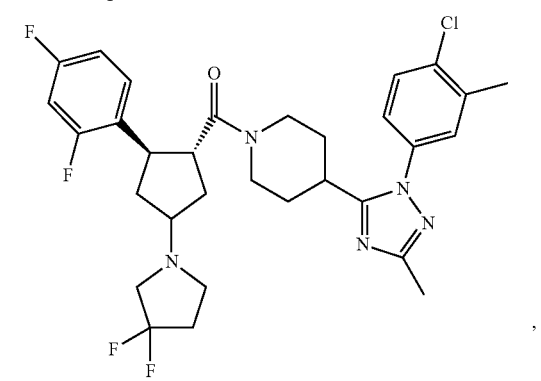
,
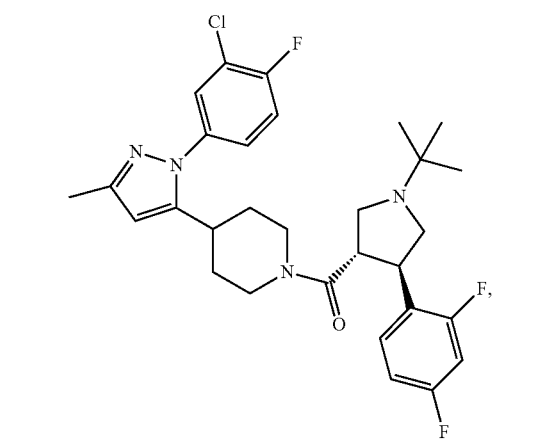
,
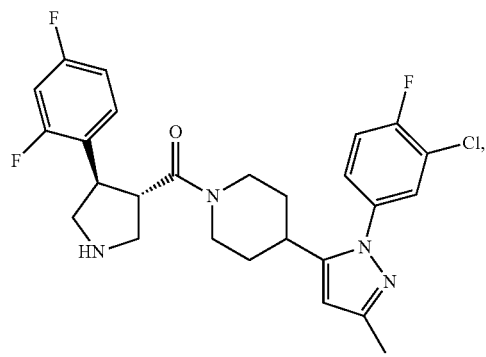
,
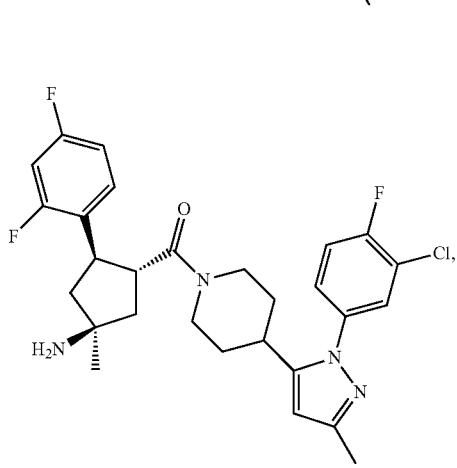
,
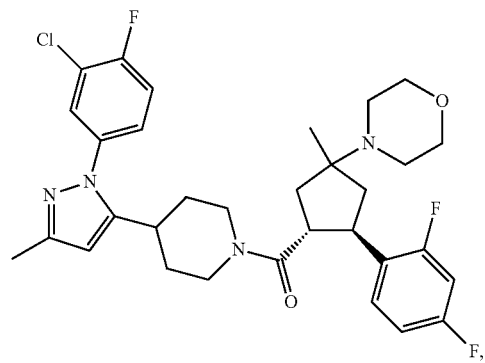
,
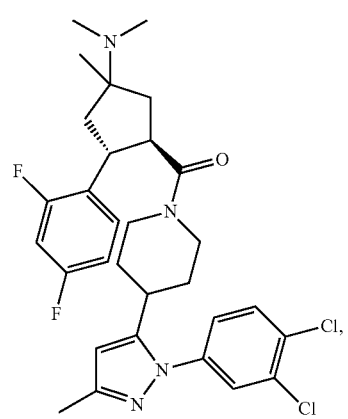

-continued

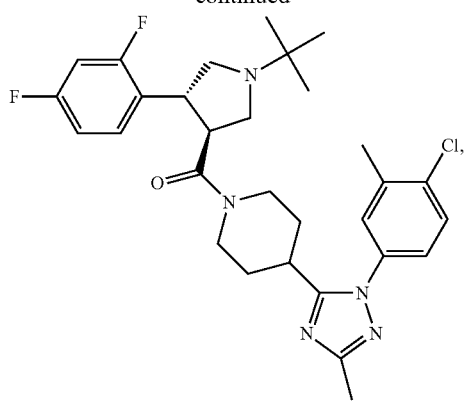

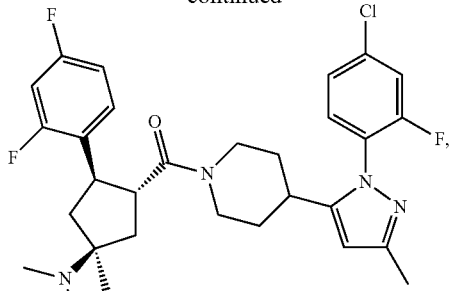

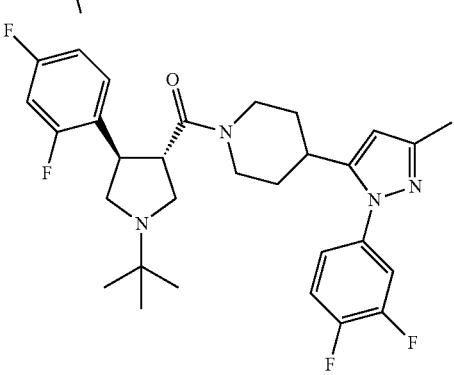

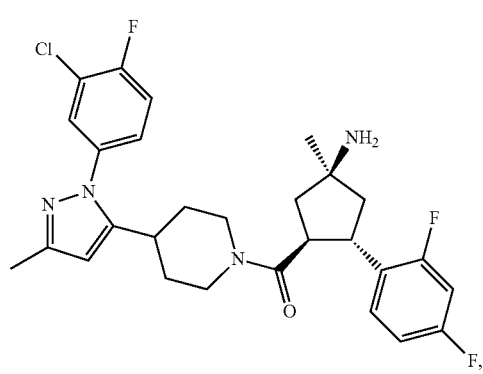

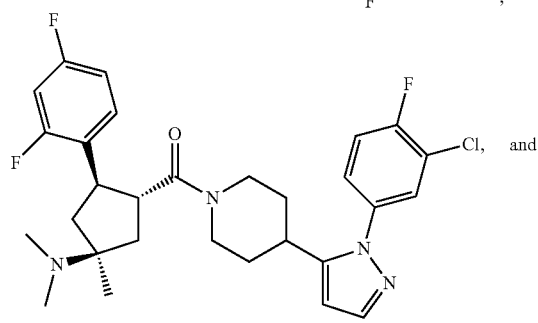

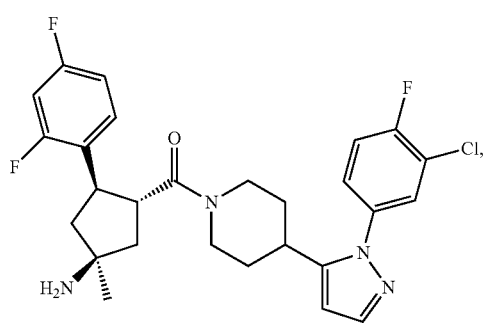

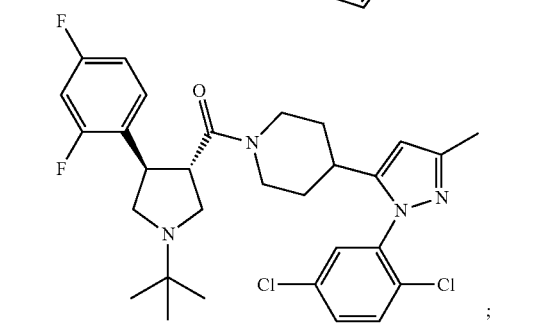

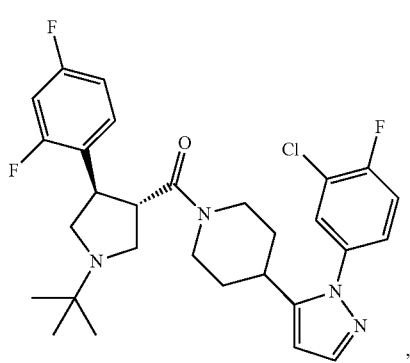

or a pharmaceutically acceptable salt thereof.

19. A pharmaceutical composition comprising a compound of claim 1 in combination with a pharmaceutically acceptable carrier.

20. A composition comprising a compound according to claim 1 and a compound selected from simvastatin, ezetimibe, taranabant and sitagliptin; and a pharmaceutically acceptable carrier.

21. A method of treating a disorder, condition, or disease responsive to the inhibition of prolylcarboxypeptidase in a patient suffering from said disorder, condition, or disease, comprising administration of a therapeutic effective amount of a compound according to claim 1, wherein the disorder, condition, or disease responsive to the inhibition of prolylcarboxypeptidase is selected from the group consisting of hypertension, insulin resistance, hyperlipidemia, endometrial cancer, breast cancer, prostate cancer, colon cancer, kidney cancer, lower back pain, cardiac hypertrophy, left ventricular hypertrophy, gallbladder disease, gout, osteoarthritis, obstructive sleep apnea, heart arrhythmias, myocardial infarction, sexual dysfunction, infertility, hirsutism, infertility, obesity-related gastro-esophageal reflux, inflammation, Pickwickian syndrome, systemic inflammation of the vasculature, arteriosclerosis, hypercholesterolemia, hyperuricaemia, constipation, irritable bowel syndrome, inflammatory bowel syndrome, hyperglycemia, low glucose tolerance, obesity, dyslipidemia, hypertriglyceridemia, hypercholesterolemia, vascular restenosis, Crohn's disease, ulcerative colitis, pancreatitis, retinopathy, nephropathy, neuropathy, and ovarian hyperandrogenism.

22. The method of claim 21 wherein the disorder, condition, or disease is obesity.

\* \* \* \* \*